(12) United States Patent
O'Grady et al.

(10) Patent No.: US 12,245,862 B2
(45) Date of Patent: *Mar. 11, 2025

(54) ELECTRODE PATCH AND CONNECTION SYSTEM

(71) Applicant: Alimetry Limited, Auckland (NZ)

(72) Inventors: Gregory O'Grady, Auckland (NZ); Armen Gharibans, Auckland (NZ); Peng Du, Auckland (NZ); Thomas Hayes, Auckland (NZ); James Sebastian Hannon-Tan, North Adelaide (AU)

(73) Assignee: Alimetry Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 18/738,822

(22) Filed: Jun. 10, 2024

(65) Prior Publication Data

US 2024/0324930 A1 Oct. 3, 2024

Related U.S. Application Data

(63) Continuation of application No. 17/788,070, filed as application No. PCT/IB2020/062369 on Dec. 23, 2020, now Pat. No. 12,178,580.

(30) Foreign Application Priority Data

Dec. 23, 2019 (NZ) .......................................... 760518
Nov. 11, 2020 (NZ) .......................................... 769806

(51) Int. Cl.
*A61B 5/273* (2021.01)
*A61B 5/00* (2006.01)
(Continued)

(52) U.S. Cl.
CPC ................ *A61B 5/273* (2021.01); *A61B 5/24* (2021.01); *A61B 5/25* (2021.01); *A61B 5/392* (2021.01);
(Continued)

(58) Field of Classification Search
CPC ....... A61B 5/273; A61B 5/392; A61B 5/4255; A61B 5/25; A61B 5/24; A61B 2562/277; A61B 5/6833
See application file for complete search history.

(56) References Cited

U.S. PATENT DOCUMENTS 2,409,033 A 10/1946 Lovett
3,411,495 A 11/1968 Casby
(Continued)

FOREIGN PATENT DOCUMENTS

AR 058368 A1 1/2008
AT 213134 T 2/2002
(Continued)

OTHER PUBLICATIONS

US 9,241,675 B2, 01/2016, Dubois et al. (withdrawn)
US 9,433,364 B2, 09/2016, Zeng et al. (withdrawn)

*Primary Examiner* — Adam Z Minchella
(74) *Attorney, Agent, or Firm* — Kilpatrick Townsend & Stockton LLP

(57) ABSTRACT

An electrode patch 100 for monitoring electrical activity generated by a subject is disclosed. The electrode patch comprises a plurality of spatially arranged electrodes 102 for contacting an outer surface of a skin of the subject to sense and measure electrical potentials at multiple electrodes 102. The electrode patch 100 further comprises at least one connector portion 104 for connecting to a connector of a connector device. The connector portion 104 is spaced apart from the electrodes 102 and is electrically connected with
(Continued)

the electrodes 102. A connector device for connecting to such electrode patch is also disclosed.

19 Claims, 23 Drawing Sheets

(51) Int. Cl.
*A61B 5/24* (2021.01)
*A61B 5/25* (2021.01)
*A61B 5/392* (2021.01)

(52) U.S. Cl.
CPC .......... *A61B 5/4255* (2013.01); *A61B 5/6833* (2013.01); *A61B 2562/225* (2013.01)

(56) References Cited

U.S. PATENT DOCUMENTS

| | | |
|---|---|---|
| 3,525,330 A | 8/1970 | Greene |
| 3,534,727 A | 10/1970 | Roman |
| 4,016,868 A | 4/1977 | Allison |
| 4,026,278 A | 5/1977 | Ricketts et al. |
| 4,202,344 A | 5/1980 | Mills et al. |
| 4,381,012 A | 4/1983 | Russek |
| 4,391,279 A | 7/1983 | Stein |
| 4,425,921 A | 1/1984 | Fujisaki et al. |
| 4,498,480 A | 2/1985 | Mortensen |
| 4,557,271 A | 12/1985 | Stoller et al. |
| 4,580,572 A | 4/1986 | Granek et al. |
| 4,608,987 A | 9/1986 | Mills |
| 4,681,118 A | 7/1987 | Asai et al. |
| 4,683,892 A | 8/1987 | Johansson et al. |
| 4,773,427 A | 9/1988 | Inoue et al. |
| 4,832,608 A | 5/1989 | Kroll |
| 4,834,103 A | 5/1989 | Heath |
| 4,889,131 A | 12/1989 | Salem et al. |
| 4,920,490 A | 4/1990 | Isaacson |
| 5,054,496 A | 10/1991 | Wen et al. |
| 5,078,138 A | 1/1992 | Strand et al. |
| 5,247,436 A | 9/1993 | Stone |
| 5,282,469 A | 2/1994 | Deuter et al. |
| 5,291,888 A | 3/1994 | Tucker |
| 5,307,818 A | 5/1994 | Segalowitz |
| 5,337,362 A | 8/1994 | Gormish et al. |
| 5,345,934 A | 9/1994 | Highe et al. |
| 5,348,008 A | 9/1994 | Bornn et al. |
| 5,357,957 A | 10/1994 | Itil et al. |
| 5,445,149 A | 8/1995 | Rotolo et al. |
| 5,450,845 A | 9/1995 | Axelgaard |
| 5,456,254 A | 10/1995 | Pietroski et al. |
| 5,465,727 A | 11/1995 | Reinhold |
| 5,507,290 A | 4/1996 | Kelly et al. |
| 5,518,007 A | 5/1996 | Becker |
| 5,564,433 A | 10/1996 | Thornton |
| 5,578,344 A | 11/1996 | Ahr et al. |
| 5,591,213 A | 1/1997 | Morgan |
| 5,678,545 A | 10/1997 | Stratbucker |
| 5,704,368 A | 1/1998 | Asano et al. |
| 5,724,984 A | 3/1998 | Arnold et al. |
| 5,733,151 A | 3/1998 | Edsall et al. |
| 5,746,207 A | 5/1998 | Mclaughlin et al. |
| 5,749,367 A | 5/1998 | Gamlyn et al. |
| 5,782,238 A | 7/1998 | Beitler |
| 5,795,293 A | 8/1998 | Carim et al. |
| 5,795,304 A | 8/1998 | Sun et al. |
| 5,813,404 A | 9/1998 | Devlin et al. |
| 5,813,981 A | 9/1998 | Carim |
| 5,857,980 A | 1/1999 | Wilson |
| 5,947,897 A | 9/1999 | Otake |
| 5,995,861 A | 11/1999 | Price |
| 6,002,957 A | 12/1999 | Finneran |
| 6,032,064 A | 2/2000 | Devlin et al. |
| 6,055,448 A | 4/2000 | Anderson et al. |
| 6,065,154 A | 5/2000 | Hulings et al. |
| 6,067,464 A | 5/2000 | Musha |
| 6,073,039 A | 6/2000 | Berson |
| 6,091,977 A | 7/2000 | Tarjan et al. |
| 6,115,623 A | 9/2000 | Mcfee |
| 6,161,036 A | 12/2000 | Matsumura et al. |
| 6,201,981 B1 | 3/2001 | Yarita |
| 6,205,346 B1 | 3/2001 | Akiva |
| 6,223,088 B1 | 4/2001 | Scharnberg et al. |
| 6,298,255 B1 | 10/2001 | Cordero et al. |
| 6,351,665 B1 | 2/2002 | Koch |
| 6,393,317 B1 | 5/2002 | Fukuda et al. |
| 6,400,975 B1 | 6/2002 | McFee |
| 6,408,200 B1 | 6/2002 | Takashina |
| 6,415,169 B1 | 7/2002 | Kornrumpf et al. |
| 6,434,420 B1 | 8/2002 | Taheri |
| 6,438,406 B2 | 8/2002 | Yonce |
| 6,440,069 B1 | 8/2002 | Raymond et al. |
| 6,453,186 B1 | 9/2002 | Lovejoy et al. |
| 6,456,872 B1 | 9/2002 | Faisandier |
| 6,494,829 B1 | 12/2002 | New, Jr. et al. |
| 6,516,289 B2 | 2/2003 | David |
| 6,553,246 B1 | 4/2003 | Wenger |
| 6,560,473 B2 | 5/2003 | Dominguez |
| 6,571,115 B2 | 5/2003 | Axelgaard et al. |
| 6,571,123 B2 | 5/2003 | Ives et al. |
| 6,611,705 B2 | 8/2003 | Hopman et al. |
| 6,616,608 B2 | 9/2003 | Honda et al. |
| 6,625,485 B2 | 9/2003 | Levendowski et al. |
| 6,636,754 B1 | 10/2003 | Baura et al. |
| 6,643,539 B2 | 11/2003 | Meij et al. |
| 6,654,633 B2 | 11/2003 | Stengel et al. |
| 6,708,050 B2 | 3/2004 | Carim |
| 6,725,089 B2 | 4/2004 | Komatsu et al. |
| 6,751,499 B2 | 6/2004 | Lange et al. |
| 6,768,921 B2 | 7/2004 | Organ et al. |
| 6,772,004 B2 | 8/2004 | Rudy |
| 6,788,966 B2 | 9/2004 | Kenan |
| 6,807,438 B1 | 10/2004 | Brun et al. |
| 6,830,551 B1 | 12/2004 | Uchigaki et al. |
| 6,832,987 B2 | 12/2004 | David et al. |
| 6,847,836 B1 | 1/2005 | Sujdak |
| 6,849,052 B2 | 2/2005 | Uchigaki et al. |
| 6,901,286 B1 | 5/2005 | Sinderby et al. |
| 6,912,414 B2 | 6/2005 | Tong |
| 6,915,148 B2 | 7/2005 | Finneran et al. |
| 6,961,601 B2 | 11/2005 | Matthews et al. |
| 6,984,297 B2 | 1/2006 | Nisch et al. |
| 7,020,508 B2 | 3/2006 | Stivoric et al. |
| 7,136,690 B2 | 11/2006 | Helzel et al. |
| 7,154,071 B2 | 12/2006 | Sattler et al. |
| 7,206,625 B2 | 4/2007 | Kurtz et al. |
| 7,225,009 B2 | 5/2007 | Borgmeier et al. |
| 7,257,438 B2 | 8/2007 | Kinast |
| 7,262,703 B2 | 8/2007 | Collins |
| 7,266,405 B1 | 9/2007 | Alroy et al. |
| 7,286,865 B2 | 10/2007 | Nazeri |
| 7,299,084 B1 | 11/2007 | Price |
| 7,379,766 B2 | 5/2008 | Gabl et al. |
| 7,395,105 B2 | 7/2008 | Schmidt et al. |
| 7,572,231 B2 | 8/2009 | Pearlman |
| 7,593,768 B1 | 9/2009 | Vasiliev et al. |
| 7,634,311 B2 | 12/2009 | Blomberg et al. |
| 7,668,580 B2 | 2/2010 | Shin et al. |
| 7,668,588 B2 | 2/2010 | Kovacs |
| 7,670,295 B2 | 3/2010 | Sackner et al. |
| 7,672,703 B2 | 3/2010 | Yeo et al. |
| 7,699,840 B2 | 4/2010 | Eisele |
| 7,715,894 B2 | 5/2010 | Dunseath et al. |
| 7,715,921 B2 | 5/2010 | Palti |
| 7,758,522 B2 | 7/2010 | Pandit |
| 7,783,334 B2 | 8/2010 | Nam et al. |
| 7,786,562 B2 | 8/2010 | Ozguz et al. |
| 7,826,882 B2 | 11/2010 | Mcintire et al. |
| 7,896,807 B2 | 3/2011 | Clancy et al. |
| 7,899,520 B2 | 3/2011 | Lian et al. |
| 7,904,133 B2 | 3/2011 | Gehman et al. |
| 7,904,180 B2 | 3/2011 | Juola et al. |
| 7,917,201 B2 | 3/2011 | Gozani et al. |
| 7,949,389 B2 | 5/2011 | Wolfberg et al. |
| 7,966,074 B2 | 6/2011 | Kim et al. |

(56) References Cited

U.S. PATENT DOCUMENTS

| | | |
|---|---|---|
| 7,996,056 B2 | 8/2011 | Rowlandson et al. |
| 8,060,175 B2 | 11/2011 | Rowlandson et al. |
| 8,060,191 B2 | 11/2011 | Chen |
| 8,097,926 B2 | 1/2012 | De Graff et al. |
| 8,112,139 B2 | 2/2012 | Sun et al. |
| 8,112,141 B2 | 2/2012 | Wilson et al. |
| 8,131,335 B2 | 3/2012 | Silber |
| 8,140,143 B2 | 3/2012 | Picard et al. |
| 8,160,328 B2 | 4/2012 | Goetz et al. |
| 8,170,656 B2 | 5/2012 | Tan et al. |
| 8,175,674 B2 | 5/2012 | Schmidt et al. |
| 8,180,425 B2 | 5/2012 | Selvitelli et al. |
| 8,214,007 B2 | 7/2012 | Baker et al. |
| 8,238,995 B2 | 8/2012 | Chandrasekaran et al. |
| 8,238,996 B2 | 8/2012 | Burnes et al. |
| 8,248,137 B2 | 8/2012 | Peuscher |
| 8,261,428 B2 | 9/2012 | Fang et al. |
| 8,280,503 B2 | 10/2012 | Linderman |
| 8,311,605 B2 | 11/2012 | Wilder-smith et al. |
| 8,315,687 B2 | 11/2012 | Cross et al. |
| 8,320,988 B2 | 11/2012 | Axelgaard |
| 8,332,009 B2 | 12/2012 | Mclaughlin et al. |
| 8,332,020 B2 | 12/2012 | Zdeblick |
| 8,352,012 B2 | 1/2013 | Besio |
| 8,372,726 B2 | 2/2013 | De Graff et al. |
| 8,389,862 B2 | 3/2013 | Arora et al. |
| 8,406,843 B2 | 3/2013 | Tiegs et al. |
| 8,428,673 B2 | 4/2013 | Cho et al. |
| 8,437,843 B1 | 5/2013 | Kayyali et al. |
| 8,467,860 B2 | 6/2013 | Salazar et al. |
| 8,473,024 B2 | 6/2013 | Causevic et al. |
| D687,152 S | 7/2013 | Tilk et al. |
| 8,494,620 B2 | 7/2013 | Rey |
| 8,536,667 B2 | 9/2013 | Arora et al. |
| 8,548,558 B2 | 10/2013 | Dunagan et al. |
| 8,560,040 B2 | 10/2013 | Gehman et al. |
| 8,583,215 B2 | 11/2013 | Lichtenstein |
| 8,591,599 B1 | 11/2013 | Kaliki et al. |
| 8,594,764 B2 | 11/2013 | Rice et al. |
| 8,606,353 B2 | 12/2013 | Yeo et al. |
| 8,611,980 B2 | 12/2013 | Choe et al. |
| 8,626,260 B2 | 1/2014 | Crosby |
| 8,626,261 B2 | 1/2014 | Ko et al. |
| 8,630,699 B2 | 1/2014 | Baker et al. |
| 8,647,270 B2 | 2/2014 | Leboeuf et al. |
| 8,652,126 B2 | 2/2014 | Rantala |
| 8,668,651 B2 | 3/2014 | Burnes et al. |
| 8,688,209 B2 | 4/2014 | Verbitskiy |
| 8,700,118 B2 | 4/2014 | Oster et al. |
| 8,700,122 B2 | 4/2014 | Cordero et al. |
| 8,706,182 B2 | 4/2014 | Yamashita |
| 8,706,215 B2 | 4/2014 | Kaib et al. |
| 8,725,241 B2 | 5/2014 | Ramanathan et al. |
| 8,731,632 B1 | 5/2014 | Sereboff et al. |
| 8,750,974 B2 | 6/2014 | Baker et al. |
| 8,755,859 B2 | 6/2014 | Lang |
| 8,761,858 B1 | 6/2014 | Huttner |
| 8,771,184 B2 | 7/2014 | Besson et al. |
| 8,774,894 B2 | 7/2014 | Lee |
| 8,781,551 B2 | 7/2014 | Chetham |
| 8,788,009 B2 | 7/2014 | Greene et al. |
| 8,792,957 B2 | 7/2014 | Greene et al. |
| 8,792,974 B2 | 7/2014 | Rothman |
| 8,792,975 B2 | 7/2014 | Kato et al. |
| 8,797,331 B2 | 8/2014 | Sano et al. |
| 8,798,708 B2 | 8/2014 | Tremblay |
| 8,814,574 B2 | 8/2014 | Selby et al. |
| 8,818,482 B2 | 8/2014 | Phillips et al. |
| 8,825,128 B2 | 9/2014 | Ylostalo et al. |
| 8,838,218 B2 | 9/2014 | Khair |
| 8,849,387 B2 | 9/2014 | Gilbert et al. |
| 8,858,432 B2 | 10/2014 | Robertson et al. |
| 8,868,152 B2 | 10/2014 | Burnes et al. |
| 8,868,205 B2 | 10/2014 | Ross et al. |
| 8,874,185 B2 | 10/2014 | Sonnenborg |
| 8,886,281 B2 | 11/2014 | Pernu et al. |
| 8,886,334 B2 | 11/2014 | Ghaffari et al. |
| 8,892,181 B2 | 11/2014 | Wolfberg et al. |
| 8,897,851 B2 | 11/2014 | Caprio et al. |
| 8,897,860 B2 | 11/2014 | Volpe et al. |
| 8,903,477 B2 | 12/2014 | Berkner |
| 8,923,958 B2 | 12/2014 | Gupta et al. |
| 8,926,509 B2 | 1/2015 | Magar et al. |
| 8,934,957 B2 | 1/2015 | Dias et al. |
| 8,934,965 B2 | 1/2015 | Rogers et al. |
| 8,954,129 B1 | 2/2015 | Schlegel et al. |
| 8,965,492 B2 | 2/2015 | Baker et al. |
| 8,965,518 B1 | 2/2015 | Ellrich et al. |
| 8,965,534 B2 | 2/2015 | Hyatt et al. |
| 8,979,755 B2 | 3/2015 | Szydlo-Moore et al. |
| 8,981,948 B2 | 3/2015 | Olde et al. |
| 8,983,591 B2 | 3/2015 | Leininger et al. |
| 8,983,627 B2 | 3/2015 | Pelger et al. |
| 8,986,295 B2 | 3/2015 | Nessler et al. |
| 8,989,850 B2 | 3/2015 | Balda |
| 8,999,259 B2 | 4/2015 | King et al. |
| 9,012,784 B2 | 4/2015 | Arora et al. |
| 9,014,795 B1 | 4/2015 | Yang |
| 9,020,013 B2 | 4/2015 | Peuscher |
| 9,021,358 B2 | 4/2015 | Amble et al. |
| 9,024,619 B2 | 5/2015 | Caprio et al. |
| 9,042,596 B2 | 5/2015 | Connor |
| 9,042,957 B2 | 5/2015 | Li et al. |
| 9,055,879 B2 | 6/2015 | Selby et al. |
| 9,060,705 B2 | 6/2015 | Holzhacker et al. |
| 9,107,571 B2 | 8/2015 | Strauss et al. |
| 9,119,533 B2 | 9/2015 | Ghaffari |
| 9,123,614 B2 | 9/2015 | Graff et al. |
| 9,155,484 B2 | 10/2015 | Baker et al. |
| 9,167,981 B2 | 10/2015 | Kuo et al. |
| 9,173,581 B2 | 11/2015 | Boettcher et al. |
| 9,186,060 B2 | 11/2015 | De Graff et al. |
| 9,198,621 B2 | 12/2015 | Fernstrom et al. |
| 9,237,857 B2 | 1/2016 | Guger et al. |
| 9,259,168 B2 | 2/2016 | Marashdeh et al. |
| 9,271,680 B2 | 3/2016 | Dubois et al. |
| 9,289,132 B2 | 3/2016 | Ghaffari et al. |
| 9,300,066 B2 | 3/2016 | Venaleck et al. |
| 9,326,694 B2 | 5/2016 | Cho et al. |
| 9,398,864 B2 | 7/2016 | Lawrence et al. |
| 9,420,956 B2 | 8/2016 | Gopalakrishnan et al. |
| 9,427,166 B2 | 8/2016 | Dubois et al. |
| 9,433,366 B2 | 9/2016 | Baker et al. |
| 9,439,574 B2 | 9/2016 | Mccombie et al. |
| 9,445,737 B2 | 9/2016 | Bokan et al. |
| 9,470,728 B2 | 10/2016 | George et al. |
| 9,474,482 B2 | 10/2016 | Devanaboyina |
| 9,486,133 B2 | 11/2016 | Lee et al. |
| 9,498,129 B2 | 11/2016 | Buck et al. |
| 9,504,427 B2 | 11/2016 | George et al. |
| 9,516,758 B2 | 12/2016 | Arora et al. |
| 9,545,216 B2 | 1/2017 | Dangelo et al. |
| 9,545,285 B2 | 1/2017 | Ghaffari et al. |
| 9,545,514 B2 | 1/2017 | Minogue et al. |
| 9,546,898 B2 | 1/2017 | Kovacs |
| 9,572,507 B2 | 2/2017 | Moore et al. |
| 9,585,614 B2 | 3/2017 | Dugan |
| 9,591,981 B2 | 3/2017 | Levin et al. |
| 9,597,004 B2 | 3/2017 | Hughes et al. |
| 9,603,542 B2 | 3/2017 | Veen et al. |
| 9,622,672 B2 | 4/2017 | Yoshida et al. |
| 9,622,680 B2 | 4/2017 | Ghaffari et al. |
| 9,629,586 B2 | 4/2017 | Ghaffari et al. |
| 9,629,952 B2 | 4/2017 | Heppe et al. |
| 9,642,548 B2 | 5/2017 | Sano et al. |
| 9,655,528 B2 | 5/2017 | Zhu |
| 9,655,546 B2 | 5/2017 | Shen et al. |
| 9,655,560 B2 | 5/2017 | Ghaffari et al. |
| 9,655,561 B2 | 5/2017 | Tilk et al. |
| 9,662,024 B2 | 5/2017 | Livneh et al. |
| 9,662,030 B2 | 5/2017 | Thng et al. |
| 9,662,069 B2 | 5/2017 | De Graff et al. |
| 9,668,664 B2 | 6/2017 | Zeng et al. |
| 9,668,669 B2 | 6/2017 | Powell et al. |

(56) References Cited

U.S. PATENT DOCUMENTS

| | | |
|---|---|---|
| 9,700,222 B2 | 7/2017 | Quinlan et al. |
| 9,704,908 B2 | 7/2017 | Graff et al. |
| 9,705,239 B2 | 7/2017 | Cheng et al. |
| 9,737,267 B2 | 8/2017 | Strom et al. |
| 9,750,418 B2 | 9/2017 | Millett et al. |
| 9,757,050 B2 | 9/2017 | Ghaffari et al. |
| 9,763,616 B2 | 9/2017 | Dugan |
| 9,770,179 B2 | 9/2017 | Etemad et al. |
| 9,782,095 B2 | 10/2017 | Ylostalo et al. |
| 9,795,313 B2 | 10/2017 | Kim et al. |
| 9,820,666 B2 | 11/2017 | Bokan et al. |
| 9,833,190 B2 | 12/2017 | Ghaffari et al. |
| 9,848,793 B2 | 12/2017 | Yoo et al. |
| 9,872,650 B2 | 1/2018 | Vice |
| 9,877,663 B2 | 1/2018 | Baker et al. |
| 9,894,757 B2 | 2/2018 | Arora et al. |
| 9,895,105 B2 | 2/2018 | Romem |
| 9,918,652 B2 | 3/2018 | Zeng et al. |
| 9,918,673 B2 | 3/2018 | Dugan |
| 9,943,245 B2 | 4/2018 | Gu et al. |
| 9,943,264 B2 | 4/2018 | Axelrod et al. |
| 9,949,691 B2 | 4/2018 | Huppert et al. |
| 9,974,456 B2 | 5/2018 | Yoshioka et al. |
| 9,974,458 B2 | 5/2018 | Zeng et al. |
| 9,974,461 B2 | 5/2018 | Shin et al. |
| 9,974,462 B2 | 5/2018 | Jayan et al. |
| 9,974,463 B2 | 5/2018 | Rutkove et al. |
| 9,980,659 B2 | 5/2018 | Sadeghian-Motahar et al. |
| 9,980,662 B2 | 5/2018 | Bibian et al. |
| 9,993,199 B2 | 6/2018 | Berzowska et al. |
| 9,999,391 B2 | 6/2018 | Kim et al. |
| 10,039,460 B2 | 8/2018 | Lang |
| 10,039,464 B2 | 8/2018 | Dubois et al. |
| 10,052,041 B2 | 8/2018 | Banet et al. |
| 10,070,799 B2 | 9/2018 | Ang et al. |
| 10,076,025 B2 | 9/2018 | Iwase |
| 10,076,278 B2 | 9/2018 | Wada et al. |
| 10,076,279 B2 | 9/2018 | Nahum |
| 10,092,211 B2 | 10/2018 | Brunner et al. |
| 10,143,396 B2 | 12/2018 | Chappell et al. |
| 10,159,422 B2 | 12/2018 | Baker et al. |
| 10,159,440 B2 | 12/2018 | Longinotti-buitoni et al. |
| 10,172,533 B2 | 1/2019 | Kulach et al. |
| 10,172,553 B2 | 1/2019 | Lee et al. |
| 10,182,723 B2 | 1/2019 | Evans et al. |
| 10,182,736 B2 | 1/2019 | Coleman et al. |
| 10,186,546 B2 | 1/2019 | De Graff et al. |
| 10,188,309 B2 | 1/2019 | Morun et al. |
| 10,188,353 B2 | 1/2019 | Stolen et al. |
| 10,192,044 B2 | 1/2019 | Choe et al. |
| 10,206,602 B2 | 2/2019 | Ren et al. |
| 10,244,986 B2 | 4/2019 | Adams et al. |
| 10,254,877 B2 | 4/2019 | Kim et al. |
| 10,264,968 B2 | 4/2019 | Gross |
| 10,265,514 B2 | 4/2019 | Harding et al. |
| 10,271,754 B2 | 4/2019 | Bahney et al. |
| 10,278,581 B2 | 5/2019 | Gaster |
| 10,285,617 B2 | 5/2019 | Toth et al. |
| 10,285,644 B2 | 5/2019 | Mazar et al. |
| 10,292,646 B2 | 5/2019 | Eom |
| 10,292,654 B2 | 5/2019 | Lee et al. |
| 10,299,690 B2 | 5/2019 | Choi et al. |
| 10,325,951 B2 | 6/2019 | Graff et al. |
| 10,335,087 B2 | 7/2019 | Lee et al. |
| 10,342,440 B2 | 7/2019 | Remes et al. |
| 10,349,860 B2 | 7/2019 | Rogers et al. |
| 10,349,888 B2 | 7/2019 | Muniz |
| 10,368,771 B2 | 8/2019 | Svojanovsky |
| 10,376,156 B2 | 8/2019 | Strauss et al. |
| 10,376,173 B2 | 8/2019 | George et al. |
| 10,383,219 B2 | 8/2019 | Arora et al. |
| 10,390,760 B2 | 8/2019 | Kube et al. |
| 10,401,241 B2 | 9/2019 | Madden et al. |
| 10,420,473 B2 | 9/2019 | Shi |
| 10,420,505 B2 | 9/2019 | Willis et al. |
| 10,426,401 B2 | 10/2019 | Bokan et al. |
| 10,433,756 B1 | 10/2019 | Bachelder et al. |
| 10,433,782 B2 | 10/2019 | Cobanoglu et al. |
| 10,449,672 B2 | 10/2019 | Assad et al. |
| 10,482,680 B2 | 11/2019 | Zeng et al. |
| 10,485,444 B2 | 11/2019 | Axelrod |
| 10,499,829 B2 | 12/2019 | Axelrod et al. |
| 10,506,948 B2 | 12/2019 | Wodlinger et al. |
| 10,512,414 B2 | 12/2019 | Axelrod et al. |
| 10,517,499 B2 | 12/2019 | Skrabal |
| 10,524,734 B2 | 1/2020 | Korzinov et al. |
| 10,531,813 B2 | 1/2020 | O'neill et al. |
| 10,542,897 B2 | 1/2020 | Gupta et al. |
| 10,548,484 B2 | 2/2020 | Brunner et al. |
| 10,548,496 B2 | 2/2020 | Gijsbers et al. |
| 10,548,500 B2 | 2/2020 | Lim et al. |
| 10,555,670 B2 | 2/2020 | Das et al. |
| 10,568,572 B2 | 2/2020 | Jovanovic et al. |
| 10,582,618 B2 | 3/2020 | Coleman et al. |
| 10,588,531 B2 | 3/2020 | Mahapatra |
| 10,595,772 B2 | 3/2020 | Burton |
| 10,602,940 B1 | 3/2020 | Muchhala et al. |
| 10,617,316 B2 | 4/2020 | Kang et al. |
| 10,617,354 B2 | 4/2020 | Berg et al. |
| 10,624,555 B2 | 4/2020 | Ashihara et al. |
| 10,631,748 B2 | 4/2020 | Felix et al. |
| 10,638,977 B2 | 5/2020 | Smink et al. |
| 10,702,176 B2 | 7/2020 | Agus et al. |
| 10,702,183 B2 | 7/2020 | Harrison |
| 10,713,800 B2 | 7/2020 | Raudins |
| 10,720,942 B2 | 7/2020 | Natarajan et al. |
| 10,729,345 B2 | 8/2020 | Lou et al. |
| 10,758,148 B2 | 9/2020 | Guger et al. |
| 10,772,522 B2 | 9/2020 | Zadig |
| 10,772,568 B2 | 9/2020 | Mhajna |
| 10,779,747 B2 | 9/2020 | Simon |
| 10,799,136 B2 | 10/2020 | Takagahara et al. |
| 10,799,180 B2 | 10/2020 | Gunasekar et al. |
| 10,799,708 B2 | 10/2020 | Intrator |
| 10,820,817 B2 | 11/2020 | Plenz et al. |
| 10,827,937 B2 | 11/2020 | Liu et al. |
| 10,835,146 B2 | 11/2020 | Francis et al. |
| 10,849,519 B2 | 12/2020 | Mendenhall et al. |
| 10,849,549 B2 | 12/2020 | Dugan |
| 10,869,391 B2 | 12/2020 | Kwon et al. |
| 10,874,318 B2 | 12/2020 | Shahdoostfard et al. |
| 10,877,715 B2 | 12/2020 | Billinghurst |
| 10,888,273 B2 | 1/2021 | Myers et al. |
| 10,893,822 B2 | 1/2021 | Hendler et al. |
| 10,898,099 B2 | 1/2021 | Coleman et al. |
| 10,912,480 B2 | 2/2021 | Sridhar et al. |
| 10,932,720 B2 | 3/2021 | Varadan |
| 10,939,839 B2 | 3/2021 | Baker et al. |
| 10,946,196 B2 | 3/2021 | Weisend |
| 10,966,649 B2 | 4/2021 | Fukuda |
| 10,973,452 B2 | 4/2021 | Fecteau et al. |
| 10,980,464 B2 | 4/2021 | Liao |
| 10,980,465 B2 | 4/2021 | Xu et al. |
| 11,006,838 B2 | 5/2021 | Coleman et al. |
| 11,006,839 B2 | 5/2021 | Tsuchimoto et al. |
| 11,006,841 B2 | 5/2021 | Wainwright et al. |
| 11,006,857 B2 | 5/2021 | Parker |
| 11,006,881 B2 | 5/2021 | Holder et al. |
| 11,006,887 B2 | 5/2021 | Urman et al. |
| 11,006,898 B2 | 5/2021 | Yamada et al. |
| 11,013,442 B2 | 5/2021 | Kim et al. |
| 11,033,197 B2 | 6/2021 | Woo |
| 11,039,776 B2 | 6/2021 | Wang et al. |
| 11,058,884 B2 | 7/2021 | Kim et al. |
| 11,064,949 B2 | 7/2021 | Bae et al. |
| 11,064,950 B2 | 7/2021 | Deriso |
| 11,076,763 B2 | 8/2021 | Atlas |
| 11,076,805 B2 | 8/2021 | Sayani et al. |
| 11,083,383 B1 | 8/2021 | Wu et al. |
| 11,083,399 B2 | 8/2021 | Spencer et al. |
| 11,083,401 B2 | 8/2021 | Sridhar et al. |
| 11,083,403 B1 | 8/2021 | Peters |
| 11,096,615 B2 | 8/2021 | Baumann et al. |
| 11,096,620 B1 | 8/2021 | Seidman et al. |

(56) References Cited

U.S. PATENT DOCUMENTS

| | | |
|---|---|---|
| 11,097,125 B2 | 8/2021 | Deckert et al. |
| 11,103,190 B2 | 8/2021 | Freeman et al. |
| 11,109,790 B2 | 9/2021 | Baek et al. |
| 11,109,792 B2 | 9/2021 | Bar-tal et al. |
| 11,123,001 B2 | 9/2021 | Nishimura et al. |
| 11,123,561 B2 | 9/2021 | Hernandez et al. |
| 11,138,792 B2 | 10/2021 | Wang et al. |
| 11,141,583 B2 | 10/2021 | Cronin et al. |
| 11,144,124 B2 | 10/2021 | Kang et al. |
| 11,147,492 B2 | 10/2021 | Maesani et al. |
| 11,147,501 B2 | 10/2021 | Xiang |
| 11,154,204 B2 | 10/2021 | Trapero Martin et al. |
| 11,154,228 B2 | 10/2021 | Cohen et al. |
| 11,160,504 B2 | 11/2021 | Yun et al. |
| 11,160,972 B2 | 11/2021 | Freeman et al. |
| 11,164,371 B2 | 11/2021 | Yellin et al. |
| 11,284,831 B2 | 3/2022 | Toth et al. |
| 11,432,759 B2 | 9/2022 | Devanaboyina |
| 11,826,157 B2 | 11/2023 | Axelrod |
| 11,826,170 B2 | 11/2023 | Navalgund et al. |
| 2002/0045836 A1 | 4/2002 | Alkawwas |
| 2003/0045804 A1 | 3/2003 | Brodnick |
| 2003/0050673 A1 | 3/2003 | Yamazaki et al. |
| 2003/0068914 A1 | 4/2003 | Merry et al. |
| 2003/0088167 A1 | 5/2003 | Fendrock et al. |
| 2003/0212319 A1 | 11/2003 | Magill |
| 2004/0073104 A1 | 4/2004 | Brun et al. |
| 2004/0167422 A1 | 8/2004 | Organ et al. |
| 2004/0236202 A1 | 11/2004 | Burton |
| 2004/0243015 A1 | 12/2004 | Smith et al. |
| 2005/0043640 A1 | 2/2005 | Chang |
| 2005/0119583 A1 | 6/2005 | Fuller et al. |
| 2005/0124901 A1 | 6/2005 | Misczynski et al. |
| 2005/0177038 A1 | 8/2005 | Kolpin et al. |
| 2005/0277822 A1 | 12/2005 | Manabe et al. |
| 2006/0047194 A1 | 3/2006 | Grigorov |
| 2006/0224072 A1* | 10/2006 | Shennib ............... A61B 5/6833 600/509 |
| 2007/0015984 A1 | 1/2007 | Yeo et al. |
| 2007/0027387 A1 | 2/2007 | Fendrock |
| 2007/0027388 A1 | 2/2007 | Chou et al. |
| 2007/0049814 A1 | 3/2007 | Muccio |
| 2007/0167859 A1 | 7/2007 | Finneran et al. |
| 2007/0225585 A1 | 9/2007 | Washbon et al. |
| 2008/0114232 A1 | 5/2008 | Gazit |
| 2008/0139953 A1 | 6/2008 | Baker et al. |
| 2008/0154110 A1 | 6/2008 | Burnes et al. |
| 2008/0183092 A1 | 7/2008 | Smith et al. |
| 2008/0221422 A1 | 9/2008 | Rantala |
| 2008/0249389 A1 | 10/2008 | Haug et al. |
| 2009/0036769 A1 | 2/2009 | Zdeblick |
| 2009/0084674 A1 | 4/2009 | Holzhacker et al. |
| 2009/0227856 A1 | 9/2009 | Russell et al. |
| 2009/0247835 A1 | 10/2009 | Voipio |
| 2009/0306485 A1 | 12/2009 | Bell |
| 2010/0063365 A1 | 3/2010 | Pisani et al. |
| 2010/0114272 A1 | 5/2010 | Haidarliu et al. |
| 2010/0137708 A1 | 6/2010 | Tamura et al. |
| 2010/0191074 A1 | 7/2010 | Chou |
| 2010/0191090 A1 | 7/2010 | Shin et al. |
| 2010/0234697 A1 | 9/2010 | Walter et al. |
| 2010/0234715 A1 | 9/2010 | Shin et al. |
| 2010/0261991 A1 | 10/2010 | Chen et al. |
| 2010/0271191 A1 | 10/2010 | de Graff et al. |
| 2011/0105874 A1 | 5/2011 | Feddes et al. |
| 2011/0270117 A1 | 11/2011 | Warwick et al. |
| 2011/0295096 A1 | 12/2011 | Bibian et al. |
| 2012/0035435 A1 | 2/2012 | Choi et al. |
| 2012/0139734 A1* | 6/2012 | Olde .................. H01R 11/22 600/372 |
| 2012/0143034 A1 | 6/2012 | Gaw et al. |
| 2012/0209102 A1 | 8/2012 | Ylotalo et al. |
| 2012/0302841 A1 | 11/2012 | Coressel et al. |
| 2012/0302843 A1 | 11/2012 | Otsubo et al. |
| 2013/0012799 A1 | 1/2013 | Sasaki et al. |
| 2013/0015841 A1* | 1/2013 | Caprio ............... A61B 5/282 324/126 |
| 2013/0035579 A1 | 2/2013 | Le et al. |
| 2013/0046165 A1 | 2/2013 | Cassidy et al. |
| 2013/0053674 A1 | 2/2013 | Volker |
| 2013/0066185 A1 | 3/2013 | Kerth et al. |
| 2013/0072870 A1 | 3/2013 | Heppe et al. |
| 2013/0102856 A1 | 4/2013 | Wolfberg |
| 2013/0123585 A1 | 5/2013 | Kang |
| 2013/0131460 A1 | 5/2013 | Yuen |
| 2013/0150698 A1 | 6/2013 | Hsu et al. |
| 2013/0184539 A1 | 7/2013 | Buchenrieder et al. |
| 2013/0190586 A1 | 7/2013 | Akingba et al. |
| 2013/0261420 A1 | 10/2013 | Kucherov et al. |
| 2013/0317318 A1 | 11/2013 | Tartz et al. |
| 2013/0338471 A1 | 12/2013 | Huang et al. |
| 2014/0094675 A1 | 4/2014 | Luna et al. |
| 2014/0094676 A1 | 4/2014 | Gani et al. |
| 2014/0107457 A1 | 4/2014 | Raghunathan |
| 2014/0107458 A1 | 4/2014 | Op De Beeck et al. |
| 2014/0121474 A1 | 5/2014 | Ciaccio |
| 2014/0148678 A1 | 5/2014 | Drori |
| 2014/0180029 A1 | 6/2014 | Hansmann et al. |
| 2014/0228662 A1 | 8/2014 | Park et al. |
| 2014/0275816 A1 | 9/2014 | Sandmore |
| 2014/0275829 A1 | 9/2014 | Berezhnyy et al. |
| 2014/0296682 A1 | 10/2014 | Wada et al. |
| 2014/0303459 A1 | 10/2014 | Wada et al. |
| 2014/0316217 A1 | 10/2014 | Purdon et al. |
| 2015/0025354 A1 | 1/2015 | Salonius et al. |
| 2015/0031964 A1 | 1/2015 | Bly et al. |
| 2015/0080695 A1 | 3/2015 | Rogers et al. |
| 2015/0157870 A1 | 6/2015 | Kalghatgi et al. |
| 2015/0231387 A1 | 8/2015 | Harding et al. |
| 2015/0248833 A1 | 9/2015 | Arne et al. |
| 2015/0250445 A1 | 9/2015 | Spiegel et al. |
| 2015/0272652 A1 | 10/2015 | Ghaffari et al. |
| 2015/0289822 A1 | 10/2015 | Dugan |
| 2015/0320515 A1 | 11/2015 | Edwards et al. |
| 2015/0351661 A1 | 12/2015 | Mezger et al. |
| 2015/0367122 A1 | 12/2015 | Morshed et al. |
| 2015/0374255 A1 | 12/2015 | Vasapollo |
| 2015/0374328 A1 | 12/2015 | Ginestet et al. |
| 2016/0007878 A1 | 1/2016 | Leuthardt et al. |
| 2016/0029917 A1 | 2/2016 | Baker et al. |
| 2016/0058335 A1 | 3/2016 | Ashby |
| 2016/0066812 A1 | 3/2016 | Cheng et al. |
| 2016/0081616 A1 | 3/2016 | Li |
| 2016/0128590 A1 | 5/2016 | Takizawa et al. |
| 2016/0128591 A1 | 5/2016 | Haraikawa et al. |
| 2016/0235323 A1 | 8/2016 | Tadi et al. |
| 2017/0035318 A1 | 2/2017 | Devanaboyina |
| 2017/0055871 A1 | 3/2017 | Axelrod et al. |
| 2017/0065200 A1* | 3/2017 | Gaw .................. A61B 5/274 |
| 2017/0079588 A1 | 3/2017 | Ghaffari et al. |
| 2017/0079589 A1 | 3/2017 | Ghaffari et al. |
| 2017/0086747 A1 | 3/2017 | Ghaffari et al. |
| 2017/0086748 A1 | 3/2017 | Ghaffari et al. |
| 2017/0086749 A1 | 3/2017 | Ghaffari et al. |
| 2017/0172439 A1 | 6/2017 | Zhu et al. |
| 2017/0172493 A1 | 6/2017 | Rahman et al. |
| 2017/0188942 A1 | 7/2017 | Ghaffari et al. |
| 2017/0231521 A1 | 8/2017 | Axelrod |
| 2017/0296079 A1 | 10/2017 | Torimitsu |
| 2017/0296088 A1 | 10/2017 | Choi |
| 2017/0303815 A1* | 10/2017 | De Limon ........... A61B 5/6831 |
| 2017/0340236 A1 | 11/2017 | Ghaffari et al. |
| 2017/0360329 A1 | 12/2017 | Derkx et al. |
| 2018/0078195 A1 | 3/2018 | Sutaria et al. |
| 2018/0116513 A1 | 5/2018 | Bhogu |
| 2018/0153462 A1 | 6/2018 | Borycka Kiciak et al. |
| 2018/0199849 A1 | 7/2018 | Axelrod et al. |
| 2018/0220950 A1* | 8/2018 | Cobanoglu ........... G08C 17/02 |
| 2018/0235502 A1 | 8/2018 | Nishimura et al. |
| 2018/0303405 A1 | 10/2018 | Dugan |
| 2018/0317800 A1 | 11/2018 | Coleman et al. |
| 2018/0333107 A1 | 11/2018 | García Sada et al. |
| 2019/0005397 A1 | 1/2019 | Coleman et al. |
| 2019/0015012 A1 | 1/2019 | Raudins et al. |

(56) References Cited

U.S. PATENT DOCUMENTS

| | | |
|---|---|---|
| 2019/0021659 A1 | 1/2019 | Sajwan et al. |
| 2019/0029595 A1 | 1/2019 | Sekitani et al. |
| 2019/0038170 A1* | 2/2019 | Baxi .................. A61B 5/0205 |
| 2019/0142299 A1 | 5/2019 | Holzhacker et al. |
| 2019/0142340 A1 | 5/2019 | Chang et al. |
| 2019/0175041 A1 | 6/2019 | Huang |
| 2019/0183713 A1 | 6/2019 | Sankai |
| 2019/0216352 A1 | 7/2019 | Sekitani et al. |
| 2019/0240476 A1 | 8/2019 | Harding et al. |
| 2019/0282112 A1 | 9/2019 | Jia et al. |
| 2019/0298203 A1 | 10/2019 | Yuen |
| 2019/0298219 A1 | 10/2019 | Woo et al. |
| 2019/0313910 A1 | 10/2019 | Vignon et al. |
| 2019/0328253 A1 | 10/2019 | Zhang |
| 2019/0328264 A1 | 10/2019 | Jeong |
| 2019/0328277 A1 | 10/2019 | Woo et al. |
| 2019/0350484 A1 | 11/2019 | Coleman et al. |
| 2019/0388030 A1 | 12/2019 | Colliou et al. |
| 2020/0000355 A1 | 1/2020 | Khair |
| 2020/0029840 A1 | 1/2020 | Nguyen et al. |
| 2020/0085336 A1 | 3/2020 | Lu et al. |
| 2020/0085339 A1 | 3/2020 | Axelrod |
| 2020/0107781 A1 | 4/2020 | Navalgund et al. |
| 2020/0138374 A1 | 5/2020 | Kitazawa et al. |
| 2020/0155022 A1 | 5/2020 | Zeng et al. |
| 2020/0163563 A1 | 5/2020 | Meyer et al. |
| 2020/0188676 A1 | 6/2020 | Lee et al. |
| 2020/0196875 A1 | 6/2020 | Huang |
| 2020/0205673 A1 | 7/2020 | Yi et al. |
| 2020/0205683 A1 | 7/2020 | Fujita et al. |
| 2020/0205747 A1 | 7/2020 | Mulligan et al. |
| 2020/0214632 A1 | 7/2020 | Neumann et al. |
| 2020/0230400 A1 | 7/2020 | Shepherd et al. |
| 2020/0237249 A1 | 7/2020 | Gunasekar et al. |
| 2020/0253535 A1 | 8/2020 | Rosen et al. |
| 2020/0297955 A1 | 9/2020 | Shouldice |
| 2020/0305713 A1 | 10/2020 | Sipe et al. |
| 2020/0305750 A1 | 10/2020 | Zhu |
| 2020/0315480 A1 | 10/2020 | Hwang |
| 2020/0337579 A1 | 10/2020 | Auerbach et al. |
| 2020/0375494 A1 | 12/2020 | Samuelsson |
| 2020/0383640 A1 | 12/2020 | Lee et al. |
| 2020/0405171 A1 | 12/2020 | Wei |
| 2021/0007623 A1 | 1/2021 | Sano et al. |
| 2021/0030292 A1 | 2/2021 | Dittmer et al. |
| 2021/0077010 A1 | 3/2021 | Dugan |
| 2021/0093246 A1 | 4/2021 | Dayeh et al. |
| 2021/0100510 A1 | 4/2021 | Myllykangas |
| 2021/0106268 A1 | 4/2021 | Kramer |
| 2021/0106270 A1 | 4/2021 | Birkill |
| 2021/0113837 A1 | 4/2021 | Sato et al. |
| 2021/0121095 A1 | 4/2021 | Sharawi et al. |
| 2021/0121114 A1 | 4/2021 | Fujita et al. |
| 2021/0121116 A1 | 4/2021 | Kreuzer et al. |
| 2021/0127999 A1 | 5/2021 | Govari et al. |
| 2021/0128042 A1 | 5/2021 | Herberger |
| 2021/0132125 A1 | 5/2021 | Hirano et al. |
| 2021/0153761 A1 | 5/2021 | Jung et al. |
| 2021/0169347 A1 | 6/2021 | Ito et al. |
| 2021/0169390 A1 | 6/2021 | Kim et al. |
| 2021/0177294 A1 | 6/2021 | Gliner et al. |
| 2021/0177332 A1 | 6/2021 | Tsukada et al. |
| 2021/0181002 A1 | 6/2021 | Huang et al. |
| 2021/0186403 A1 | 6/2021 | Epstein |
| 2021/0196178 A1 | 7/2021 | Choi et al. |
| 2021/0204855 A1 | 7/2021 | Choi et al. |
| 2021/0204879 A1 | 7/2021 | Gelfman et al. |
| 2021/0206345 A1 | 7/2021 | Nebuya |
| 2021/0219897 A1 | 7/2021 | Lee et al. |
| 2021/0220227 A1 | 7/2021 | Janssen et al. |
| 2021/0236034 A1 | 8/2021 | Sekitani et al. |
| 2021/0244304 A1 | 8/2021 | Park et al. |
| 2021/0244332 A1 | 8/2021 | Hagihara et al. |
| 2021/0251554 A1 | 8/2021 | Tal Fass |
| 2021/0251572 A1 | 8/2021 | Gill et al. |
| 2021/0259606 A1 | 8/2021 | Yeo et al. |
| 2021/0267524 A1 | 9/2021 | Moghaddambagheri |
| 2021/0275076 A1 | 9/2021 | Reed et al. |
| 2021/0275095 A1 | 9/2021 | Sarussi et al. |
| 2021/0275102 A1 | 9/2021 | Cho et al. |
| 2021/0282695 A1 | 9/2021 | Goldstein et al. |
| 2021/0282701 A1 | 9/2021 | Chan et al. |
| 2021/0282715 A1 | 9/2021 | Huang |
| 2021/0307665 A1 | 10/2021 | Hatakeyama et al. |
| 2021/0315485 A1 | 10/2021 | Matusik et al. |
| 2021/0321890 A1 | 10/2021 | Iyer et al. |
| 2021/0330232 A1 | 10/2021 | Oziat et al. |
| 2021/0338190 A1 | 11/2021 | Gopinathan et al. |
| 2022/0192580 A1 | 6/2022 | Toth et al. |
| 2022/0249022 A1 | 8/2022 | Toth et al. |
| 2024/0057928 A1 | 2/2024 | Axelrod |

FOREIGN PATENT DOCUMENTS

| | | |
|---|---|---|
| AT | 330539 T | 7/2006 |
| AU | 199536246 A | 4/1996 |
| AU | 2002329426 A1 | 4/2003 |
| AU | 2009346989 B2 | 8/2013 |
| AU | 2009267790 B2 | 9/2014 |
| AU | 2010251750 B2 | 4/2015 |
| AU | 2016205850 B2 | 10/2018 |
| AU | 2014414404 B2 | 11/2018 |
| AU | 2017444934 A1 | 8/2020 |
| AU | 2019204112 B2 | 7/2021 |
| AU | 2020232080 A1 | 10/2021 |
| AU | 2020246226 A1 | 10/2021 |
| AU | 2020249923 A1 | 10/2021 |
| BR | PI0604479 B1 | 4/2018 |
| CA | 2761561 A1 | 11/2010 |
| CA | 2763708 A1 | 12/2010 |
| CA | 2931480 A1 | 6/2015 |
| CA | 2943989 A1 | 10/2015 |
| CA | 2780747 C | 8/2020 |
| CN | 1130051 A | 9/1996 |
| CN | 1047512 C | 12/1999 |
| CN | 1233297 C | 12/2005 |
| CN | 1735375 A | 2/2006 |
| CN | 101214147 A | 7/2008 |
| CN | 101534706 A | 9/2009 |
| CN | 102008304 B | 5/2012 |
| CN | 101340847 B | 7/2012 |
| CN | 104736043 A | 6/2015 |
| CN | 204562159 U | 8/2015 |
| CN | 104939825 A | 9/2015 |
| CN | 204744167 U | 11/2015 |
| CN | 204744169 U | 11/2015 |
| CN | 103987413 B | 9/2016 |
| CN | 102525450 B | 12/2016 |
| CN | 106214122 A | 12/2016 |
| CN | 106232000 A | 12/2016 |
| CN | 104545899 B | 1/2017 |
| CN | 104523263 B | 6/2017 |
| CN | 106999100 A | 8/2017 |
| CN | 206729877 U | 12/2017 |
| CN | 104720801 B | 2/2018 |
| CN | 107693001 A | 2/2018 |
| CN | 107847150 A | 3/2018 |
| CN | 105796094 B | 7/2018 |
| CN | 105943021 B | 9/2018 |
| CN | 109044328 A | 12/2018 |
| CN | 105992564 B | 4/2019 |
| CN | 209285452 U | 8/2019 |
| CN | 106232000 B | 11/2019 |
| CN | 210095722 U | 2/2020 |
| CN | 107411740 B | 1/2021 |
| CN | 107495929 B | 2/2021 |
| CN | 109431493 B | 2/2021 |
| CN | 110151170 B | 2/2021 |
| CN | 110367978 B | 2/2021 |
| CN | 111006801 B | 2/2021 |
| CN | 110840454 B | 3/2021 |
| CN | 110916655 B | 3/2021 |
| CN | 110393522 B | 4/2021 |
| CN | 110946721 B | 4/2021 |

(56) References Cited

FOREIGN PATENT DOCUMENTS

| | | | |
|---|---|---|---|
| CN | 111184508 B | 5/2021 |
| CN | 109157202 B | 6/2021 |
| CN | 112220483 B | 6/2021 |
| CN | 112656418 B | 6/2021 |
| CN | 111329476 B | 7/2021 |
| CN | 111513709 B | 8/2021 |
| CN | 111588373 B | 8/2021 |
| CN | 111543949 B | 9/2021 |
| CN | 112205986 B | 9/2021 |
| CN | 112426161 B | 9/2021 |
| CN | 112535483 B | 9/2021 |
| CN | 214128577 U | 9/2021 |
| CN | 111973172 B | 10/2021 |
| DE | 3523987 A1 | 1/1987 |
| DE | 69525388 | 3/2002 |
| DE | 60212666 T2 | 5/2007 |
| DE | 102011113839 B4 | 5/2013 |
| DE | 112012003250 T5 | 4/2014 |
| DE | 112012004146 T5 | 11/2014 |
| DE | 102007036243 B4 | 4/2016 |
| EP | 0687442 A1 | 12/1995 |
| EP | 1053572 B1 | 5/2003 |
| EP | 1432349 B1 | 6/2006 |
| EP | 1941830 A2 | 7/2008 |
| EP | 1962680 A1 | 9/2008 |
| EP | 1649805 B1 | 11/2009 |
| EP | 1700564 A3 | 9/2010 |
| EP | 1653851 B1 | 1/2011 |
| EP | 2434950 A1 | 4/2012 |
| EP | 2385914 A4 | 10/2012 |
| EP | 2465415 B1 | 7/2013 |
| EP | 2356680 B1 | 4/2015 |
| EP | 1942799 B1 | 8/2015 |
| EP | 2717768 B1 | 10/2015 |
| EP | 2404171 A4 | 1/2016 |
| EP | 2758094 B1 | 3/2016 |
| EP | 2830494 B1 | 4/2016 |
| EP | 2432548 B1 | 8/2016 |
| EP | 2914165 B1 | 8/2017 |
| EP | 3073948 A4 | 8/2017 |
| EP | 2579770 B1 | 9/2017 |
| EP | 3122250 A4 | 11/2017 |
| EP | 2378956 A4 | 12/2017 |
| EP | 2386117 A4 | 12/2017 |
| EP | 3254615 A1 | 12/2017 |
| EP | 3273847 A1 | 1/2018 |
| EP | 3190957 A4 | 7/2018 |
| EP | 2352421 B1 | 10/2018 |
| EP | 2986206 B1 | 12/2018 |
| EP | 3048967 B1 | 2/2019 |
| EP | 3365666 A4 | 5/2019 |
| EP | 2349440 B1 | 8/2019 |
| EP | 2713863 B1 | 1/2020 |
| EP | 3324843 B1 | 1/2020 |
| EP | 3457933 A4 | 1/2020 |
| EP | 3606411 A1 | 2/2020 |
| EP | 2902293 B1 | 3/2020 |
| EP | 2902294 B1 | 3/2020 |
| EP | 3626158 A1 | 3/2020 |
| EP | 2081488 B1 | 5/2020 |
| EP | 3229665 B1 | 5/2020 |
| EP | 3235428 B1 | 7/2020 |
| EP | 3692907 A1 | 8/2020 |
| EP | 3705035 A1 | 9/2020 |
| EP | 3453322 B1 | 11/2020 |
| EP | 3131453 B1 | 1/2021 |
| EP | 3302261 B1 | 1/2021 |
| EP | 3758582 A1 | 1/2021 |
| EP | 2547252 B1 | 6/2021 |
| EP | 3846686 A1 | 7/2021 |
| EP | 3772360 B1 | 8/2021 |
| EP | 3868287 A1 | 8/2021 |
| EP | 3880069 A1 | 9/2021 |
| EP | 3880070 A1 | 9/2021 |
| EP | 3883457 A1 | 9/2021 |
| EP | 3888539 A1 | 10/2021 |
| EP | 3900622 A1 | 10/2021 |
| EP | 3902465 A1 | 11/2021 |
| ES | 2262834 T3 | 12/2006 |
| ES | 2645646 T3 | 12/2017 |
| GB | 200123772 | 11/2001 |
| HK | 1161421 A1 | 8/2012 |
| HK | 1208612 A1 | 3/2016 |
| HK | 1210829 A1 | 5/2016 |
| HK | 1248090 A1 | 10/2018 |
| IN | 200502327 P2 | 7/2007 |
| IN | 200704398 P2 | 2/2008 |
| IN | 200802368 P1 | 7/2008 |
| IN | 201500914 P3 | 4/2015 |
| IT | 2008 | 12/2009 |
| JP | 3235632 B2 | 12/2001 |
| JP | 2005503883 A | 2/2005 |
| JP | 2012515436 A | 7/2012 |
| JP | 5124881 B2 | 11/2012 |
| JP | 5646492 B2 | 11/2014 |
| JP | 5689066 B2 | 2/2015 |
| JP | 5694947 B2 | 2/2015 |
| JP | 5830012 B2 | 10/2015 |
| JP | 2015532841 A | 11/2015 |
| JP | 2016006880 A | 1/2016 |
| JP | 5933773 B2 | 5/2016 |
| JP | 6014178 B2 | 9/2016 |
| JP | 6018157 B2 | 10/2016 |
| JP | 2016539698 A | 12/2016 |
| JP | 2017035505 A | 2/2017 |
| JP | 6109863 B2 | 3/2017 |
| JP | 2017148514 A | 8/2017 |
| JP | 6277130 B2 | 1/2018 |
| JP | 6320920 B2 | 4/2018 |
| JP | 2018520813 A | 8/2018 |
| JP | 6411423 B2 | 10/2018 |
| JP | 2018174335 A | 11/2018 |
| JP | WO2020550304 A | 9/2021 |
| KR | 2016090877 A | 8/2016 |
| MY | 129068 A | 3/2007 |
| NL | 2014897 B1 | 2/2017 |
| RU | 2006116780 A | 12/2007 |
| RU | 2355304 C1 | 5/2009 |
| RU | 2428111 C2 | 9/2011 |
| SE | 199403321 | 9/1994 |
| SE | 199403344 A | 3/1996 |
| TW | 568770 B | 1/2004 |
| WO | 9610358 A1 | 4/1996 |
| WO | 02062217 A1 | 8/2002 |
| WO | 03028550 A3 | 5/2003 |
| WO | 2004073518 A1 | 9/2004 |
| WO | 2007070997 A1 | 6/2007 |
| WO | 2008057884 A3 | 7/2008 |
| WO | 2010042653 A1 | 4/2010 |
| WO | 2010042957 A3 | 7/2010 |
| WO | 2010056857 A3 | 7/2010 |
| WO | 2010082993 A2 | 7/2010 |
| WO | 2010082993 A3 | 9/2010 |
| WO | 2010081137 A3 | 11/2010 |
| WO | 2010132923 A1 | 11/2010 |
| WO | 2010136837 A1 | 12/2010 |
| WO | 2010102310 A3 | 1/2011 |
| WO | 2011149753 A1 | 12/2011 |
| WO | 2012073761 A1 | 6/2012 |
| WO | 2012060874 A3 | 7/2012 |
| WO | 2012167096 A3 | 1/2013 |
| WO | 2013022853 A1 | 2/2013 |
| WO | 2013041174 A1 | 3/2013 |
| WO | 2013052919 A3 | 5/2013 |
| WO | 2014039404 A1 | 3/2014 |
| WO | 2015080991 A1 | 6/2015 |
| WO | 2015123255 A1 | 8/2015 |
| WO | 2015148018 A1 | 10/2015 |
| WO | 2016061589 A1 | 4/2016 |
| WO | 2016200087 A1 | 12/2016 |
| WO | 2017017260 A1 | 2/2017 |
| WO | 2017070700 A1 | 4/2017 |
| WO | WO-2017201538 A1 * | 11/2017 | ........... A61B 5/0008 |
| WO | 2018201629 A1 | 11/2018 |

(56) References Cited

FOREIGN PATENT DOCUMENTS

| | | |
|---|---|---|
| WO | 2019198828 A1 | 10/2019 |
| WO | 2019241753 A1 | 12/2019 |
| WO | 2020057448 A1 | 3/2020 |
| WO | 2020075481 A1 | 4/2020 |
| WO | 2020101333 A1 | 5/2020 |
| WO | 2020142562 A1 | 7/2020 |
| WO | 2020152429 A1 | 7/2020 |
| WO | 2020176508 A1 | 9/2020 |
| WO | 2020184249 A1 | 9/2020 |
| WO | 2020184346 A1 | 9/2020 |
| WO | 2020210693 A1 | 10/2020 |
| WO | 2020228724 A1 | 11/2020 |
| WO | 2020255142 A2 | 12/2020 |
| WO | 2020257367 A1 | 12/2020 |
| WO | 2020257836 A1 | 12/2020 |
| WO | 2021009488 A1 | 1/2021 |
| WO | 2021014116 A1 | 1/2021 |
| WO | 2021024212 A2 | 2/2021 |
| WO | 2021029452 A1 | 2/2021 |
| WO | 2021033863 A1 | 2/2021 |
| WO | 2021052754 A1 | 3/2021 |
| WO | 2021065580 A1 | 4/2021 |
| WO | 2021066077 A1 | 4/2021 |
| WO | 2021076054 A1 | 4/2021 |
| WO | 2021080157 A2 | 4/2021 |
| WO | 2021090195 A1 | 5/2021 |
| WO | 2021097202 A1 | 5/2021 |
| WO | 2021106948 A1 | 6/2021 |
| WO | 2021107310 A1 | 6/2021 |
| WO | 2021113804 A1 | 6/2021 |
| WO | 2021124795 A1 | 6/2021 |
| WO | 2021130683 A1 | 7/2021 |
| WO | 2021140441 A1 | 7/2021 |
| WO | 2021143538 A1 | 7/2021 |
| WO | 2021148716 A1 | 7/2021 |
| WO | 2021157287 A1 | 8/2021 |
| WO | 2021157296 A1 | 8/2021 |
| WO | 2021166495 A1 | 8/2021 |
| WO | 2021172839 A1 | 9/2021 |
| WO | 2021177171 A1 | 9/2021 |
| WO | 2021189108 A1 | 9/2021 |
| WO | 2021194888 A1 | 9/2021 |
| WO | 2021195332 A1 | 9/2021 |
| WO | 2021199042 A1 | 10/2021 |
| WO | 2021199824 A1 | 10/2021 |
| WO | 2021199825 A1 | 10/2021 |
| WO | 2021199827 A1 | 10/2021 |
| WO | 2021200245 A1 | 10/2021 |
| WO | 2021200575 A1 | 10/2021 |
| WO | 2021200765 A1 | 10/2021 |
| WO | 2021200859 A1 | 10/2021 |
| WO | 2021201697 A1 | 10/2021 |
| WO | 2021204939 A1 | 10/2021 |
| WO | 2021205976 A1 | 10/2021 |
| WO | 2021207633 A2 | 10/2021 |
| WO | 2021214435 A1 | 10/2021 |
| WO | 2021216847 A1 | 10/2021 |

\* cited by examiner

ELECTRODE PATCH AND CONNECTION SYSTEM

CROSS-REFERENCES TO RELATED APPLICATIONS

The present application is a Continuation of U.S. patent application Ser. No. 17/788,070 filed Jun. 22, 2022; which is a U.S. National Stage application of PCT/IB2020/062369 filed Dec. 23, 2020; which claims priority to New Zealand Application Nos. 760518 filed Dec. 23, 2019 and 769806 filed Nov. 11, 2020; the full disclosures which are incorporated herein by reference in their entirety for all purposes.

BACKGROUND OF THE INVENTION

The invention relates to an electrode patch and connection system. Especially, but not exclusively, the invention relates to an electrode patch suitable for use in monitoring gastrointestinal electrical activity and connection system for such electrode patch.

Gastric dysrhythmias underlie or contribute to diseases including gastroparesis, chronic nausea and vomiting, functional dyspepsia, and gastro-esophageal reflux disease (GERD). Gastroparesis is a condition in which the stomach typically fails to empty properly after a meal, leading to symptoms of early fullness, bloating, pain, nausea, vomiting and malnutrition and possibly death in severe cases. Medical guidelines suggest that the majority of patients with suspected gastroparesis should receive an upper gastrointestinal (GI) endoscopy study (a video-guided examination of the inside of the stomach). Chronic unexplained nausea and vomiting has a similar presentation to gastroparesis, however, gastric emptying testing is normal. Functional dyspepsia is a condition characterized by symptoms of 'chronic indigestion' lasting at least weeks to months. Functional dyspepsia is further divided in epigastric pain syndrome characterized by pain or burning sensations in the upper abdomen, and post-prandial distress syndrome characterized by early satiety and post-prandial fullness. Other symptoms of functional dyspepsia may include bloating, nausea, and pain after eating. The causes of functional dyspepsia are not well understood, however dysrhythmic gastric activity has been clearly implicated, with up to 60% of adult dyspeptic patients showing abnormal gastric electrical activity in some studies. Delayed gastric emptying occurs in 25-40% of functional dyspepsia. Upper GI endoscopy is a standard diagnostic tool for assessing patients presenting with dyspepsia to exclude other pathologies. Delayed gastric emptying also affects a significant sub-population of patients with GERD, and gastric dysrhythmia has been implicated. Gastric electrical activity may also become disorganized following gastric surgeries, causing delayed gastric emptying and/or symptoms such as those described above.

Peristaltic activity in the GI tract is coordinated by a propagating electrical activity termed slow waves. GI slow waves are initiated and spread via networks of interstitial cells of Cajal (ICCs), which are coupled to the smooth muscle layers in the GI tract wall. In the human stomach, slow waves originate at a pacemaker site high on the greater curvature and propagate toward the antrum at a normal frequency of approximately three cycles per minute.

Electrocardiograma routine diagnostic test for cardiac dysrhythmias, in which electrodes are placed on the skin to record the distant organ electrical activity. Electrogastrography (EGG) is the assessment of GI electrical activity through a small number of skin electrodes placed on the abdominal surface. EGG has been proposed as a diagnostic test for stomach disorders but despite research efforts has failed to meet clinical expectations. A key reason for the failure of EGG to diagnose gastric dysfunction reliably is that the test relied on measures of frequency and power, whereas modern spatial high-resolution mapping technologies have shown that gastric dysrhythmias often occur at frequencies that are in the normal range. Many abnormalities may therefore be missed by EGG. Recent studies have shown that is necessary to map a spatial pattern of electrical activity in the stomach to reliably differentiate and classify gastric electrical abnormalities. EGG was a summation of the electrical activity occurring in the stomach and could provide accurate information regarding the normal or abnormal propagation of the individual slow wave cycles. Another reason why EGG is unreliable is that GI electrical signals are of very low signal strength, and noise could be mistaken for signals. In addition, because it used only a small number of electrodes, EGG electrodes often did not directly overlying the stomach in many patients, meaning that gastric signals were unlikely to be retrieved.

A SQUID (Super Quantum Interference Device) can be used to measure the magnetic fields associated with GI electrical activity, but is a multi-million dollar device that must also be housed in a magnetically-shielded room, and analysis of the signals obtained is complex and has not yet been reliably achieved. Also, the resolution achieved via a SQUID may be suboptimal.

A roving electrode placed into sequential sites on the mucosa of the stomach, or a small number of electrodes linearly arranged and attached to a naso-gastric tube, can give some indication of GI dysrhythmic activity, however may not reliably provide information on the spatial propagation of gastric slow wave activity and therefore cannot describe abnormal velocities, propagation directions, or dysrhythmias accurately. Intubating the stomach is also a relatively invasive way to measure gastric dysfunction, and may require sedative medications or may be poorly tolerated in some patients. In addition, these measures can only made in the fasted state, and patients often only experience symptoms after eating.

High-resolution mapping of GI electrical activity by measurement at the serosal surface requires invasive surgical access and therefore is not appropriate for clinical use in the vast majority of patients with gastrointestinal symptoms.

Inserting a catheter or similar device inside a body of a subject at minimally invasive surgery or by endoscopy can be difficult often requiring highly skilled medical practitioners to carry out the test. Further such invasive test can cause discomfort to the subject and expose the subject to the risks of infections or other complications, which is obviously not desirable. Some patients may require time to fully recover after performing invasive tests. Further, it is generally necessary to visit hospital, clinic or similar facility to perform such invasive tests which can be inconvenient and expensive.

Prior art systems and scientific research articles attempted to achieve non-invasive monitoring of GI activity, such as by using arrays of skin surface electrodes.

For example, WO 2017201538 discloses devices, system and methods for monitoring physiological functions from surface electrophysiological sensors. It discloses a device that includes electrophysiological sensors structures to include an array of electrodes that are spatially arranged on a substrate and is operable to acquire electrophysiological signals to obtain series data. It discloses use of data processing unit to process spatially resolved time-series data based on the electrophysiological signals to determine wave propagation parameters.

Similarly, U.S. Pat. No. 9,474,482 discloses apparatus and method for diagnosing motility disorders of a GI tracts of a body. It discloses measuring electrical signals from the GI tract while the patient is engaged in normal daily activities, recording measured signals on a portable electronic device carried by the body, recording by the patient in real time one or more symptoms of the body and analyzing characteristics of the recorded electrical signals with the recorded symptoms of the body for diagnosis of GI disorders of the body.

However, conventional/previously known apparatuses do not provide features for allowing simple yet reliable coupling between an electrode patch and connector device e.g. a portable electronic device (e.g. data acquisition device) that is worn by a user. If a mechanism for connection between the electrode patch and such connector device is not reliable or proper/robust, then accidental disconnection between the electrode patch and connector device is highly likely in which case the system will defeat the purpose of allowing the real-time electrophysiological monitoring. Further, such previously known apparatus fails to provide features that allow the apparatus to be worn comfortably by a subject while the subject is engaged in normal daily activities. Further, due to its weight, the connector device can easily disconnect/dislodge from the electrode patch and can even detach and fall from the body of the subject which can not only damage the connector device but can also cause confusion, dissatisfaction, and poor treatment compliance. The conventional devices fail to address this problem.

Furthermore, for monitoring GI electrical activity, the electrodes may be required to be placed on the abdominal surface as close to the gastrointestinal organ of interest due to low signal amplitude. Since, the skin on abdominal surface generally experiences large deformations from normal bodily movements, the electrode patch may need to be embedded in a conformal material that can adequately deform with the skin. If rigid electrodes or non-conformal materials are used, the electrode patch or electrodes are likely to delaminate from the skin resulting to unreliable signal quality. The conventional/previously known apparatus fail to address or sufficiently address this problem.

Also, skewing of electrode patch when attached to the connector device can cause failed connections and cross talks.

Further, conventional electrode patches do not focus on designs to allowing optimal packaging of the contact pads of the electrode patch within a minimum area, which means conventional electrode patches can be bulkier an uncomfortable to wear especially on abdominal regions.

Providing the minimum width of the electrical conductors that is needed for screen printing, and at the same time providing a suitable physical layout of getting all electrodes to meet at a common connector portion(s) for connecting with a connector of a connector device can be difficult which means conventional electrode patches are bulkier.

Conventional/previously known connector apparatus may require cables or wires for connecting the electrode patch to the connector device. Cables involving a large number of electrodes can be cumbersome to wear, difficult or expensive to manufacture, are a common failure point, and further reduce the wearability of the electrophysiological monitoring device.

Object of the Invention. It is an object of the present invention to provide an electrode patch which overcomes or at least partially ameliorates some of the abovementioned limitations and risks or which at least provides the public with a useful choice.

Alternatively, or additionally, it is an object of the present invention to provide a connection system for an electrode patch which overcomes or at least partially ameliorates some of the abovementioned limitations and risks or which at least provides the public with a useful choice.

BRIEF SUMMARY OF THE INVENTION

In a first aspect, the present invention resides in an electrode patch for monitoring electrical activity generated by a subject, the electrode patch comprising: a plurality of spatially arranged electrodes for contacting an outer surface of a skin of the subject to sense and measure electrical potentials at multiple electrodes; and at least one connector portion for connecting to a connector of a connector device, the at least one connector portion being spaced apart at a distance from the electrodes and is electrically connected with the electrodes through electrical conductors running as conductive tracks between the electrodes and said at least one connector portion.

In one embodiment, at least one tongue is formed on the electrode patch extending from rest of the electrode patch, and wherein said at least one connector portion is located at said at least one tongue.

In some embodiments, the at least one tongue is co-planar with rest of the electrode patch.

In some embodiments, the electrode patch is flexible and stretchable.

In some embodiments, the electrode patch comprises a flexible substrate and the electrodes are spatially arranged on the flexible substrate.

In some embodiments, the flexible substrate is stretchable.

In some embodiments, the flexible substrate comprises or is made of a Thermoplastic Polyurethane (TPU) film.

In some embodiments, said at least one connector portion is electrically connected with the electrodes through electrical conductors running as conductive tracks (or conductive traces) between the electrodes and said at least one connector portion.

In some embodiments, a hydrogel is placed on top of the flexible substrate.

In some embodiments, said electric conductors are arranged on said flexible substrate.

In some embodiments, said at least one connector portion comprises a plurality of electrically conductive contact pads.

In some embodiments, said plurality of electrically conductive contact pads is in a staggered pattern.

In some embodiments, each of the contact pads is substantially square in shape.

In some embodiments, said contact pads are electrically connected to said electrodes through said electric conductors.

In some embodiments, in the electrode patch, total number of said contact pads is same as total number of said electrodes.

In some embodiments, in the electrode patch, total number of said contact pads is same as total number of said electrodes and total number of electric conductors.

In some embodiments, in the electrode patch, total number of said contact pads is greater than total number of said electrodes.

In some embodiments, the electrode patch comprises at least one cut-out.

In some embodiment, said at least one cut-out is located at said at least one tongue.

In some embodiments, said at least one cut-out is substantially rectangular in shape.

In some embodiments, said at least one cut-out is located between the two connector portions.

In some embodiments, the electrode patch comprises two connector portions that are spaced apart from each other and from the electrodes.

In some embodiments, the two connector portions are located on the same side of the electrode patch and on a same tongue.

In some embodiments, the two connector portions are a first connector portion and a second connector portion wherein a fixed number of the electrodes are electrically connected to the first connector portion and a fixed number of electrodes are electrically connected to the second connector portion.

In some embodiments, half of the fixed number of electrodes are electrically connected to the first connector portion and remaining half of the fixed number of electrodes of the electrode patch are electrically connected to the second connector portion.

In some embodiments, the array of electrodes contains 64 electrodes arranged in 8 rows and 8 columns.

In some embodiments, the array of electrodes contains more than or less than 64 electrodes.

In some embodiment, the array of electrodes contains 32 electrodes.

In some embodiments, the 32 electrodes are arranged in 8 rows and 4 columns.

In some embodiments, the 32 electrodes are arranged in 4 rows and 8 columns.

In some embodiments, the electrode patch is polygonal in shape.

In some embodiments, the electrode patch comprises a primary region and said at least one tongue is formed on the electrode patch extending from the primary region, said at least one tongue being co-planar with the primary region.

In some embodiments, the primary region is substantially rectangular in shape.

In some embodiments, the electrodes are located in the primary region.

In some embodiments, at least one intermediate portion is located between said at least one tongue and the primary region, the at least one intermediate portion being narrower than said at least one tongue and the primary region.

In some embodiments, said at least one tongue is substantially rectangular in shape. In some embodiments, the electrode patch has rounded corners to prevent curling.

In some embodiments, two tongues are formed on the patch extending from rest of the patch, said two tongues being co-planar with each other and with rest of the patch, the two tongue being a first tongue and a second tongue.

In some embodiments, said connector portion or connector portions are located either in one or both of the first or second tongues.

In some embodiment, the first tongue and the second tongue are located on two opposite sides of the primary region.

In some embodiments, the first tongue is substantially rectangular in shape.

In some embodiments, the second tongue is substantially rectangular in shape.

In some embodiments, the at least one intermediate portion is substantially trapezoidal in shape.

In some embodiments, the electrode patch comprises an adhesive for allowing the electrode patch to attach to the outer surface of the skin of the subject.

In some embodiments, the adhesive is located at the edges of the electrode patch.

In some embodiments, the adhesive is located at the edges of the primary region and at said at least one tongue.

In some embodiments, the adhesive that is located at said at least one tongue is spaced apart from said at least one connection portion.

In some embodiments, the adhesive is formed as an adhesive layer.

In some embodiment, the electrode patch comprises a plurality of alignment holes at or near the at least one connector portion.

In some embodiments, the electrode patch comprises a plurality of alignment holes surrounding the or each one of the at least one connector portion.

In some embodiments, the electrode patch is a single use electrode patch.

In some embodiments, the electrode patch is for use in monitoring gastro-intestinal electrical activity of the subject.

In some embodiments, the electrode patch is for use in monitoring colonic electrical activity of the subject.

In some embodiments, the subject is a pediatric patient.

In some embodiments, the electrode patch comprises a planar surface, wherein at least the portion of each of the electrodes, the connector portion and the electrical conductors are exposed at the planar surface.

In some embodiments, the planar surface is the surface that is configured to contact the outer surface of the skin of the subject.

In some embodiments, the planar surface is a substantially flat surface.

In some embodiments, the electrode patch is formed as a single sheet of material or as a substantially panel.

In some embodiments, the electrode patch is of a polygonal shape.

In some embodiments, the electrode patch extends between a first end and a second end that is located opposite the first end, wherein the electrodes are located more proximal to the first end than the second end and the connector portion is located more proximal to the second end that the first end.

In some embodiments, the electrodes are spaced apart from the connector portion at a distance that is at least a quarter of the total distance between the first end and the second end.

In some embodiment, the connector portion is spaced apart at a distance of at least 5 centimetres from each of the electrodes.

In a second aspect, the invention resides in a connector device comprising or in a form of a first clamping member and a second clamping member that are configured to move between a clamped position in which the first and second clamping members are configured to clamp an electrode patch or at least a portion of an electrode patch to allow physical and operative connection between the connector device and the electrode patch, and a released position in which the first and second clamping members are configured move away from the clamped position to allow the electrode patch or the portion of the electrode patch to be released from the connector device.

In some embodiments, the first and second clamping members are configured to exert a pressure on the electrode patch or the portion of the electrode patch when in the clamped position.

In some embodiments, in the clamped position the first clamping member moves towards the second clamping member and in the released position the first clamping member moves away from the second clamping member.

In some embodiments, the first and second clamping members are magnetic clamping members.

In some embodiments, at least one of the first and second clamping members comprises at least one connector that is configured to be physically and operatively connected with the electrode patch or the portion of the electrode patch for receiving the electrical signals from multiple electrodes of the electrode patch to allow monitoring the electrical activity generated by the subject.

In some embodiments, the at least one connector is an array connector or array connectors.

In some embodiments, said at least at least one connector is an interposer or interposers.

In some embodiments, the connector device comprises a main body having a planar surface onto which the electrode patch or the portion of the electrode patch is configured to be placed, the main body comprising a first end portion and a second end portion that are located opposite to each other, wherein the first clamping member is mounted to the main body at or near the first end portion, and the second clamping member is the main body, wherein in the clamped position the first clamping member is configured to move towards the planar surface of the main body and in the release position the first clamping member is configured to move away from the planar surface of the main body.

In some embodiments, the first clamping member is hingedly mounted to the main body.

In some embodiments, the first clamping members comprises the at least one connector.

In some embodiments, the first clamping member is configured to move between an open position and a closed position wherein in the open position, said at least one connector of the first clamping member is exposed to ambient and in the closed position, said at least one connector of the first clamping member is concealed from the ambient.

In some embodiments, in the clamped position, the first clamping member is configured to pivotally move towards the planar surface of the main body and at least partially conceal at least a portion of the planar surface of the main body.

In some embodiments, the connector device comprises a main body having a planar surface onto which the electrode patch or the portion of the electrode patch is configured to be placed, the main body comprising a first end portion and a second end portion that are located opposite to each other, wherein the first clamping member is mounted to the main body at or near the first end portion, and the second clamping member is mounted to the main body at or near the second end portion, wherein in the clamped position the first and second clamping members are each configured to move towards the planar surface and in the release position the first and second clamping members are each configured to move away from the planar surface.

In some embodiments, the first and second clamping members are hingedly mounted to the main body.

In some embodiments the first and second clamping members each comprise the at least one connector.

In some embodiments, the first and second clamping members are configured to move between an open position and a closed position wherein in the open position, said at least one connector of each of the first and second clamping members is exposed to ambient and in the closed position, said at least one connector in each of the first and second clamping members is concealed from the ambient.

In some embodiments, the connector device comprises at least one alignment feature that is configured to align and/or retain the electrode patch or the portion of the electrode patch onto the connector device.

In some embodiments, the connector device comprises at least one alignment feature that is configured to align and/or retain the electrode patch or the portion of the electrode patch onto the connector device, and wherein the at least one alignment feature is located on or substantially on the planar surface between the first end portion and the second end portion.

In some embodiments, the at least one alignment feature is located on or substantially on the planar surface between the first end portion and the second end portion.

In some embodiments, the at least one alignment feature is a protrusion that is configured to be received by at least one complementary cut-out formed in the electrode patch.

In some embodiments, the protrusion is located at or near the centre of the first end portion and the second end portion.

In some embodiments, the protrusion is substantially rectangular or cuboid in shape.

In some embodiments, the protrusion is of a size that is sufficient to prevent at least a lateral movement of the electrode patch between the first end portion and the second end portion when the protrusion is received by the at least one complementary cut-out formed in the electrode patch.

In some embodiments, the connector device further comprises a plurality of alignment pins that are configured to be received by complementary alignment holes formed in the electrode patch.

In some embodiments, the alignment pins are located on either or both sides of the protrusion.

In some embodiments, there are six alignment pins located on either or each of the both sides of the protrusion.

In some embodiments, in the clamped position, the first clamping member and the second clamping member are both configured to pivotally move towards the planar surface and at least partially conceal the planar surface save for the protrusion.

In some embodiments, in the clamped position, at least a portion of the protrusion is exposed to the ambient.

In some embodiment, the portion of the protrusion that is exposed to the ambient comprises a display screen.

In some embodiments, the connector device is a portable electronic device.

In some embodiments, the connector device is a data acquisition device.

In some embodiments, the connector device is a data logging device.

In some embodiments, the connector device is a wearable electronic device and at least the main body, the first clamping member, and the second clamping member together form a housing inside which electronic components of the connector device are at least partially disposed.

In some embodiments, the connector device is battery powered.

In some embodiments, the connector device is powered by a Li-ion battery.

In some embodiments, the electronic device comprises an electronic circuit and a memory with the instructions stored in the memory, wherein implementation of the instructions causes the electronic device to receive signals from the electrode patch, process the signals, and transmit data to a remote computing device to allow monitoring of electrical activity generated by the subject.

In some embodiments, the connector device comprises at least one analogue to digital convertor to amplify and digitize a biopotential measurements signals received from the electrode patch.

In some embodiments, the at least one analogue to digital convertor is an analogue to digital convertor chip.

In some embodiments, the connector device comprises a microcontroller configured to receive signals from the analogue to digital convertor, process the signals, and transmit data to a remote computing device to allow monitoring of electrical activity generated by the subject.

In some embodiments, the at least one analogue to digital convertor is electrically connected to the microcontroller with a flexible cable.

In some embodiments, the electronic device further comprises a flash memory, Near Field Connection (NFC) module(s) and/or charging circuit(s).

In some embodiments, the connector device is part of a connector system comprising a docking device having a connector device receiving compartment that is configured to receive the connector device.

In some embodiments, the docking device is a wireless charging device for facilitating wireless charging of the connector device when the connector device is received within the connector device receiving compartment.

In some embodiments, the electrode patch is part of the connector system.

In some embodiments, the connector device comprises a biasing member that is configured to bias at least one of the first and second clamping members to move towards a direction of the electrode patch.

In some embodiments, the biasing member is a leaf spring.

In a third aspect, the invention resides in a connector device comprising: a main body extending from a first end portion to a second end portion, the second end portion being located opposite the first end portion, the main body having a top surface and a bottom surface, the top surface being configured to receive an electrode patch or at least a portion of an electrode patch having multiple electrodes for use in monitoring electrical activity generated by a subject; at least one clamping member that is mounted to the main body; wherein, the at least one clamping member is configured to move between an open position and a closed position, wherein in the open position the at least one clamping member is configured to move away from the top surface and at least partially reveal the top surface, and in the closed position the at least one clamping member is configured to move towards the top surface and at least partially conceal the top surface; wherein the at least one clamping member comprises at least one connector that is configured to be physically and operatively connected with the electrode patch or the portion of the electrode patch for receiving the electrical signals from multiple electrodes to allow monitoring the electrical activity generated by the subject.

In some embodiments, the at least one clamping member is hingedly mounted to the main body.

In some embodiments, both of the first and second clamping members comprise the at least one connector.

In some embodiments, the at least one clamping member is configured to move between an open position and a closed position wherein in the open position, said at least one connector of the at least one clamping member is exposed to ambient and in the closed position, said at least one connector in the at least one clamping members is concealed from the ambient.

In some embodiments, the at least one connector is an array connector or array connectors.

In some embodiments, said at least at least one connector is an interposer or interposers.

In some embodiments, in the closed position, the at least one clamping member is configured to pivotally move towards the top surface and at least partially conceal the top surface.

In some embodiments, the connector device is a wearable electronic device and at least the main body and the at least one clamping member, together form a housing inside which electronic components of the connector device are at least partially disposed.

In some embodiments, the connector device comprises at least one alignment feature that is configured to align and/or retain the electrode patch or the portion of the electrode patch onto the top surface.

In some embodiments, the at least one alignment feature is located on or substantially on the top surface.

In some embodiment, the at least one alignment feature is a protrusion that is configured to be received by at least one complementary cut-out formed in the electrode patch.

In some embodiments, the protrusion is located at or near the centre of the first end portion and the second end portion.

In some embodiments, the protrusion is substantially rectangular or cuboid in shape.

In some embodiments, the protrusion is of a size that is sufficient to prevent at least a lateral movement of the electrode patch between the first end portion and the second end portion when the protrusion is received by the at least one complementary cut-out formed in the electrode patch.

In some embodiment, the connector device further comprises a plurality of alignment pins that are configured to be received by complementary alignment holes formed in the electrode patch.

In some embodiment, the alignment pins are located on either or both sides of the protrusion.

In some embodiments, there are six alignment pins located on each side of the protrusion.

In some embodiments, in the closed position, the at least one clamping member is configured to pivotally move towards the top surface and at least partially conceal the top surface save for the protrusion.

In some embodiments, the at least two clamping members are mounted to the main body, the at least two clamping members being a first clamping member and a second clamping member.

In some embodiments, the first and second clamping members are configured to move between the open position and the closed position, wherein when in the open position the first clamping member and the second clamping member are both configured to move towards the top surface and at least partially conceal the top surface; and wherein at least one of the first and second clamping members comprises the at least one connector that is configured to be physically and operatively connected with the electrode patch or the portion of the electrode patch for receiving the electrical signals from multiple electrodes to allow monitoring the electrical activity generated by the subject.

In some embodiments, the first and second clamping members are configured to move between an open position and a closed position wherein in the open position, said at least one connector of each of the first and second clamping members is exposed to ambient and in the closed position, said at least one connector in each of the first and second clamping members is concealed from the ambient.

In some embodiments, the at least one alignment feature is located on or substantially on the top surface, between the first end portion and the second end portion.

In some embodiments, in the closed position, the first clamping member and second clamping member are both configured to pivotally move towards the top surface and at least partially conceal the top surface save for the protrusion.

In some embodiments, the connector device is a wearable electronic device and at least the main body, the first clamping member, and the second clamping member together form a housing inside which electronic components of the connector device are at least partially disposed.

In some embodiments, the connector device is battery powered.

In some embodiments, the connector device is powered by a Li-ion battery.

In some embodiments, the connector device comprises an electronic circuit and a memory with the instructions stored in the memory, wherein implementation of the instructions causes the electronic device to receive signals from the electrode patch, process the signals, and transmit data to a remote computing device to allow monitoring of electrical activity generated by the subject.

In some embodiments, the connector device is a data acquisition device.

In some embodiments, the connector device is a data logging device.

In some embodiments, the connector device is part of a connector system comprising a docking device having a compartment that is configured to receive the connector device.

In some embodiments, the docking device is a wireless or contact charging device for facilitating wireless or charging of the connector device when the connector device is received within the connector device receiving compartment.

In some embodiments, the connector device comprises at least one analogue to digital convertor to amplify and digitize a biopotential measurements signals received from the electrode patch.

In some embodiments, the at least one analogue to digital convertor is an analogue to digital convertor chip.

In some embodiments, the connector device comprises a microcontroller configured to receive signals from the analogue to digital convertor, process the signals, and transmit data to a remote computing device to allow monitoring of electrical activity generated by the subject.

In some embodiments, the at least one analogue to digital convertor is electrically connected to the microcontroller with a flexible cable.

In some embodiments, the electronic component further comprises a flash memory, Near Field Connection (NFC) module(s) and/or charging circuit(s).

In some embodiments, the electrode patch is part of the connector system.

In some embodiments, the electrode patch is the one as defined in the first aspect.

In a fourth aspect, the invention broadly resides in a system for monitoring electrical activity generated by a subject, the system comprising: an electrode patch comprising spatially arranged electrodes for contacting an outer surface of a skin of the subject to sense and measure electrical potentials at multiple electrodes, wherein the electrodes are routed to at least one connector portion that is spaced apart from the electrodes and is electrically connected with the electrodes through electrical conductors running as conductive tracks between the electrodes and said at least one connector portion; and a connector device having at least one connector that is configured to be physically and operatively connected with the electrode patch or at least a portion of the electrode patch at said at least one connector portion for receiving the electrical signals from multiple electrodes to allow monitoring electrical activity generated by the subject.

In some embodiments, the connector device is an electronic device.

In some embodiments, the connector device comprises an electronic circuit and a memory with the instructions stored in the memory, wherein implementation of the instructions causes the electronic device to receive signals from the electrode patch, process the signals, and transmit data to a remote computing device to allow monitoring of electrical activity generated by the subject.

In some embodiments, the connector device is a data acquisition device.

In some embodiments, the connector device is a data logging device.

In some embodiments, the system further comprises a docking device having a compartment that is configured to receive the connector device.

In some embodiments, the electrode patch is the one as defined in the first aspect.

In some embodiments, the connector device is the one as defined in the second or third aspect.

In some embodiments, the system is for monitoring gastro-intestinal electrical activity.

In some embodiments, the electrode patch is the one as defined in the first aspect.

In a fifth aspect, the invention broadly resides in a method of connecting an electrode patch to a connector device, the method comprising: providing an electrode patch; providing a connector device having a first and second clamping member that are configured to clamp the electrode patch or at least a portion of the electrode patch; moving the first and second clamping member between a clamped position in which the first and second clamping members are configured to clamp the electrode patch or the portion of the electrode patch to allow physical and operative connection between the connector device and the electrode patch or the portion of the electrode patch, and a released position in which the first and second clamping members are configured move away from the clamped position to the electrode patch or the portion of the electrode patch to be released from the connector device.

In some embodiments, the electrode patch comprises at least one cut-out, and the connector device comprises at least one complementary protrusion that is configured to be received by the cut-out, wherein the method further comprises: positioning the electrode patch or the portion of the electrode patch on the connector device during the release position so that the at least one protrusion is received by said at least one cut-out; and moving the first and second clamping members from the release position to the clamped position.

In some embodiments, the electrode patch comprises a plurality of alignment holes, and the connector device comprises a plurality of complementary alignment pins configured to be received by the alignment holes, wherein the method further comprises: positioning the electrode patch or the portion of the electrode patch on the connector device during the release position so that the plurality of alignment pins is received by the plurality of alignment holes; and moving the first and second clamping members from the release position to the clamped position.

In some embodiments, the electrode patch is the one as defined in the first aspect.

In some embodiments, the connector device is the one as defined in the second or third aspect.

Other aspects of the invention may become apparent from the following description which is given by way of example only and with reference to the accompanying drawings.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations, except where expressly specified to the contrary. It is also to be understood that the specific devices illustrated in the attached drawings and described in the following description are simply exemplary embodiments of the invention. Hence, specific dimensions and other physical characteristics related to the embodiments disclosed herein are not to be considered as limiting.

It is acknowledged that the term "comprise" may, under varying jurisdictions, be attributed with either an exclusive or an inclusive meaning. For the purpose of this specification, and unless otherwise noted, the term 'comprise' shall have an inclusive meaning, allowing for inclusion of not only the listed components or elements, but also other non-specified components or elements. The terms 'comprises' or 'comprised' or 'comprising' have a similar meaning when used in relation to the system or to one or more steps in a method or process.

As used hereinbefore and hereinafter, the term "and/or" means "and" or "or", or both.

As used hereinbefore and hereinafter, "(s)" following a noun means the plural and/or singular forms of the noun.

When used in the claims and unless stated otherwise, the word 'for' is to be interpreted to mean only 'suitable for', and not for example, specifically 'adapted' or 'configured' for the purpose that is stated.

BRIEF DESCRIPTION OF THE DRAWINGS

Preferred embodiments of the invention will be described by way of example only and with reference to the drawings, in which.

DETAILED DESCRIPTION OF THE INVENTION

Conventional medical apparatus for monitoring electrical activity may use sensing device comprising an electrode patch and a connector device which could be an electronic device such as a data acquisition device that is in electronic communication with such patch. However, such conventional apparatus does not focus on coupling mechanism for the electrode patch and the connector device to ensure that the connections between the two are reliable and proper. If such connections are not proper, then accidental disconnection between the connector device and the electrode patch is highly likely in which case real-time monitoring of physiological/electrical activity cannot be performed. Further, due to its weight, the connector device can easily disconnect from the electrode patch and detach and fall from the body of the subject which can not only damage the connector device but can also cause confusion, dissatisfaction, and poor compliance. Therefore, it is desirable to provide an electrode patch connection system that allows simple but reliable coupling between an electrode patch and connector device that may be worn by the subject. Also, it is desirable to provide an electrode patch connection system for a non-invasive medical apparatus that can be worn by a subject to monitor the physiological condition in a comfortable and reliable manner, while the subject is engaged in normal daily activities. Also, it is desirable to provide electrode patch connect system that can be easily set easy set up and used by new patients having minimal or no experience of using any system for monitoring physiological functions. Further, it is desirable to provide electrode patch connection system that do not require cables for connection between electrode patch and the connector of a connector device.

It is also desirable to have an electrode patch that does not skew when connected to the connector device can cause failed connections and cross talks.

It is also desirable to have an electrode patch that is designed to allow optimal packaging of the contact pads of the electrode patch within a minimum area so that the design of an electrode patch that is less bulky and more comfortable to wear especially on abdominal regions can be achieved.

It is also desirable to have an electrode patch that is simple in design and cost-effective to manufacture by screen printing.

It is also desirable to have an electrode patch that requires use no or less wires during use so that there no or less tangling or wires.

It is also desirable to have an electrode patch that feels comfortable to the subject when connected to an outer surface of a skin of the subject during use.

Having a connector device and electrode patch assembly that do not easily dislodge when connected to outer surface of a skin of a patient/subject is also desirable.

Figure 1:
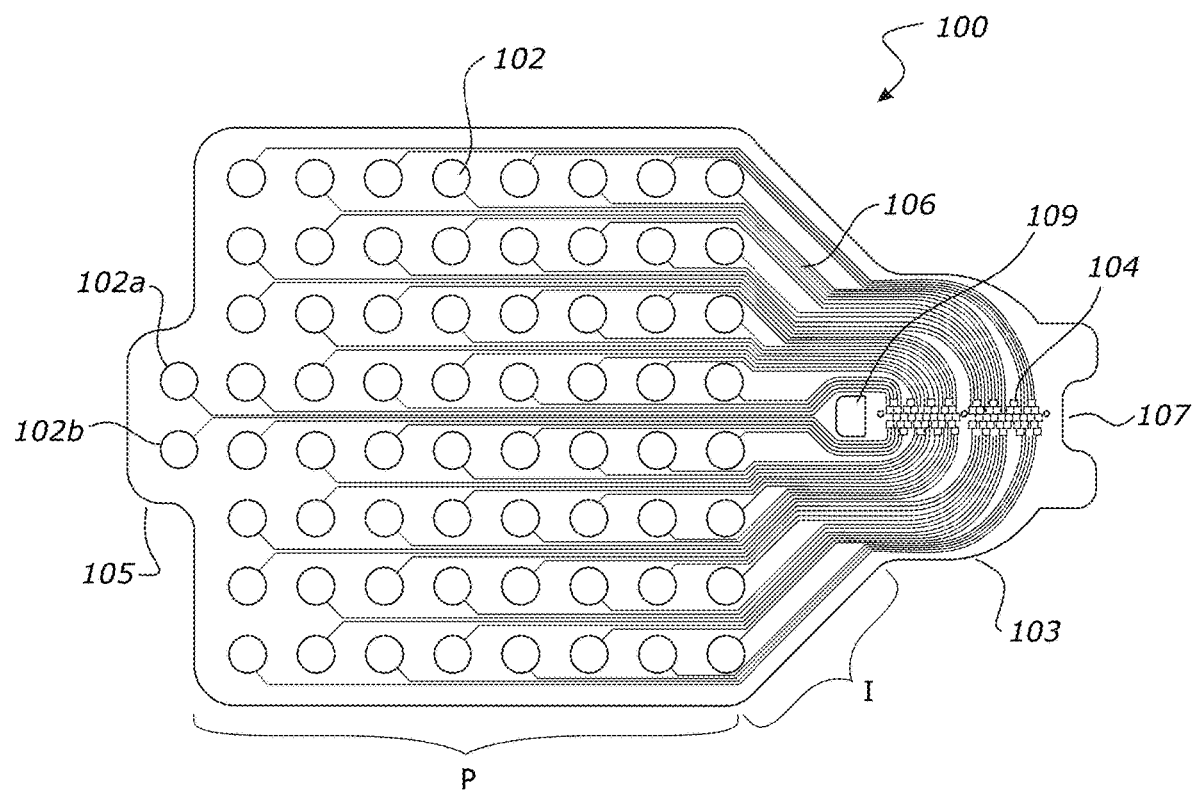
FIG. 1 is an example/embodiment of an electrode patch according to a first preferred embodiment of the present invention.

Reference will now be made to the accompanying drawings in which FIG. 1 shows one example of electrode patch 100 according to one preferred embodiment of the invention.

The electrode patch 100 is configured to be used as part of a system for monitoring physiological functions on a subject. The subject is preferably a human but optionally the subject may be a non-human animal. Most preferably, the electrode patch 100 is configured to be used as part of a system for monitoring gastro-intestinal (GI) electrical activity of a subject. In some embodiments, the electrode patch 100 may be configured to monitor electrical/physiological activity on other regions of the subject such as but not limited to colonic regions, and/or monitoring cardiac or other smooth muscle systems such as uterus or bladder, or of brain signals (EEG) or skeletal muscle signals (EMG).

The electrode patch 100 is basically a sensing device and comprises a plurality of spatially arranged surface electrophysiological sensors in the form of electrodes for contacting an outer surface of the skin of the subject to sense and measure electrical potentials at multiple electrodes. In the example shown in FIG. 1, there are total of 66 electrodes out of which 64 electrodes are arranged in an array of 8 rows and 8 columns and the remain two electrodes 102*a*, 102*b* are the ground and reference electrodes. In use electrical potentials may be measured as the difference between each of the 64 electrodes and the reference electrode 102*a*. The ground electrode 102*a* may be the "driven right leg" or "bias" electrode. The purpose of the ground electrode 102*a* is to keep voltage level of the subject's body within an acceptable range and to minimize any common-mode in the subject's body (e.g., 50/60 Hz power-line noise). The driven right leg will act as a source or sink as necessary (within reason) to accomplish this. However, the electrode patch 100 may comprise more than 66 electrodes or less than 66 electrodes. The ground and reference electrodes 102*a*, 102*b* may be different than what is shown in FIG. 1.

Preferably, the electrode patch 100 is configured to be removably attached to the outer surface of the skin of the subject, most preferably at or near an abdominal region, so that the electrodes 102, 102*a*, 102*b* can contact the outer surface of the skin of the subject at or near the abdominal region to sense and measure electrical signals from the GI tract of the subject. If the electrode patch 100 is for sensing and measuring electrical signals from other regions, then the electrode patch may be configured to be removably attached to the outer surface of the skin of the subject at or near at suitable regions, so that the electrodes 102, 102*a*, 102*b* can contact the outer surface of the skin of the subject at or near such region to sense and measure electrical signals from the that region of subject's body. This may include a colonic region.

The electrode patch 100 may be made out of a flexible and stretchable material. The electrode patch 100 may comprise a flexible substrate and the electrodes may be spatially arranged on the flexible substrate. The flexible substrate may also be stretchable. By being flexible and stretchable, the electrode patch 100 can properly adhere to the skin of the subject which can result in improved electrode impedance. In order to monitor the electrical activity, for example a GI electrical activity, the electrodes may be required to be placed on the abdominal surface as close to the gastrointestinal organ of interest due to low signal amplitude. Since, the skin of the subject on the abdominal surface generally experiences large deformations from normal bodily movements, the electrode spatially arranged in a conformal/flexible substrate can adequately deform with the and consequently reduce the chances of delaminating from the skin of the subject. By reducing the chances of delaminating from the skin of the subject, chances of unreliable signal quality are also minimized.

The flexible substrate may comprise or may be made of a Thermoplastic Polyurethane (TPU) film which may be a thin adhesive film/layer. A hydrogel may be placed on top of the flexible substrate and that improve conductivity of the biological signals.

As shown in FIG. 1, the electrode patch may comprise at least one connector portion 104. The connector portion 104 may be spaced apart at a distance from the electrodes 102, 102a, 102b. The connector portion 104 is not any of the electrodes 102, 102a, 102b. The connector portion 104 may be spaced apart from the primary region P of the electrode patch containing electrodes 102, 102a, 102b and the connector portion 104 is electrically connected with the electrodes 102, 102a, 102b. As shown, the primary region P may substantially rectangular as shown. Alternatively, the primary region P may be of any other suitable polygonal shape. In certain embodiments, the primary region P may be circular in shape. As shown, the electrode patch 100 may extend between a first end and a second end that is located opposite the first end. The electrodes 102, 102a, 102b may be located more proximal to the first end than the second end and the connector portion is located more proximal to the second end that the first end. In certain embodiments, the electrodes 102, 102a, 102b may be spaced apart from the connector portion 104 at a distance that is at least a quarter of the total distance between the first end and the second end. The electrode patch 100 may be spaced apart at a distance of at least 5 centimetres from each of the electrodes 102, 102a, 102b.

By having the connector portion 104 that is spaced apart from the electrodes at a distance, any connector device that is attached to the connector portion 104 may also be located at a distance from the electrodes. This can minimize the interference with the electrodes and/or contact between the electrodes 102, 102a, 102b and the outer surface of the skin of the subject, during the physical interaction with the connector device and/or any physical interaction at the connector portion 104.

The electrode patch 100 may comprise/have a planar surface and at least a portion of each of the electrodes 102, 102a, 102b, the connector portion 104 and the electrical conductors 106 may be exposed at the planar surface. The planar surface may be the surface that is configured to contact the outer surface of a skin of the subject. The planar surface may be a substantially flat surface. The electrode patch 100 may be formed as a single sheet of material or as a substantially panel. Such planar surface arrangement enhances the comfort and provides better adherence to the skin of the subject during use as there are no bulges in the skin contact region of the electrode patch nor are there any components of the electrode patch 100 that are protruding in the skin contact region of the electrode patch. At least one tongue 103 may be formed on the electrode patch 100 extending from rest of the electrode patch 100. The tongue 103 may be co-planar with rest of the electrode patch 100. The connector portion 104 may be located in the tongue 103 but in one embodiment could be located near/proximal to the tongue. Having a connector portion 104 on a tongue 103 which is narrower than the primary region facilitates easy and better connection between the electrode patch 100. This also means a smaller connector device can be used to connect to connector portion 104 of the electrode patch 100 and clamp the electrode patch as opposed to large connector device that would be necessary if the connector portion 104 was located in other wide areas of the electrode patch 100. Therefore, having a tongue 103 and connector portion 104 located on the tongue reduces the volume and potentially also the weight of the overall apparatus (i.e. apparatus containing the connector device and electrode patch) that to be worn by the subject during use. As shown an intermediate region I may be formed between the primary region P and the tongue 103. The intermediate region I may be substantially trapezoidal in shape.

As shown, the electrode patch 100 may comprise a second tongue 105 and the ground and reference electrodes 102a, 102b may be located on that second tongue 105. As shown, the end of the tongue 103 that is furthest (most distal) from the electrodes 102 (and further from the primary region P) is formed as a C-shaped portion 107. As shown, a cut-out 109 may be located between the electrodes 102 and the connector portion 104. As shown, the second tongue 105 may be substantially rectangular in shape.

The connector portion 104 may be arranged on the flexible substrate. As shown in FIG. 1, the connector portion 104 may be electrically connected with the electrodes 102, 102A, 102B through electrical conductors 106 running as conductive tracks (which may also be referred to as conductive traces) between the electrodes 102 and the connector portion 104, the electric conductors 106 may be conductive tracks. In one embodiment, it may be wires. Conductive track is advantageous over less preferred embodiment that may use wires. For example, mass production can be achieved at lower cost by using conductive tracks as opposed to using wires. Further, conductive tracks provide low electric noise as compared to wires. Additionally, wires can move and therefore can tangle or dislodge easily whereas conductive tracks are fixed to the electrode patch and hence are immune to such undesirable movement and tangling. Therefore, conductive tracks bring better reliability in the performance of the electrode patch. Furthermore, use of conductive tracks as opposed to wires can avoid bulges or similar in the surface of the electrode patch that is configured to be in contact with the outside skin (outer surface of the skin) of the subject thereby providing comfort during use. The electric conductors 106 may be arranged on the flexible substrate.

Figure 2:
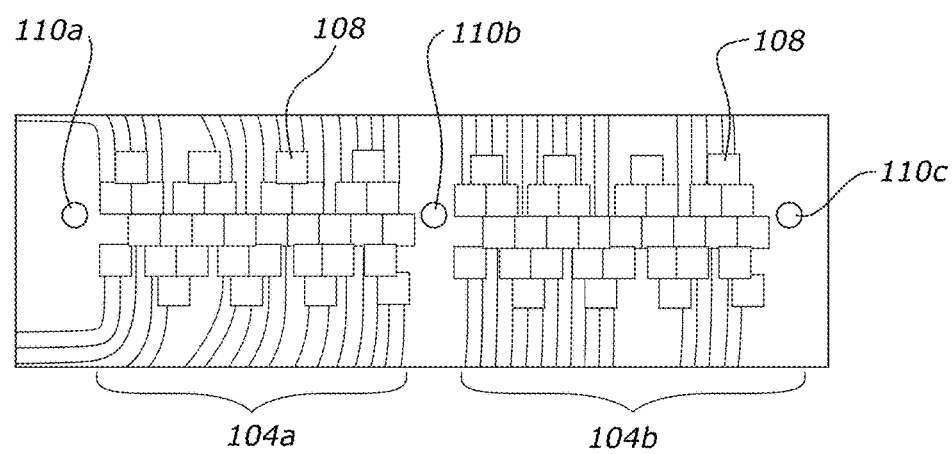
FIG. 2 shows a connection portion of the electrode patch of FIG. 1.

As shown in FIG. 2, the connector portion 104 may comprise a plurality of electrically conductive contact pads 108. The contact pads 108 may be arranged on the flexible substrate. The contact pads 108 may be electrically connected to the electrodes through the electric conductors 106. As shown in FIG. 1, the electrical conductors 106 may run as conductive tracks between the electrodes 102 and the contact pads 108.

In the electrode patch 100, total number of said contact pads 108 may be same as total number of electrodes 102. In the example shown in FIG. 1, there are 66 electrodes and 66 contact pads 108 in the electrode patch 108. The electrodes 102 and the contact pads 108 may be connected in such a manner that one electrode is electrically connected with only one contact pad and no two electrodes are electrically connected with the same contact pad. As shown in FIG. 1, both reference and ground electrodes 102a, 102b can be separate from the array of electrodes 102.

In some embodiments, the total number of contact pads 108 may be greater than the total number of electrodes 102. Having such additional/spare contact pad(s) can be advantageous as they can be used for many purposes. As one example, the spare contact pad(s) may be used for detecting the version or model of connector device used with the electrode patch. For example, if the spare contact pad(s) connect(s) to the connector of the contact device when such connection was not expected, then that may imply to the user that incorrect version or model of the connector device is used. Similarly, if the spare contact pad(s) does/do not connect to the connector of the contact device when such connection was expected, then that may imply to the user that incorrect version or model of the connector device is used. User may receive error message or some other mechanism that may trigger them to use the correct version of the connector device.

Each of the electrodes 102, 102A, 102B and contact pads 108 may be electrically connected as using electrical conductors 106 in such a manner that one electrode is electrically connected with only one electric contact pad 108 using only one electric conductor and no electric conductor electrically connects more than one pair of electrode and contact pad that are electrically connected with each other.

In the patch, total number of electrical conductors 106 be same as total number of said electrodes 102, 102a, 102b. As shown in FIG. 1, in patch 100 there are sixty-six electrical conductors 106.

The electrodes 102, 102a, 102b may be Ag—AgCl electrodes.

Each of the electrodes 102, 102a, 102b may be at least 2 cm apart from each other. The maximum length of the patch may be 21 cm. The maximum width of the patch may be 16 cm. In certain embodiments, the width of the patch may be more or less than 21 cm.

The electrode patch 100 may comprise an adhesive which may be formed as an adhesive layer. The electrode patch 100 may be a single-use peel-and-stick patch. As shown, the corners of electrode patch 100 may be rounded to prevent curling.

The electrode patch 100 may be mass produced using screen printing. For the design of the patch of FIG. 1, one of the major challenges is to provide the minimum width of the electrical conductors 106 that is needed for screen printing, and at the same time providing a suitable physical layout of getting all electrodes, in this example all sixty-six electrodes, to meet at the connector portion 104 for connecting with a connector of a connector device. Each contact pad 108 also requires a certain flat surface area to operate effectively and reliably. The electrode patch 100 of the invention can achieve this by configuring groups of contact pads 108 in a staggered format/pattern as shown in FIG. 2. Preferably each of the contact pads 108 are square in shape as shown to maximize the x/y tolerance required to make electrical contact with the connector device. Alternatively, the contact pads 108 may be rectangular in shape. As shown in FIG. 1, the electrical conductors 106 on the electrode patch 100 may run into the contact pads 108 at staggered spatial intervals and travel/run in curves. The configuration as described above allows an optimal packaging of the contact pads 108 within a minimum area. Such configuration also allows connector portion 104 to effectively and efficiently connect with a connector 150 of a connector device such as a connector device 600 shown in FIG. 5.

Figure 3:
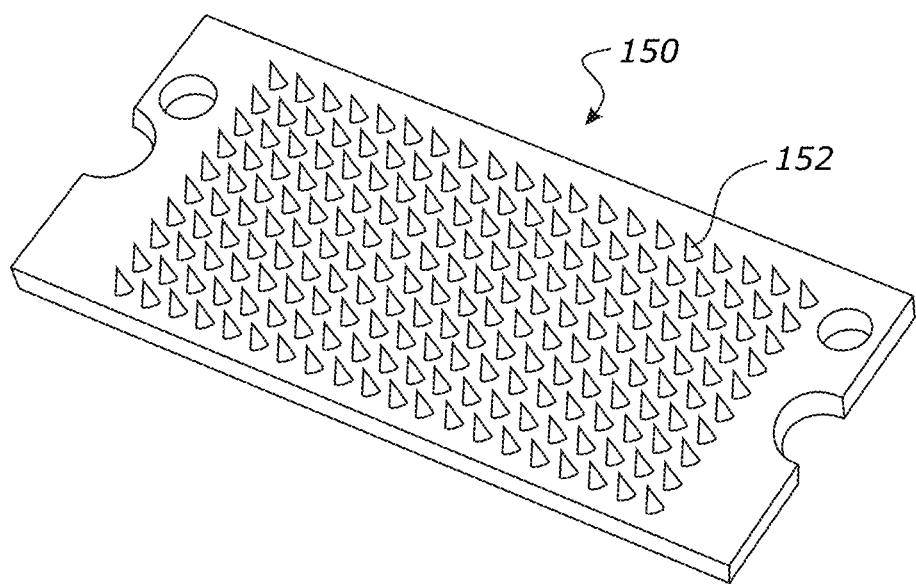
FIG. 3 shows an example of a connector that can be used for connecting to the electrode patch of FIG. 1.
Figure 4:
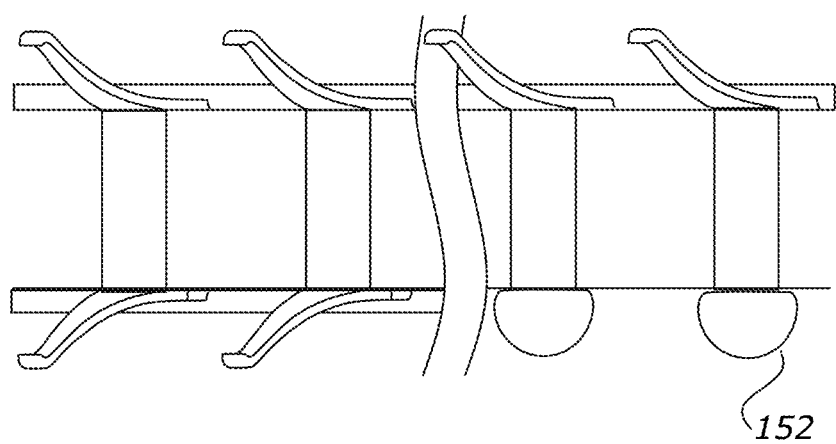
FIG. 4 shows a cross-sectional view of the connector of FIG. 3.

One example of a connector 150 that can be used to electrically connect with the contact pads 108 of the electrode patch 100 is shown in FIG. 3. The connector 150 may comprises a plurality of conductive contact pins 152 that are configured to be electrically connected to the contact pads 108 of the connector portion 104 during use. The connector 150 may be an interposer or array connector and the contact pins 152 may be in the form of solder balls as shown in FIG. 4. Such connector 150 may work by compression and may require cumulative contact force that can increase by the number of contact pins 152 that are used. By using such connector 150 no cable may be required for connecting the connector portion 104 (and consequently the electrodes) to the connector device, such as connector device 500 as described below with reference to FIG. 5. One example of the connector 150 that may be used is a 1.0 mm Ultra Low Power Micro Array connector. An example of such connector is disclosed in https://www.samtec.com/products/za8, the entirety of which is herein incorporated by reference. By using connectors such as connector 150, cables/wires are not required for electrically connecting the connector 150 and the electrode patch 100.

Figure 5:
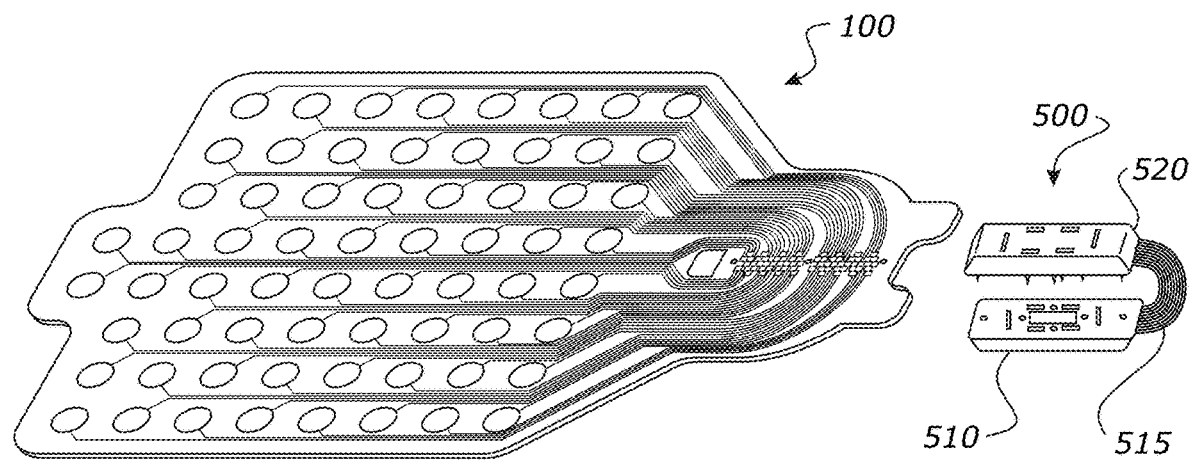
FIG. 5 shows an example/embodiment of a connector device according to a first preferred embodiment of the present invention that is configured to be connected to the electrode patch of FIG. 1.

FIG. 5 shows one embodiment of a connector device 500 for clamping the electrode patch 100 or at least the portion thereof. Such clamping may exert a pressure on the electrode patch or the portion of the electrode patch when in the clamped position. As shown, the connector device 500 may be in a form of two separate connecting or clamping members, namely a first clamping member 510 which in this example is a lower clamping member and a second clamping member 520 which in this example is an upper clamping member. The first clamping member 510 and the second clamping member 520 are configured to clamp the electrode patch 100, more specifically the connector portion 140 of the electrode patch between them. In this example, the first and second clamping members 510, 520 are shown to be two separated elements and the two clamping members 510 and 520 are preferably connected by flexible printed circuit board(s) 515. As shown in FIG. 2, the connector portion 104 of the electrode patch 100 may comprise holes 110a, 110b, 110c, hereinafter referred to as electrode patch holes 110a, 110b, 110c. The holes 110a, 110b, 110c may be macro holes. The first clamping member 510 and the second clamping member 520 may be attached through the electrode patch holes 110a, 110b, 110c using magnetic coupling. The number, size and/or configuration of the of electrode patch holes 110a, 110c, 110c may be different than what is shown in FIG. 2. The electrode patch holes 110a, 110b, 110c may also function as alignment for aligning the connector portion 104 of the patch to the connector 150. For example, the connector device 500 may have alignment pins that are configured to be received by the electrode patch holes 110a, 110b, 110c to ensure that the connection portion 104 is properly aligned and connected to the connector 150.

Figure 6:
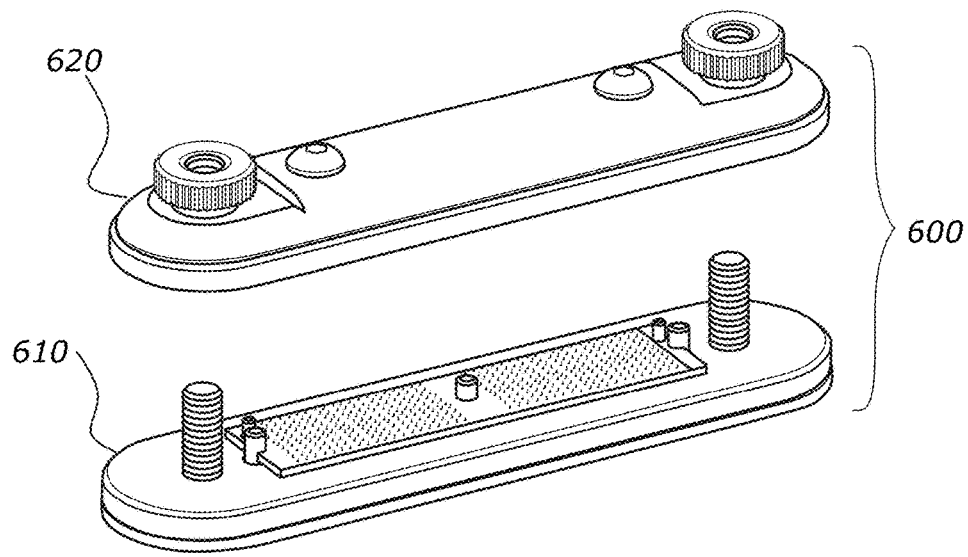
FIG. 6 is an example/embodiment of a connector device according to a second preferred embodiment of the present invention.
Figure 7:
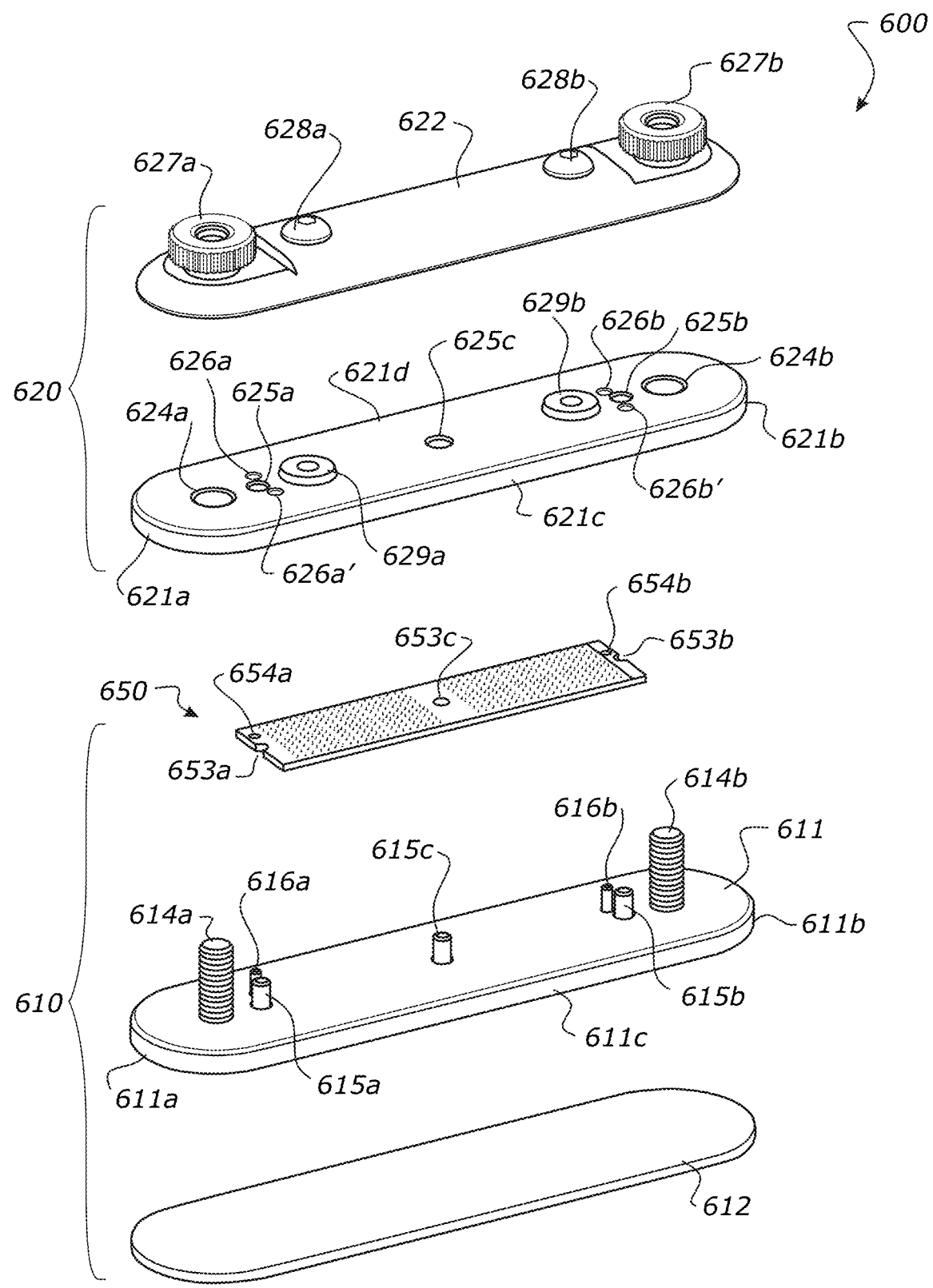
FIG. 7 is an exploded view of the connector device of FIG. 6.

FIG. 6 shows another preferred embodiment of connector device 600 for connecting to the connector portion 104 of the electrode patch 100 and FIG. 7 is an exploded view of the connector device 600 of FIG. 6. As shown in FIGS. 6 and 7, the connector device 600 comprises a first clamping member 610 and a second clamping member 620. The first clamping member 610 and the second clamping member 620 are configured to clamp the electrode patch 100, more specifically the connector portion 104 of the electrode patch 100 between them.

As shown the first clamping member 610 is the bottom/lower clamping member that is configured to clamp the connector portion 104 of the electrode patch 100 from the bottom when the first and second clamping members 610, 620 are secured together to a clamped position.

The first clamping member 110 comprises a first clamping plate 611, a connector 650 and a foam layer 612. As shown, the first clamping member plate 611 may be elongated extending longitudinally from a first end portion 611a and a second end portion 611b and has a lower surface 611c and an upper surface 611d. The foam layer 612 is located on the lower surface 611c and is configured to contact the outer surface of the subject's skin during use. The upper surface 611d may comprise a first stud 614a at or near the first end portion 611a, and a second stud 614b at or near the second end portion 611b. The studs 614a and 614b may be externally threaded. A plurality of dowels 615a, 615b and 615c may be located at the upper surface 611d between the first and second studs 614a and 614b. The dowels 615a, 615b and 615c may be smaller in size (preferably in length, diameter and/or height) as compared to the studs 614a, and 614b. Plurality of connector securing pins 616a and 616b may be located adjacent the dowels. In this example, there are two connector securing pins 616a and 616b are located adjacent the dowels 615a, 615b. The connector securing pin 616a is located adjacent the dowel 615a and the connector securing pin 616b is located adjacent the dowel 615b. No connector securing pin may be located adjacent the intermediate dowel 615c. In one embodiment (not shown), a connector securing pin may optionally be located adjacent the dowel 615c too.

As shown, the connector 650 is configured is located at the upper surface 611d of the first clamping member 610, more specifically the upper surface 611d of the first clamping plate 611 with the contact pins 652 of the connector 650 facing upwards, i.e. towards the direction of the second clamping member 620. The connector 650 may be an array connector. The connector 650 may be an interposer. As shown, the connector 650 may comprise a plurality of dowel receiving connector holes 653a, 653b and 653c for receiving dowels. The dowel receiving connector holes 653a, 653b and 653c may receive the dowels 615a, 615b and 615c respectively as shown in FIG. 6. The connector 650 may comprise securing pin receiving holes 654a and 654b for receiving connector securing pins 616a and 616b. The securing pin receiving holes 654a and 654b may receive the connector securing pins 616a, 616b respectively as shown.

The connector 650 may be similar to the connector 150 as described above with reference to FIGS. 3 and 4. It can be appreciated that the first clamping member 610 may comprise any number of dowels, connector securing pins and/or studs to suit the type of electrode patch 100 that is configured to be clamped by the connector device 600 and the type of connector 650 used.

As shown the second clamping member 620 is the top/upper clamping member for clamping the connector portion 104 of the electrode patch 100 from the top when the first and second clamping members 610, 620 are secured together to the clamped position.

The second clamping member 620 comprises a second clamping member plate 621 and cover plate 622.

The second clamping member plate 621 extends longitudinally between a first end portion 621a and a second end portion 621b and comprises a lower surface 621c and an upper surface 621d. The cover plate 622 is configured to be secured to the second clamping member plate 621 at the upper surface 621d.

The second clamping member plate 621 may comprise a first stud receiving hole 624a at or near the first end 621a, and a second stud receiving hole 624b at or near the second end 621b. Although, not shown, the stud receiving holes 624a and 624b may optionally comprise threaded arrangements (e.g. internal threads) for engaging with the external threads of the first and second studs 614a and 614b respectively. A plurality of dowel receiving holes 625a, 625b and 625c may be located between the first and second studs receiving holes 624a and 624b. The dowels 615a, 615b and 615c may be received through the dowel receiving holes 625a, 625b and 625c respectively when the first and second clamping members 610, 620 are in a clamped position. The dowels receiving holes 625a, 625b and 625c are shown to be less in diameter as compared to the stud receiving holes 624a, 624b as in this example the dowels 615a, 615b, 615c are less in diameter as compared to the studs 614a, 614b. Plurality of connector securing pin receiving holes 626a and 626b may be located adjacent the dowel receiving holes 625a and 625b respectively for receiving the dowel securing pins 616a and 616b respectively. As shown, there may be additional connector securing pin receiving holes 626a' and 626b' which may be located adjacent the dowel receiving holes 625a and 625b respectively and opposite to the connector securing pin receiving holes 626a and 626b respectively. These additional connectors securing pin receiving holes 626a' and 626b' can receive the dowel securing pins 616a, 616b respectively if the second clamping member 620 is turned/rotated 180 degrees in the same plane from the position shown in FIG. 7. This means first and second clamping members 610 and 620 can be secured together to clamp the electrode patch in between them even if one of the clamping members is rotated 180 degrees in a same plane in either a clockwise or anti-clockwise direction.

As shown, the cover plate 622 may comprise a first thumb screw head 627a and a second thumb screw head 627b. The thumb screw heads are rotatable and may have internal threads configured to engage with the threads of the studs 614a, 614b. The first thumb screw head 627a may be configured to rotatably engage with the first stud 614a and the second thumb screw head 627b may be configured to rotatably engage with the second stud 614b. As shown, the cover plate 622 may also comprise optional plate securing screws 628a and 628b that are configured to be received by complimentary plate securing screws receiving holes 629a and 629b respectively that are located at the optional second clamping member plate 621 to further secure cover plate 622 together with the second clamping member plate 621. The complimentary plate securing screws receiving holes 628a and 628b may be formed on the upper surface 621d of the second clamping member plate 621.

In order to clamp the electrode patch 100 between the first and second clamping members 610, 620, the first clamping member 610 and the second clamping member 720 may be first detached from each other as shown in FIG. 6. The electrode patch 100 may then be placed on top of the first clamping member 610. More specifically, the connector portion 104 of the electrode patch 100 may be placed above the connector 750 facing down on the connector 650 so that the contact pads 108 located at the connector portion 104 of the electrode patch 100 may be physically connected to the contact pins 652 of the connector 650.

The first stud 614a may pass through the cut-out 109 of the electrode patch 100 and the second stud 614b may pass through the C-shaped portion 107 of the electrode patch. The dowels 615a, 615b, 615c may align with the electrode patch holes 110a, 110b and 110c respectively. The electrode patch holes 110*a*, 110*b* and 110*c* may be larger in diameter to also receive the connector securing pins 616*a*, 616*b*, 616*c*. Alternatively, there may be additional electrode patch holes to receive the connector securing pins 616*a*, 616*b* and 616*c*.

The second clamping member 620 may be then placed on top of the first clamping member 610 and portion of the electrode patch 100 that is placed on top of the first clamping member 610. The screw heads 627*a*, 627*b* are then tightened by rotating in either clockwise or anti-clockwise direction to thereby clamp the electrode patch 100 between the connecting device 600. The electrode patch 100 that is clamped by the connector device 100 may then be adhered to the outer surface of the skin of the subject using adhesive or similar with the electrodes 102 and foam layer 612 contacting the outer surface of the skin of the subject.

Due to the foam layer 612 being a soft material the abrasions or injury on the skin of the subject during use can be prevented. Similarly, it can be appreciated that having a foam layer 612 for contacting on patient side rather than a hard surface may mean that the connection device 600 of the invention will be more comfortable to be worn by the subject as compared to similar devices having a harder surface.

The connector device 600 may be a portable electronic device such as a data acquisition unit or data logging device or similar that may be worn by the subject to allow electrophysiological monitoring and is preferably battery powered (e.g. using Li-ion battery). Alternatively, the connector device 600 may be an intermediary device configured to be worn by the subject and the connector 650 of that intermediate device 600 may be electrically connected (either by wire or wirelessly) to an electronic device such as a data acquisition device or data logging device to allow electrophysiological monitoring. If the connector device 600 includes any cables or wires, then those cables or wires may be routed through the cut-out 109 formed on the electrode patch 100.

The principals and operations of the data acquisition device or data logging device is well known to a person skilled and need not be described here. However, the connector device 600 may comprise at least one analogue to digital convertor to amplify and digitize a biopotential measurements signals received from the electrode patch 100. There may be multiple (e.g. four) analogue to digital convertors. The analogue to digital convertor(s) may be analogue to digital convertor chip(s). The connector device 600 may comprise a microcontroller. The microcontroller may be configured to receive signals from the analogue to digital convertor, process the signals, and transmit data to a remote computing device to allow monitoring of electrical activity generated by the subject. The analogue to digital convertor(s) may be electrically connected to the microcontroller with a flexible cable(s). The flexible cable(s) may be flexible printed circuit board(s). The electronic component may further comprise a flash memory, Near Field Connection (NFC) module(s) and/or charging circuit(s).

Connector device 500 as described above with reference to FIG. 5 may also be a similar portable electronic device or an intermediate device and may comprise a connector similar to connector 650 in either a first clamping member or a second clamping member.

The connector device 600 may be a part of a connector system comprising a docking device having a compartment that is configured to receive the connector device. The docking device may be a wireless charging device for facilitating wireless charging of the connector device when the connector device is received within the connector device receiving compartment.

It can be appreciated that due to presence of cut-out 109 and electrode patch holes 110*a*, 110*b* and 110*c* skewing of the electrode patch 100 may be prevented when the connector portion 104 of the electrode patch 100 is clamped together by the connector device 600. Preventing skewing of electrode patch 100 can be important to prevent failed connections and cross talks.

After use, the electrode patch may be detached (e.g. peeled out) from the outer surface of the skin of the subject's body. The connection between screw heads 627*a*, 627*b* and studs 614*a*, 614*b* may be loosed by rotating, and the first clamping member 610 and the second clamping member 620 may then be detached from each other. The electrode patch 100 may then be removed from the connector device 600. The electrode patch 100 is preferably a disposable device and can be disposed after use.

Although, FIGS. 6 and 7 show, the first clamping member 610 as the upper clamping member and the second clamping member 620 as the lower clamping member, in an alternative configuration, the first clamping member 610 may be the upper clamping member and the second clamping member 620 may be the lower clamping member. In such configuration, the connector portion 104 of the electrode patch can be placed on top of second clamping member plate 621 of the second clamping member 620 and the connector portion 104 of the electrode patch 100 may face upward towards the downwardly facing connector 650 of the first clamping member 610.

Figure 8:
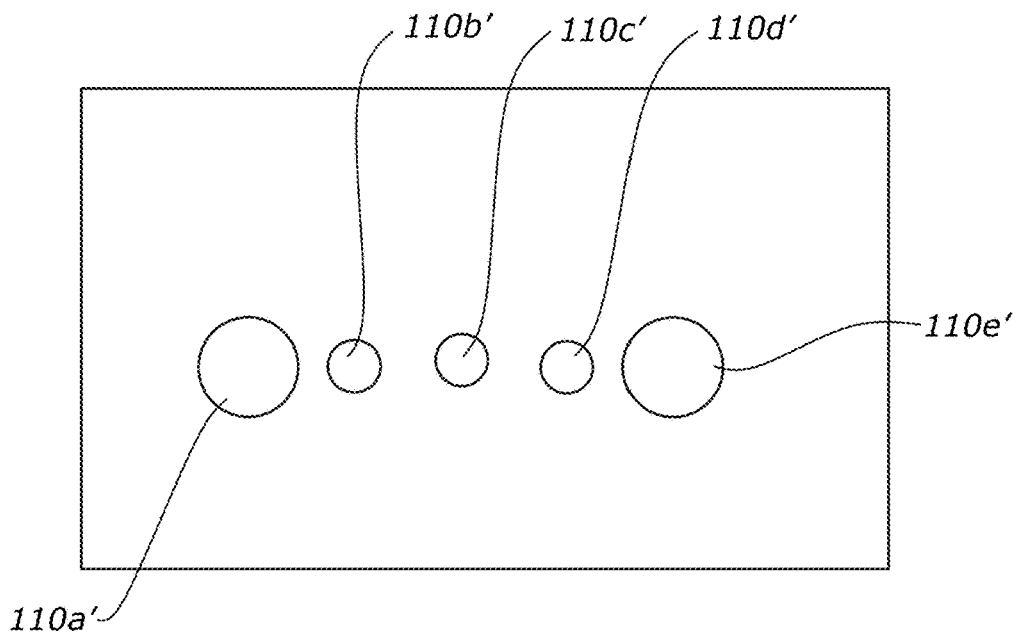
FIG. 8 shows an example of an arrangement of electrode patch holes a connector portion of the electrode patch of FIG. 1.

FIG. 8 shows another example of a connector portion of the electrode patch 100. In FIG. 8, the contact pads and electrical conductors are not shown in FIG. 8 for the sake of clarity. The connector portion of FIG. 8 is substantially the same as connection portion 104 as described above most of the description above with reference to connector portion 104 applies equally to the connector portion and only the differences will be described herein.

As shown, the connector portion of FIG. 8 comprises total of 5 electrode patch holes 110*a*', 110*b*', 110*c*', 110*d*' and 110*e*' that are alignment holes.

When clamped by the connector device 600, the electrode patch holes 110*a*' may be configured to receive the first stud 614*a*; the electrode patch hole 110*b*' may be configured to receive the dowel 615*a* and pin 615*b*; the electrode patch hole 110*c*' may be configured to receive the dowel 615*c*; the electrode patch hole 110*d*' may be configured to receive the dowel 615*b*; and the electrode patch hole 110*e*' may be configured to receive the second stud 614*b*. It can be appreciated that due to presence of electrode patch holes 110*a*', 110*b*', 110*c*', 110*d*' and 110*e*' skewing of the electrode patch 100 is prevented when the connector portion 104 of the electrode patch 100 is clamped together by the connector device 600. These also ensure proper alignment between the connector portion 104' and the connector 104. As mentioned above, preventing skewing of electrode patch 100 can be important to prevent failed connections and cross talks. In the electrode patch having the connector portion of FIG. 8, the cut-out 109 and/or C-shaped portions 107 may be optional. Alternatively, the cut-out 109 may still be present in the electrode patch 100 so that if the connector device 600 includes any cables or wires, then those cables or wires may be routed through the cut-out 109 formed on the electrode patch 100. The size of the connector device for clamping an electrode patch 100 having connector portion 104' may be different from the size of the size of the connector device for clamping an electrode patch 100 having connector portion 104. Alternatively, or additionally, the size of the tongue 103 of the electrode patch 100 may be different to suit the connector portions.

Figure 9:
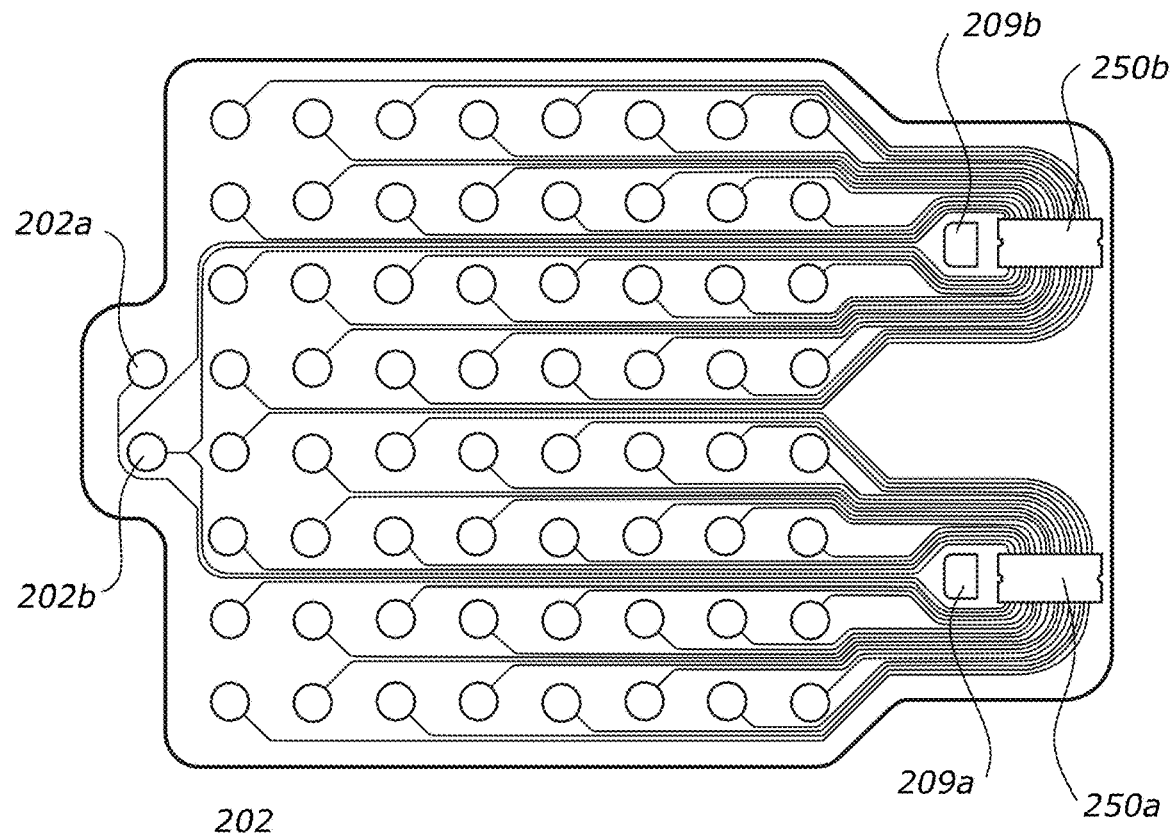
FIG. 9 shows an example/embodiment of an electrode patch according to a second preferred embodiment of the present invention. Connectors of a connector device are also shown.

FIG. 9 shows as example of an electrode patch 200 according to another preferred embodiment of the invention. Most features of the electrode patch 200 is substantially similar to the electrode patch as described above and therefore most of the description above with reference to electrode patch 100 may apply equally to the connector patch 200 and only the differences will be described herein.

The electrode patch 200 may comprise two connector portions. The electrical conductors 206 running as conductive tracks between the electrodes 202, 202a, 202b are routed to two separate connector portions. Electrode 202a is a ground electrode and electrode 202b is a reference electrode. In FIG. 9, the connector portions cannot be seen as they are covered by connectors 250a, 250b. The two connectors 250a, 250b may be the similar as connectors 150 or 750 as described above. Preferably, the two connectors 250a, 250b are identical. Optionally, the connector 250a is different from connector 250b.

Preferably, the two connectors 250a, 250b shown in FIG. 9 are not part of the electrode patch 200 and are instead part of one or more connector devices that are adapted to clamp the electrode patch 200. The connector device(s) can be same as the connector device(s) 500, or 600 as described above. In FIG. 9, the full connector device(s) are not shown for the sake of clarity.

Splitting the connector portions into two or more parts is advantageous over one connector portion because by spiting connector portions in that way, less mating force will be required at each connecting portion to achieve reliable coupling between the electrode patch 200 and connector device(s).

There are two cut-outs 209a, 209b in electrode patch 200. Cut-outs may be optional.

In one alternative optional embodiment, the connectors 650 are adhered to the connector portions (e.g. by adhesive or similar) and are part of the electrode patch 200 instead of being part of the connector devices. In such embodiment, one or more connector device may comprise cables for allowing electric communication between the connectors 650 and the one or more connector device.

The shape of the tongue 203 of the electrode patch 200 is shown to be substantially rectangular. However, the tongue 203 may be of many other suitable shapes. Although not shown, the tongue 203 may optionally comprise C-shaped portion adjacent each of the connector portions.

Each connector portion of the electrode patch 200 may be similar to the connector portions described above. Each connector portion may look like the first half 104a or a second half 104b of the connector portions shown in FIG. 2. More specifically, the groups of contact pads of each connector portion of electrode patch 200 may be in a staggered format as shown in the first half 104a or a second half 104b of the connector portion as shown in FIG. 2.

Figure 10:
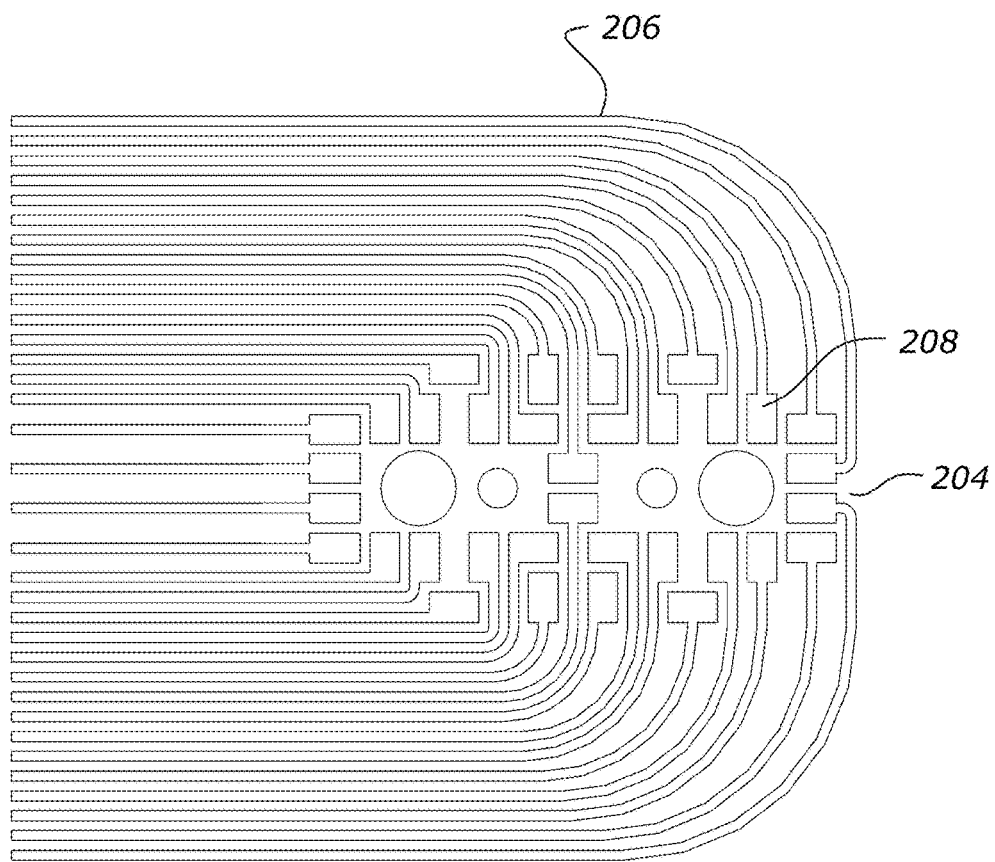
FIGS. 10 and 11 show an example of a connector portion of the electrode patch of FIG. 9 and also shows electrical conductors being attached to the connector portion.
Figure 11:
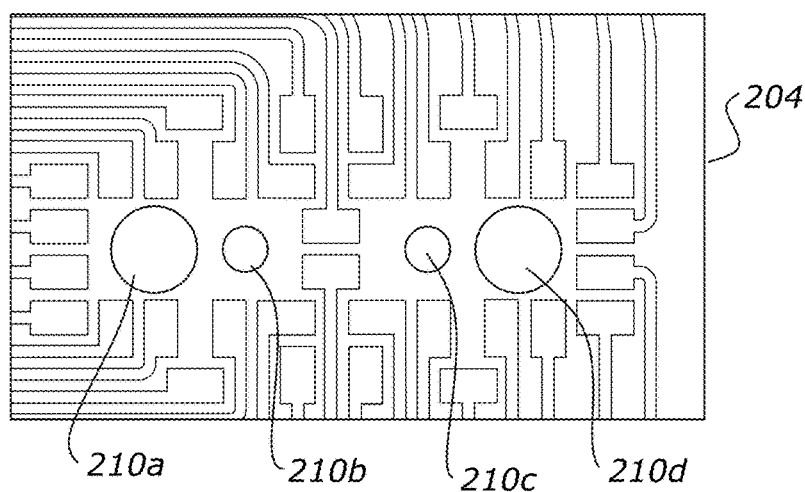

FIGS. 10 and 11 show one example of one of the connector portions of the electrode patch 200. In other words, the connector portion 204 shown in FIGS. 10 and 11 is one of the two connector portions of the electrode patch 200. As shown, the connector portion 204 may comprise 34 contact pads 208 in total in a staggered format. The 34 contact pads are connected with 32 of the 64 array electrodes 202, a ground electrode 202a and a reference electrode 202b through electrical conductors 206. The electrical conductors 206 run as conductive tracks between the electrodes 202, 202a, 202b and the connector portion 204, more specifically, between the electrodes 202, 202a, 202b and the contact pads of the connector portion 204. Another one of the two connector portions of the electrode patch 200 may be similar to the connector portion 204 and that connector portion 204 may also have 34 contact pads connected with the remaining 32 of the 64 array electrodes 202, a ground electrode 202a and a reference electrode 202b using electrical conductors 206.

Figure 12:
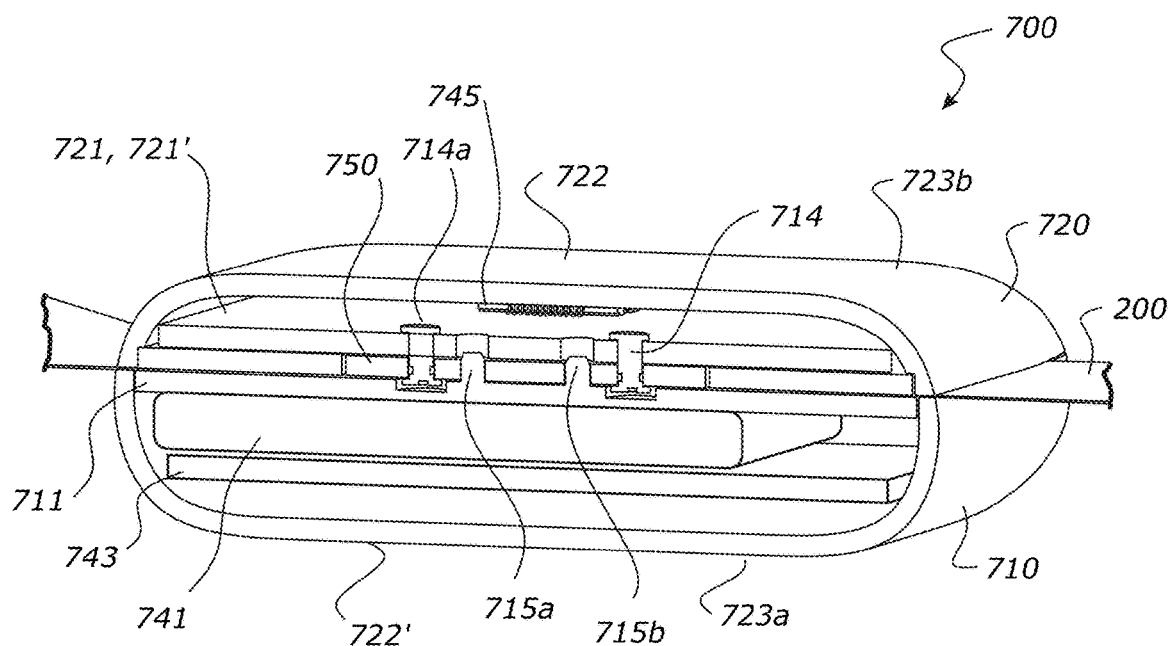
FIG. 12 shows an example/embodiment of a connector device according to a third preferred embodiment in a clamped position.

FIG. 12 shows another example of a preferred embodiment of the connector device 700 and electrode patch 200 that is clamped between the first clamping member 710 and second clamping member 720 of the electrode patch.

The connector device 700 of this example is similar in most aspects to the connector device 600 described above and the differences can be identified by comparing FIGS. 5 and 6 with FIG. 12. In FIG. 12, the features that are similar to those shown in FIG. 6 are identified with the same reference numeral, incremented by 100. Most of the description of the connector device 600 of a preferred embodiment above, equally applies to the connector device 600 and therefore and therefore need not be described again in too much detail. Only the main features will be discussed.

As shown, the connector device 700 only comprises two dowels 715a, 715b between first and second studs 714a, 714b, unlike connector device 600 comprising the dowels 615a, 615b, 615c. The connector 750 is part of the second clamping member 720 instead of the first clamping member. The first and second clamping members 710, 720 may both comprise housing 723a, 723b that are both half elliptical in shape with smooth external surface and in the clamped position as shown in FIG. 12, the connector device 700 is substantially elliptical in shape. Due to external surface of both housings 723a, 723b being smooth and of the same shape, either of the first and second clamping members can be placed proximal to the outer surface of the skin of the subject during use. If the first clamping member 710 is to be placed proximal to the outer surface of the skin of the subject, then the electrode patch 200 will been to be placed on top of the first clamping member with the contact pads 208 of the electrode patch 200 facing upwards towards the second clamping member 720. This is because the second clamping member 720 comprises the connector 750. Similarly, if the first clamping member 710 is to be placed proximal to the outer surface of the skin of the subject, then the electrode patch 200 will been to be placed on top of the first clamping member with the contact pads 208 of the electrode patch 200 facing downwards towards the second clamping member 820 comprising the connector 750. Although, not shown, a foam layer may optionally be added to the surface of the connector device 700 that is configured to be attached to the outer surface of the skin of the subject.

The first and second clamping members 710, 720 may be secured together to be in the clamped position using many suitable securing means such as but not limited to magnetic coupling, latch arrangement, snap fit arrangement etc.

While clamping the electrode patch 200 using the connector device 700, the electrode patch hole 210a may be configured to receive the first stud 714a; the electrode patch hole 210b may be configured to receive the dowel 715a; the electrode patch hole 210c may be configured to receive the dowel 715b; and the electrode patch hole 210d may be configured to receive the second stud 714b. It can be appreciated that due to presence of electrode patch holes 210a, 210b, 210c, 210d skewing of the electrode patch 200 is prevented when the connector portion 204 of the electrode patch 200 is clamped together by the connector device 700. The electrode patch holes 210a, 210b, 210c, 210d are also alignment holes as they allow for proper alignment of the connector portion 204 and the connector 750.

Two separate connector devices 700 may be used to clamp two connector portions 204.

Figure 15:
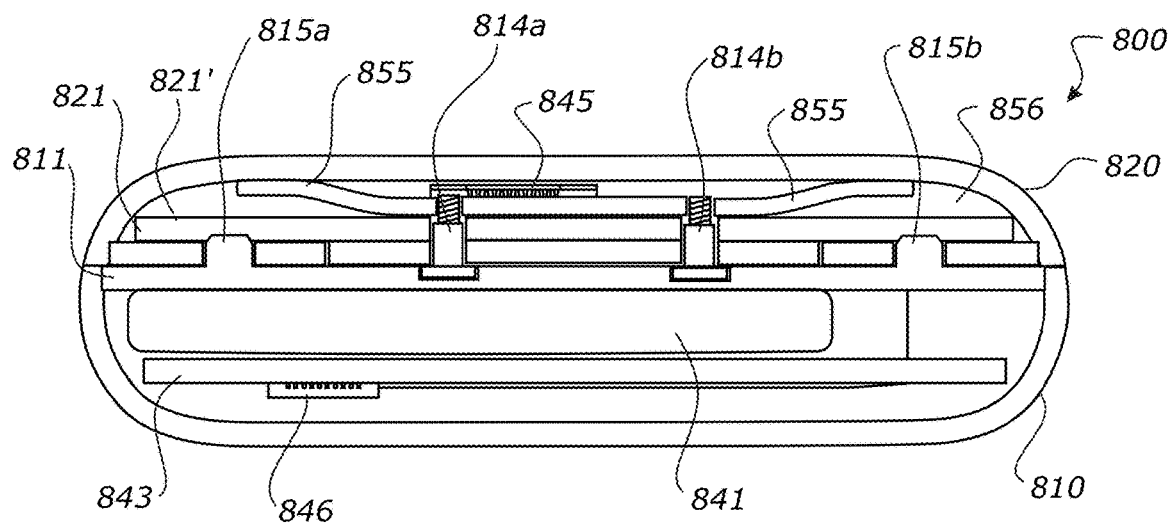
FIG. 15 shows an example/embodiment of a connector device according to a fourth preferred embodiment of the present invention.

The connector device of FIG. 15 is preferably an electronic device such as a data acquisition device or data logging device and is preferably battery powered (see Li-ion battery 741). The principals and designs of the data acquisition device or data logging device is well known to a person skilled and need not be described here. However, the connector device 700 may comprise at least one analogue to digital convertor to amplify and digitize a biopotential measurements signals received from the electrode patch 200. There may be multiple (e.g. four) analogue to digital convertors. The analogue to digital convertor(s) may be analogue to digital convertor chip(s). The connector device 700 may comprise a microcontroller. The microcontroller may be configured to receive signals from the analogue to digital convertor, process the signals, and transmit data to a remote computing device to allow monitoring of electrical activity generated by the subject. The analogue to digital convertor(s) may be electrically connected to the microcontroller with a flexible cable(s). The flexible cable(s) may be flexible printed circuit board(s). The electronic component may further comprise a flash memory, Near Field Connection (NFC) module(s) and/or charging circuit(s).

As shown in FIG. 12, there may be a main Printed Circuit Board (PCB) 743. The PCB 743 may comprise a microcontroller and other electronic circuitry such as but not limited to microcontroller, flash memory, Near Field Connection (NFC) module(s) (e.g. Bluetooth modules), charging circuits etc. There may be another PCB 721' comprised or formed clamping plate 721 holding at least one analogue to digital converter (preferably 4 analogue to digital convertor chips). A zif connector 745 may be used to connect the PCB comprised or formed clamping plate 721 with the main PCB 743 using a flexible cable (e.f. flexible printed circuit board). A corresponding zif connector (not shown) may be located on the main PCB 743 and that corresponding zif connector may be electrically connected with the zif connector 745 using the flexible cable.

Figure 13:
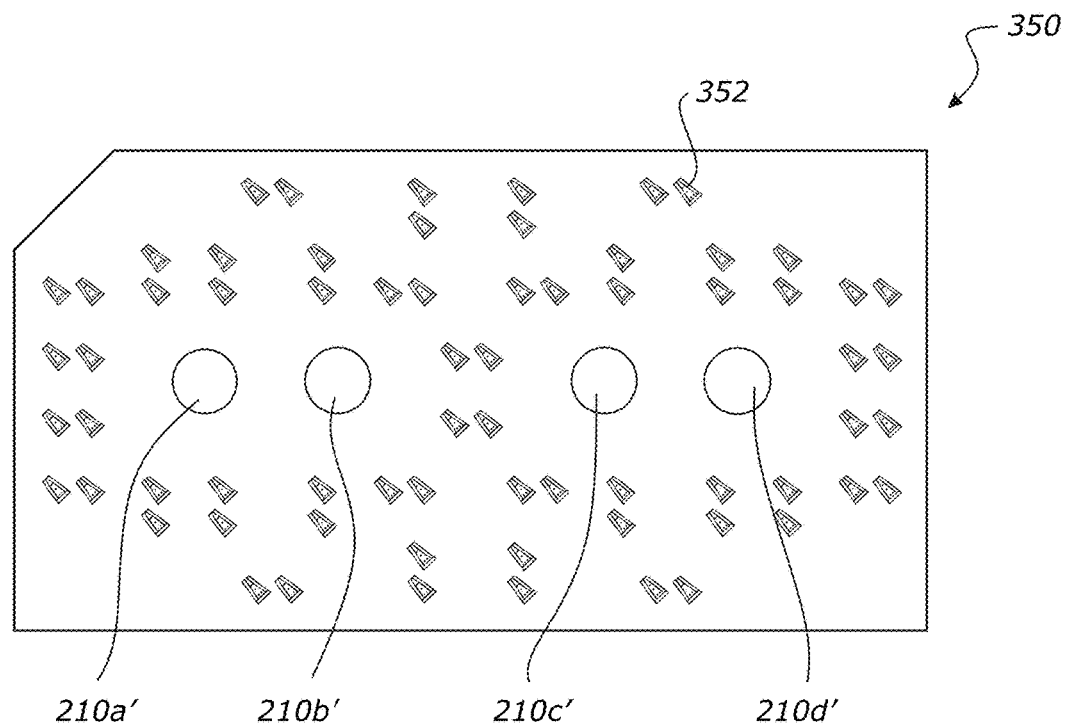
FIG. 13 shows an example of a connector that can be used for connecting to the connector portion of FIGS. 10 and 11.

FIG. 13 shows another example of a connector 350 to physically connect with the connector portion 204 described above. The connector 350 of this example is similar in most aspects to the connector 150 described above and the differences can be identified by comparing FIG. 3 with FIG. 13. The smaller number of conductive contact pins 352 on the connector in FIG. 13 is designed for a configuration that allows for reduced mating force. The reliability and lifespan of the coupling device may be improved when there is reduced mating force. In FIG. 13, the features that are similar to those shown in FIG. 6 are identified with the same reference numeral, incremented by 200.

One of the corners of the connector is shown to be angled in FIG. 13 but need not be angled.

The conductive contact pins 352 may optionally be trapezoidal in shape. Although, not shown in FIG. 13, the conductive contact pins 352 may optionally protrude out from the body of the connector 352.

Figure 14:
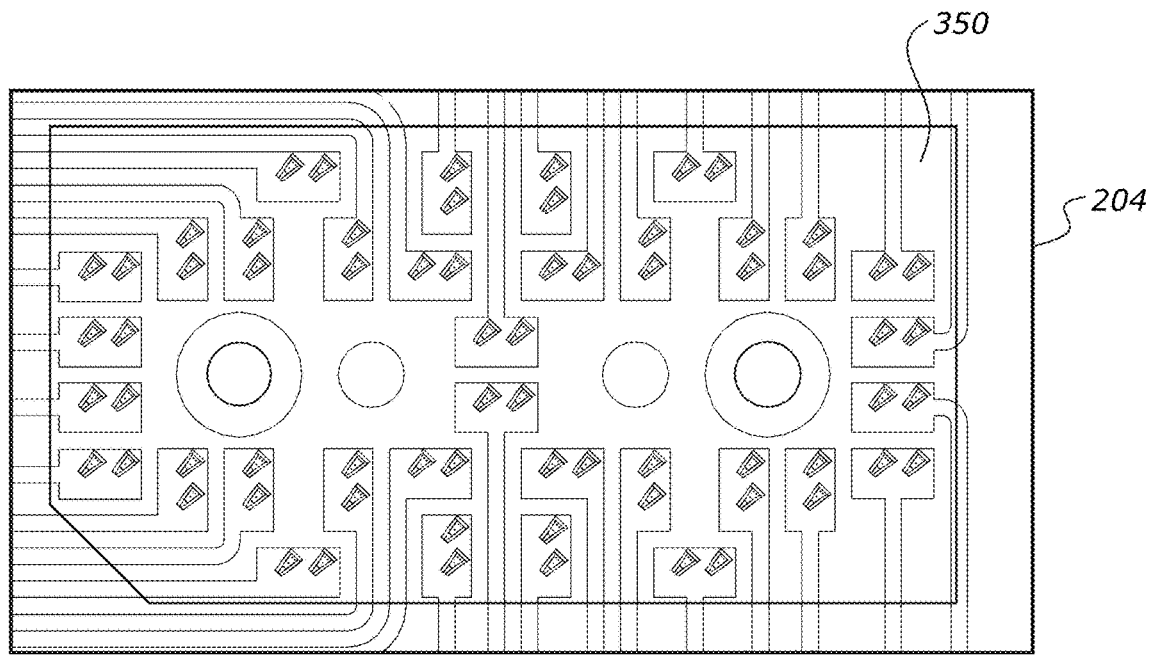
FIG. 14 shows an example how the connector of FIG. 13 can be used for connecting to the connector portion of FIGS. 10 and 11.

The conductive contact pins 352 are arranged/spaced in a specific orientation as shown in FIG. 13 to be in contact with the contact pads 208 of the connector portion 204. FIG. 14 shows the conductive contact pins 352 being in contact with the contact pads 208 when physically connected to the contact pads 208. As shown, each contact pad 208 may be configured to be in contact with two conductive contact pins. This enables a backup contact between the contact pad 208 and conductive contact pins. Therefore, even if one of the two conductive contact pins become damaged, worn, or covered by residue e.g. when the device is cleaned between patients, the device will still function normally.

FIG. 15 shows another example of a preferred embodiment of the connector device 800 that is configured to clamp the electrode patch 200 that is configured to clamp the electrode patch 200 between the first clamping member 810 and second clamping member 820.

The connector device 800 of this example is similar in most aspects to the connector device 700 described above and the differences can be identified by comparing FIG. 12 with FIG. 15. In FIG. 15, the features that are similar to those shown in FIG. 12 are identified with the same reference numeral, incremented by 100. Most of the description of the connector device 700 of a preferred embodiment above, equally applies to the connector device 800 and therefore need not be described again in too much detail. Only the main differences will be discussed.

As shown, the connector device 800 only comprises two dowels 815a, 815b. Unlike in the connector device 700 where the dowels 715a, 715b are located between first and second studs 714a, 714b, the first and second studs 814a, 814b of the connector device 700 are located between the dowels 815a, 815b. Although, not shown, a foam layer may optionally be added to the surface of the connector device 800 that is configured to be attached to the outer surface of the skin of the subject.

While clamping the electrode patch 200 using the connector device 800, the electrode patch hole 210a may be configured to receive the dowel 815a; the electrode patch hole 210b may be configured to receive the first stud 814a; the electrode patch hole 210c may be configured to receive the second stud 814b and the electrode patch hole 210d may be configured to receive the dowel 815b. It can be appreciated that due to presence of electrode patch holes 210a, 210b, 210c, 210d skewing of the electrode patch 200 is prevented when the connector portion 204 of the electrode patch 200 is clamped together by the connector device 800.

Two separate connector devices 800 may be used to clamp two connector portions 204.

The connector device of FIG. 15 is preferably an electronic device such as a data acquisition device or data logging device and is preferably battery powered (see Li-ion battery 841). The principals and operations of the data acquisition device or data logging device are well known to a person skilled and need not be described here. However, the connector device 800 may comprise at least one analogue to digital convertor to amplify and digitize a biopotential measurements signals received from the electrode patch 200. There may be multiple (e.g. four) analogue to digital convertors. The analogue to digital convertor(s) may be analogue to digital convertor chip(s). The connector device 800 may comprise a microcontroller. The microcontroller may be configured to receive signals from the analogue to digital convertor, process the signals, and transmit data to a remote computing device to allow monitoring of electrical activity generated by the subject. The analogue to digital convertor(s) may be electrically connected to the microcontroller with a flexible cable(s). The flexible cable(s) may be flexible printed circuit board(s). The electronic component may further comprise a flash memory, Near Field Connection (NFC) module(s) and/or charging circuit(s).

As shown in FIG. 15, there may be a main Printed Circuit Board (PCB) 843. The PCB 843 may comprise a microcontroller and other electronic circuitry such as but not limited to microcontroller, flash memory, Near Field Connection (NFC) module(s) (e.g. Bluetooth modules), charging circuits etc. There may be another PCB 821' comprised or formed clamping plate 821 holding at least one analogue to digital converter (preferably 4 analogue to digital convertor chips). A zif connector 845 may be used to connect the PCB comprised or formed clamping plate 821 with the main PCB 843 using a flexible cable (e.f. flexible printed circuit board). A corresponding zif connector 846 may be located on the main PCB 843 and that corresponding zif connector may be electrically connected with the zif connector 845 using the flexible cable.

The connector device 800 comprises a biasing member which in this example is a leaf spring 855. The leaf spring 855 is shown in FIG. 15 to be located in the second clamping member 820. The leaf spring is configured to bias the second clamping member to move towards the direction of the electrode patch (more specifically, connector portion of the electrode patch) that is sandwiched between the first clamping member 810 and second clamping member 820. Such biasing of the second clamping member 820 to move towards the direction of the electrode patch will allow for a proper connection between the conductive contact pins 852 of the connector 850 and the connector portion of the electrode patch.

Figure 16:
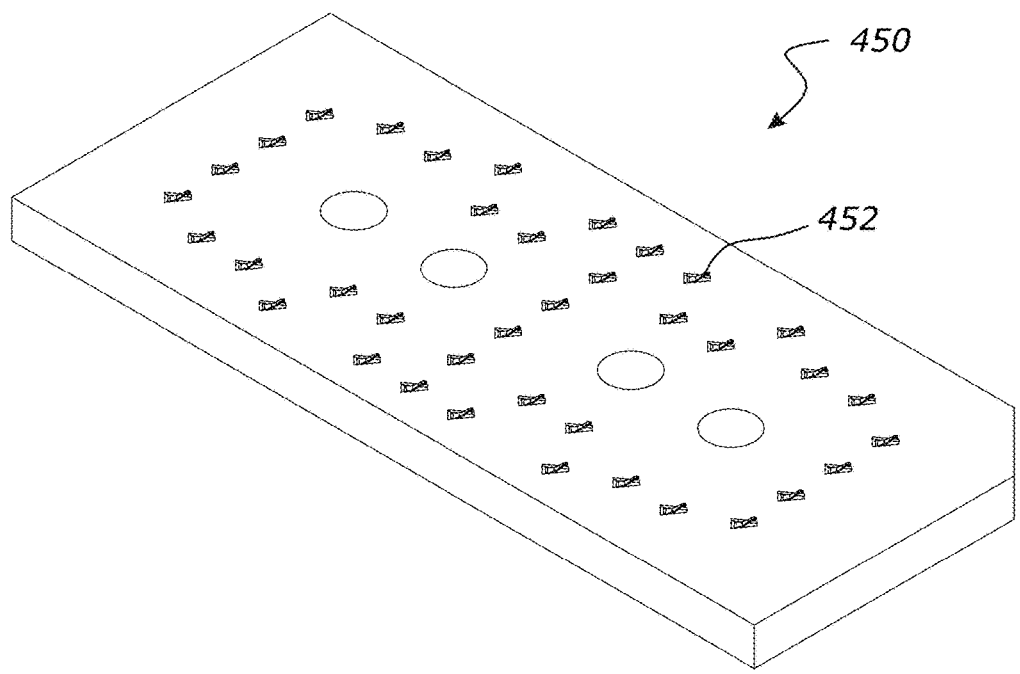
FIG. 16 shows a top plan view of another example of a connector that can be used for connecting to the connector portion of FIGS. 10 and 11.
Figure 17:
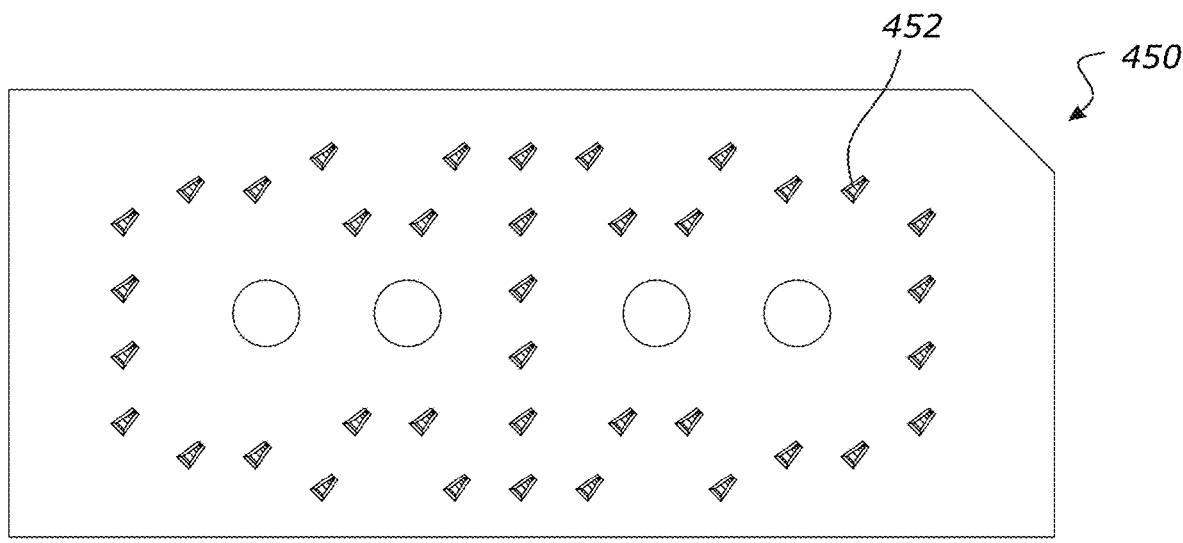
FIG. 17 shows a perspective view of the connector of FIG. 16.
Figure 18:
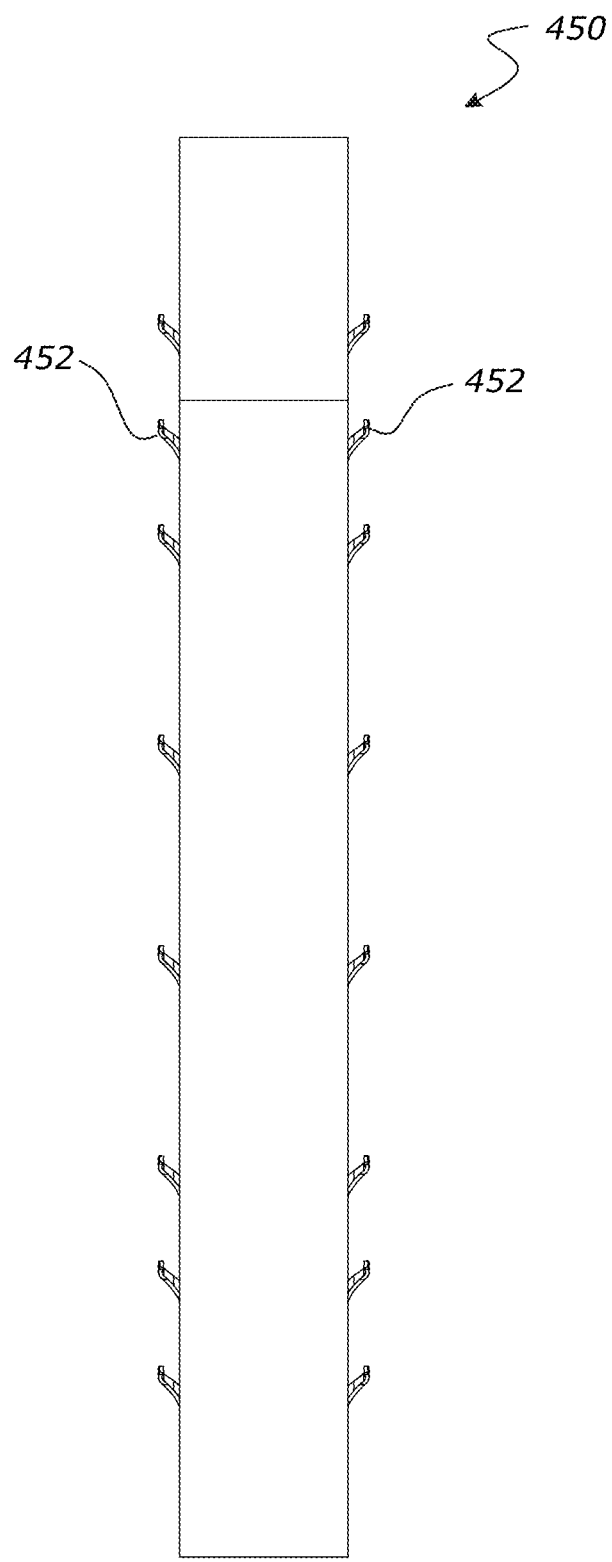
FIG. 18 shows a side view of the connector of FIG. 16.

FIGS. 16-18 show another example of a connector 450 which may be an array connector or an interposer to physically connect with the connector portion 204.1 described below in Reference to FIG. 19. The connector 450 of this example is similar in most aspects to the connector 350 described above and the differences can be identified by comparing FIG. 13 with FIGS. 16-18 The smaller number of conductive contact pins on the connector 450 in FIGS. 16-18 are designed for a configuration that allows for reduced mating force. The reliability and lifespan of the connector 450 may be improved when there is reduced mating force. In FIGS. 16-18, the features that are similar to those shown in FIG. 13 are identified with the same reference numeral, incremented by 100.

One of the corners of the connector is shown to be angled in FIGS. 16-18 but need not be angled.

The conductive contact pins 452 may protrude out from the body of the connector 452 as shown in FIG. 18. The conductive contact pins 452 may be located on both opposing face sides of the connector 450 as shown so that the connector pins on either face side of the connector 450 can be used to contact pads 208.1 of the connector portion 204.1 described below with reference to FIG. 19. It may be possible that the connector 150, 250, 350 also has connector pins on each face side.

The conductive contact pins 452 are arranged is a specific way as shown in FIG. 14 to be in contact with the contact pads 208.1 of the connector portion 204.1. The conductive contact pins 452 may be in contact with the contact pads 208.1 when physically connected to the contact pads 208.1. Each contact pad 208.1 may be configured to be in contact with only one conductive contact pin. This reduces the overall force required for connecting to the contact pads 208.1.

Figure 19:
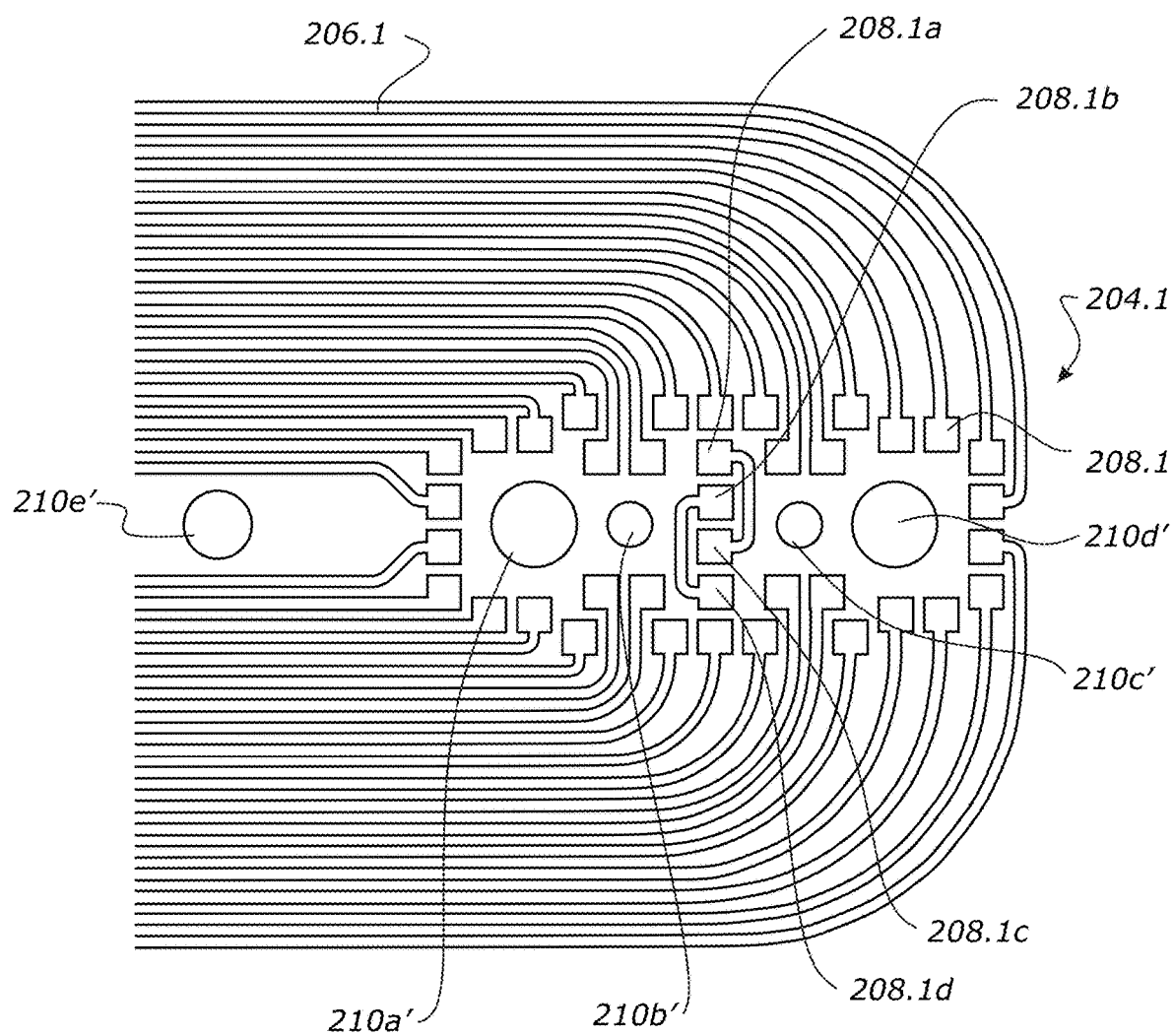
FIG. 19 shows an example of a connector portion of the electrode patch of FIG. 9 and also shows electrical conductors being attached to the connector portion.

FIG. 19 shows another example of one of the connector portions of the electrode patch 200. In other words, the connector portion 204.1 shown in FIGS. 10 and 11 is one of the two connector portions of the electrode patch 200. As shown, the connector portion 204.1 may comprise 38 contact pads 208 in total in a staggered format. The 34 contact pads are connected with 32 the 64 array electrodes 202, a ground electrode 202*a* and a reference electrode 202*b* through electrical conductors 206.1. The electrical conductors 206.1 run as conductive tracks between the electrodes 202, 202*a*, 202*b* and the connector portion 204.1, more specifically, between the electrodes 202, 202*a*, 202*b* and the contact pads 208.1 of the connector portion 204.1. Another one of the two connector portions of the electrode patch 200 may be similar to the connector portion 204 and that connector portion 204.1 may also have 34 contact pads connected with the remaining 32 of the 64 array electrodes 202, a ground electrode 202*a* and a reference electrode 202*b* using electrical conductors.

One major difference between the connector portion 204 of FIG. 10 and connector portion 204.1 of FIG. 19, is that the connector portion 204.1 of FIG. 19 comprises 4 additional connector pads 208.1*a*, 208.1*b*, 208.1*c*, 208.1*d* at or near the centre of the connector portion 204.1. Also, the orientation of conductive contact pins 452 of connector 450 are different from the orientation of the conductive contact pins 352 on connector 350.

It can be appreciated that different versions of connectors may be used to connect to the connector portion 204.1 of FIG. 19 and the 4 additional connector pads 208.1*a*, 208.1*b*, 208.1*c*, 208.1*d* may allow to determine the type of connector that is connected to the connector portion 204.1. For example, the connector 350 or connector 450 may be used to connect to the connector portion 204.1. The 4 additional connector pads 2.8.1*a*, 2.8.1*b*, 208.1*a*, 208.1*d* at the centre of the connector portion 2.4.1 allows to determine which version of the connector is used to connect to the connector portion 204.1. If connection with conductive contact pins at all of the 4 additional connector pads 2.8.1*a*, 2.8.1*b*, 208.1*a*, 208.1*d* is detected that may indicate that connector 450 of FIGS. 16-18 is used to connect to the connector portion 204.1. Similarly, if no connection with conductive contact pins at all of the 4 additional connector pads 2.8.1*a*, 2.8.1*b*, 208.1*a*, 208.1*d* is detected then that may indicate that connector 350 of FIG. 13 is used to connect to the connector portion 204.1.

While clamping the electrode patch 200 at connector portion 204.1 using the connector device 800, the electrode patch hole 210*a*' may be configured to receive the dowel 815*a*; the electrode patch hole 210*b*' may be configured to receive the first stud 814*a*; the electrode patch hole 210*c*' may be configured to receive the second stud 814*b* and the electrode patch hole 210*d*' may be configured to receive the dowel 815*b*. It can be appreciated that due to presence of electrode patch holes 210*a*', 210*b*', 210*c*', 210*d*' skewing of the electrode patch 200 is prevented when the connector portion 204.1 of the electrode patch 200 is clamped together by the connector device 800. In FIG. 19, the electrode patch holes 210*a*' and 201*d*' are shown to be of a larger diameter than electrode patch holes 210*b*' and 201*c*' that is because in the connector device 800, the dowel 815*a*, 815*b* are larger in diameter than first and second studs 814*a*, 814*b*.

It may be appreciated that the size, shape, orientation and number of the electrode patch holes in a connector portion of an electrode patch may be customized to suit a connector device that is being used to clamp the connector portion of that electrode patch.

In FIG. 19, a cut-out 209' is shown which is optional. The cut-out is same as cut-out 209*a*, or 209*b* shown in FIG. 9 except that the cut-out 209' is shown in FIG. 19 as being circular in shape (but that cut-out 209*a* can be any other shape).

Figure 20:
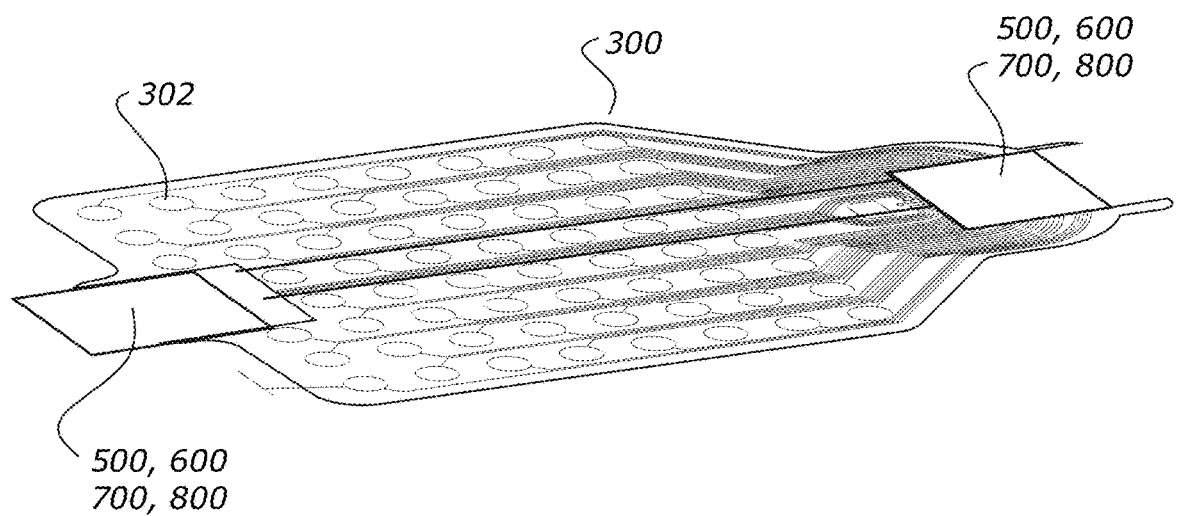
FIG. 20 shows an example/embodiment of an electrode patch according to a third preferred embodiment of the present invention. Schematic representations of connector devices are also shown.

FIG. 20 shows as example of an electrode patch 300 according to another preferred embodiment of the invention. Most features of the electrode patch 300 is substantially similar to the electrode patch 100 as described above and therefore most of the description above with reference to electrode patch 100 may apply equally to the connector patch 300 and only the differences will be described herein.

The electrode patch 300 may comprise two connector portions 304a, 304b (see FIG. 21) on two opposite sides of the electrode patch 300—two opposite side of the array electrodes 300. In FIG. 20, connector device is schematically shown for connecting to two connector portions. The connector device may be any one of the connector devices 500, 600, 700 and 800 as described above. The configuration of electrode patch 300 as shown in FIG. 20 is advantageous because, it has an advantage of distributing the weight and bulk of connector devices in two different regions to be better balanced during use. Since two connector devices will be needed to connect to two connector portions 304a, 304b, additional electrical conductor(s) 206' may run as conductive tracks to electrically connect the two connector portions 304a, 304b. The additional electrical conductor(s) may run as conductive tracks through the substrate of the electrode patch 300 but without any physical contact with any other electrical conductors 206 and electrodes 302 of the electrode patch 300. Such additional electrical conductor(s) 306' allows the connector that is connected to the connector portion 304a and the connector that is connected to the connector portion 304b to both receive signals that are time-synchronized. It also allows connector connected to connector portion 304a and the connector connected to connection portion 304b to operate together.

Figure 21:
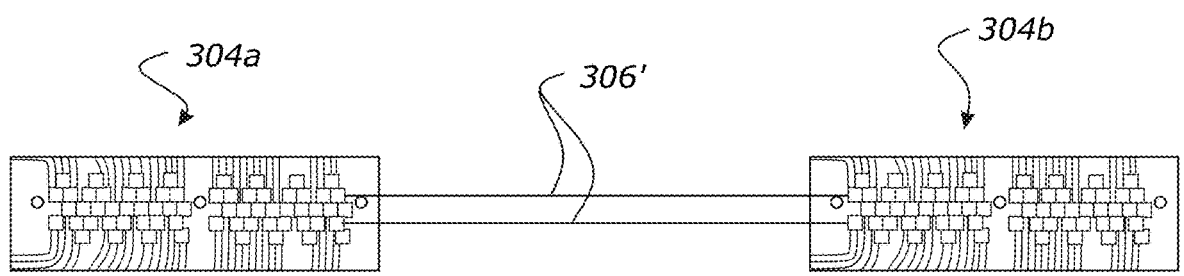
FIG. 21 shows an example/embodiment of the connector portions of the electrode patch of FIG. 15.

The connector portions 304a, 304b may be similar to the connector portion 104 as described above. This is shown in FIG. 21. Alternatively, the connector portions 304a, 304b may be similar to the connector portion 204 or 204.1 as described above.

In one alternative embodiment, the connector portions 204a, 204b of the electrode patch 200 may be located at two opposite sides of the array electrodes 202 instead of being located at the same side of the array electrodes 202. Additional electrical conductor(s) similar to electrical conductor(s) 306' may be used to connect the connector portions 204a and 204b in a similar manner as described above with reference to FIG. 21.

Figure 22:
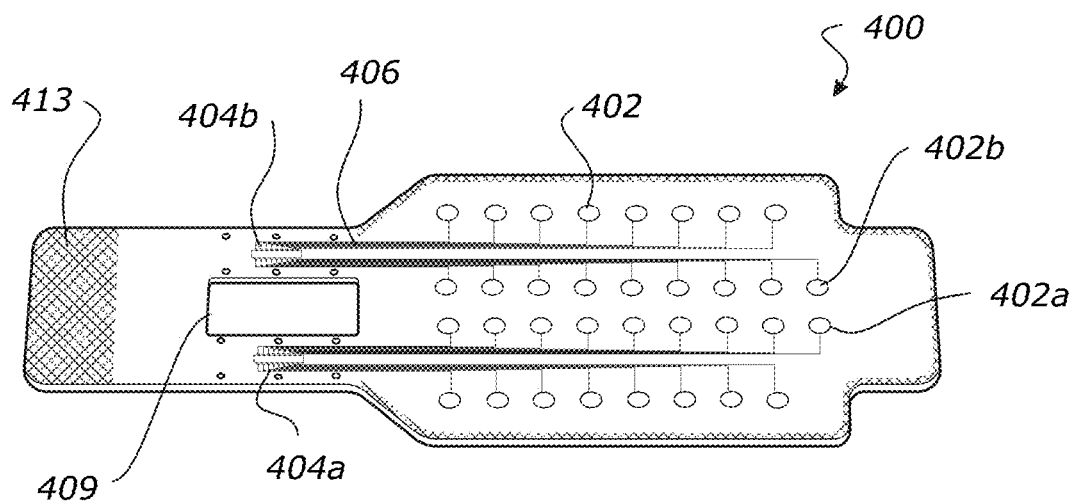
FIG. 22 is an example/embodiment of an electrode patch according to a fourth preferred embodiment of the present invention. Schematic representations of connector devices are also shown.

FIG. 22 shows as example of an electrode patch 400 according to another preferred embodiment of the invention. Most features of the electrode patch 400 is substantially similar to the electrode patch 100 as described above and therefore most of the description above with reference to electrode patch 100 may apply equally to the connector patch 400 and only the main differences will be described herein.

In FIG. 22, the electrode patch 400 is shown to contain contains 36 array electrodes 402, a ground electrode 402a and a reference electrode 402b. However, the number of array electrodes 402 may be more than 32 (such as 64 as described in previous embodiments or even more than 64). In some embodiments, the electrode patch 400 may have less than less than 32 array electrodes 402.

The electrode patch 400 may comprise two connector portions 404a, 402b. The electrical conductors 406 running as conductive tracks between the electrodes 402, 402a, 402b are routed to two separate connector portions 404a, 404b.

Splitting the connector portions 402a, 402b into two or more parts is advantageous over one connector portion because by spiting connector portions in that way, less mating force will be required at each connecting portion to achieve reliable coupling between the electrode patch 400 and connector device(s). Also, splitting the connector portions 402a, 402b into two or more parts means the connector portions will be smaller than a single connector portion and can be placed strategically within the electrode patch 400 to reduce the overall size of the electrode patch 400.

A large cut-out 409 that is located between the connector portions 402a, 402b. The cut-out 409 is shown to be substantially rectangular. However, the cut-out 409 may be of many other suitable shapes. The cut-out 409 is for a proper alignment of the electrode patch 400 on a connector device such as connector device 900 as described below.

The shape of the tongue 403 of the electrode patch 400 is shown to be substantially rectangular. However, the tongue 403 may be of many other suitable shapes. In retain embodiments, there may be no tongue and the dimension of the primary region comprising electrodes 402 may be same or substantially the same as the dimension of the region should in FIG. 22 as the tongue 403. In certain embodiments, the primary region containing electrodes 402, 402a, 402b may be of different shapes than what is shown in FIG. 22. The primary region may be wider or smaller than what is shown in FIG. 22 depending upon the intended application of the patch 400.

Each connector portion of the electrode patch 200 may be similar to the connector portions 104, 204 described above. Alternatively, each connector portion may look like the first half 104a or a second half 104b of the connector portion 104 shown in FIG. 2. More specifically, the groups of contact pads of each connector portion of electrode patch 400 may be in a staggered format as shown in the first half 104a or a second half 104b of the connector portion as shown in FIG. 2.

The electrode patch may comprise adhesive or layer of adhesive 413 on the edges and on the tongue 403 as shown in FIG. 17 to allow the electrode patch 400 to adhere to the outer surface of the skin of the subject during use. Although not shown, the electrode patch 100, 200, 300 as described above may also contain adhesive layer in the tongue(s) and the edges, specifically edges of the primary region in a similar manner.

The electrode patch 400 may comprise a plurality of alignment holes 414 near each of the connector portions 404a, 404b. In the example shown in FIG. 17, there are 6 alignment holes 414 near connector portion 404a and another 6 alignment holes near connector portion 404b. The alignment holes 414 are for a proper alignment of the electrode patch 400 on a connector device such as a connector device 900 described below. Even more specifically, the alignment holes 414 are for a proper alignment of the connector portions 404a, 404b of electrode patch 400 with the connectors such as connectors 950 of the connector device 900 as described below.

Figure 23:
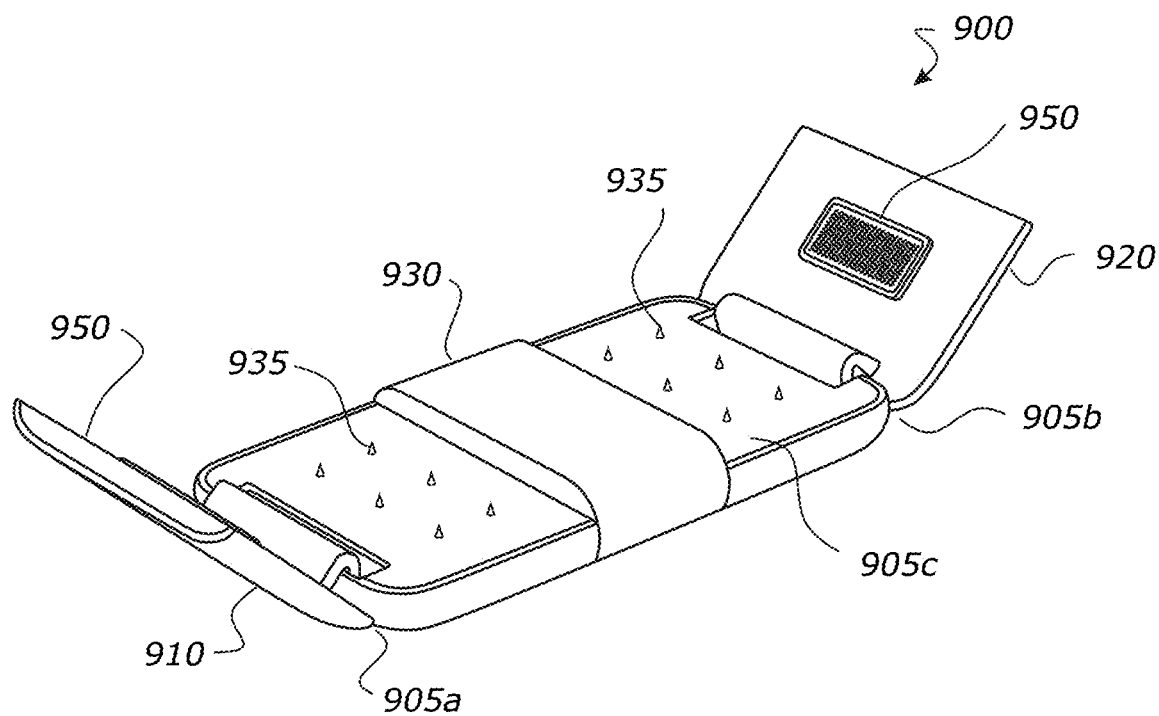
FIG. 23 shows an example/embodiment of a connector device according to a fifth preferred embodiment in an open/release position.

FIG. 23 shows a connector device 900 according to a further preferred embodiment of the invention.

A connector device 900 comprises a main body 905 extending from a first end portion 905a to a second end portion 905b that is located opposite the first end portion 905a. The main body 905 has a planer surface which is a top surface 905c and a bottom surface 905d (see FIG. 25). The top surface 805c is configured to receive an electrode patch 400 for use in monitoring electrical activity generated by a subject.

As shown in FIGS. 17 and 18, the connector device 900 comprises a first clamping member 910 which is a flap that is hingedly/pivotally mounted to the main body 905d at or near the first end portion 905a. The connector device 900 also comprises a second clamping member 920 which is also a flap that is hingedly/pivotally mounted to the main body at or near the second end portion 905b.

The first and second clamping members 910, 920 are configured to move between an open position as shown in FIG. 23 and a closed position as shown in FIG. 19. As shown, in the open position the first clamping member 910 and the second clamping member 920 are both configured to pivotally move away from the top surface 905c and at least partially, preferably fully, reveal the top surface 905c. Similarly, in the closed position the first clamping member 910 and the second clamping member 920 are both configured to move pivotally towards the top surface 905c and partially, preferably fully, conceal the top surface 905c.

At least one, but preferably both of the first and second clamping members 910, 920 comprise at least one connector 950 that is configured to be physically and operatively connected with the electrode patch 400 for receiving the electrical signals from multiple electrodes of the electrode patch 400 to allow monitoring the electrical activity generated by the subject. Therefore, no cable is required to connection between the connector 850 and the electrode patch 400. The connector may be the connector 150 or 350 as described above.

The connector device 900 may comprise at least one alignment feature configured to align and/or retain the electrode patch 400 onto the top surface. In FIG. 23 a plurality of alignment features 930, 935 are shown. The alignment features are in the form of a protrusion 935 and alignment pins 935. The protrusion that is configured to be received by at least one complementary cut-out 409 formed in the electrode patch 400 to align and/or retain the electrode patch 400 onto the top surface 905c of the connector device 900. The protrusion 935 may be substantially rectangular or substantially cuboid in shape. The protrusion 935 may be of a size that is sufficient to prevent at least a lateral movement of the electrode patch between the first end portion 905a and the second end portion 905b when the protrusion 935 is received by the at least one complementary cut-out formed in the electrode patch.

The alignment pins 935 are configured to be received by complementary alignment holes 414 formed in the electrode patch 400. The alignment pins 935 may be located on either or both sides of the protrusion 930. In the example shown in FIG. 23, 6 alignment pins 935 are located on both sides (lateral sides) of the protrusion 930. The alignment pins may be more than or less than 6.

Figure 24:
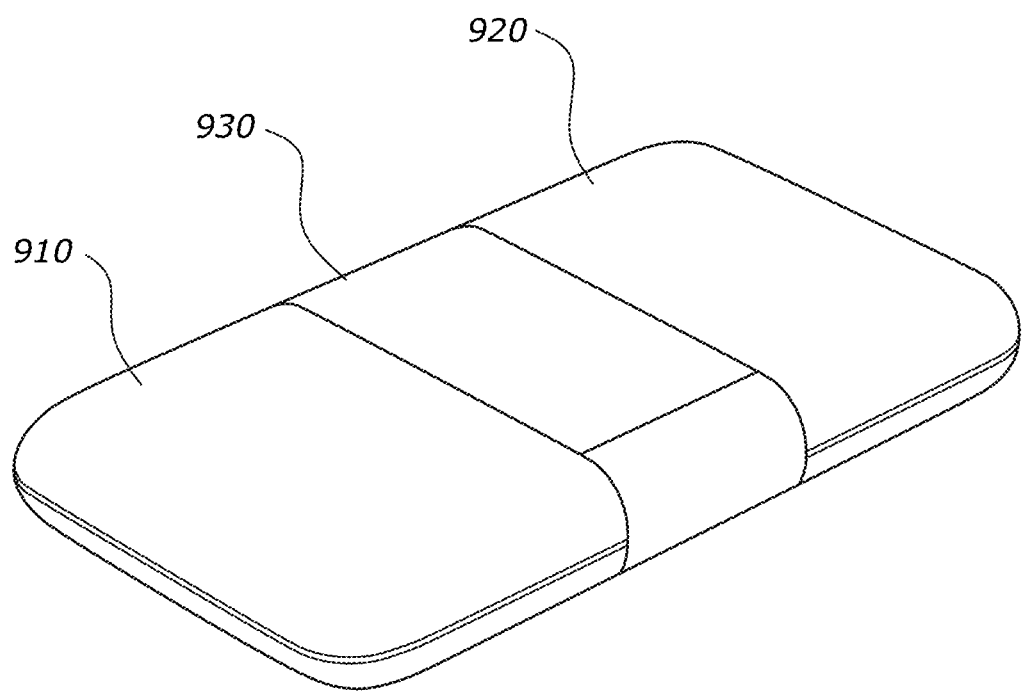
FIG. 24 shows an example/embodiment of the connector device of FIG. 23 in a closed/clamped position.

As shown in FIG. 24, in the closed position the first clamping member 910 and the second clamping member 910 may both be configured to move pivotally towards the top surface and at least partially (preferably fully) conceal the top surface 905c save for the protrusion 930 or at least the portion thereof.

The connector device 900 is preferably a wearable electronic device. Preferably, the main body 905, the first clamping member 910, and the second clamping member 920 together form a housing inside which various electronic components of the connector device are at least partially disposed. In FIG. 23, the connectors 950 are shown to slightly protrude out from the first and second clamping members 910, 920.

The connector device 900 may comprise an electronic circuit and a memory with the instructions stored in the memory. The implementation of the instructions may cause the connector device 900 to receive signals from the electrode patch 400, process the signals, and transmit data to a remote computing device to allow monitoring of electrical activity generated by the subject. The electronic device may be a data acquisition device or data logging device. The data may be transmitted wirelessly and/or with a wire to a computing device for processing, filtering or analysis.

Preferably, the connector device 900 is battery powered (e.g. by a Li-ion battery). The principals and operations of the data acquisition device or data logging device are well known to a person skilled and need not be described here. However, the connector device 800 may comprise at least one analogue to digital convertor to amplify and digitize a biopotential measurements signals received from the electrode patch 400. There may be multiple (e.g. four) analogue to digital convertors. The analogue to digital convertor(s) may be analogue to digital convertor chip(s). The connector device 800 may comprise a microcontroller. The microcontroller may be configured to receive signals from the analogue to digital convertor, process the signals, and transmit data to a remote computing device to allow monitoring of electrical activity generated by the subject. The analogue to digital convertor(s) may be electrically connected to the microcontroller with a flexible cable(s). The flexible cable(s) may be flexible printed circuit board(s). The electronic component may further comprise a flash memory, Near Field Connection (NFC) module(s) and/or charging circuit(s).

FIGS. 25-29 show an example of a docking device 1500 of the connector device 900 and how the docking device 1500 may be used to receive the connector device 900. As shown, the docking device 1500 may comprise a compartment 1550 which is a connector device receiving compartment.

Figure 25:
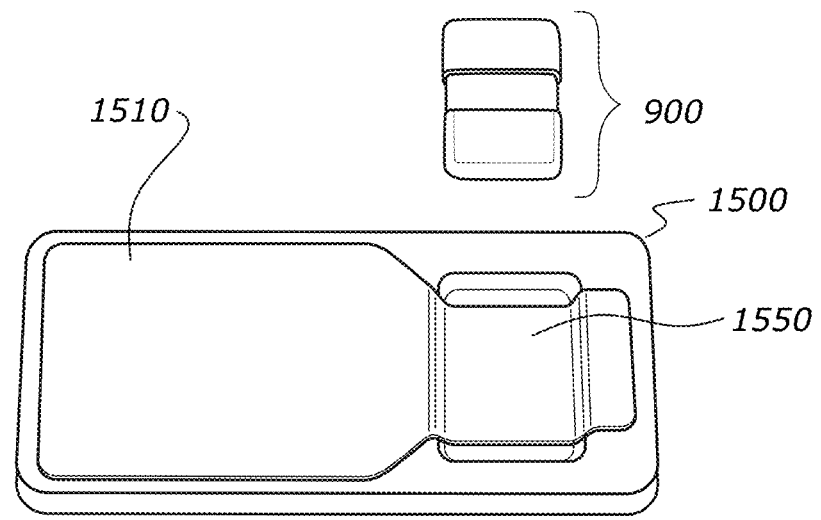
FIGS. 25-30 sequentially show how the connector device of FIG. 23 may be placed on a docking device and how the connector device of FIG. 23 may be used for connecting to an electrode patch.

The docking device 1500 may be a wireless charging device for facilitating wireless or contact charging of the connector device when the connector device is received within the compartment 1550 as shown in FIG. 25. The principals and designs of the wireless or contact charging device is well known to a person skilled and need not be described here.

One purpose of the docking device 1500 is to provide a large flat surface 1510 where the operator can conveniently assemble the electrode patch 400' and the connector device 900 together. The electrode patch 400' (shown in FIGS. 28, 29, 30) may be substantially the same as electrode patch 400 as described above. The only major difference being in the number of electrodes. The electrode patch 400' may comprise 64 array electrodes 402', a ground electrode 402a' and a reference electrode 402b'. However, the electrode patch 400' may have more than or less than 64 electrodes. In FIGS. 23-25, the electrical conductors and the connector portions, the alignment holes, the adhesives are not shown for the sake of clarity. In FIGS. 20-25, the alignment pins 935 are not shown for the sake of clarity. In FIGS. 25-29, the front portion 400a' of the electrode patch 400 is shown. In FIG. 30, the rear portion 400b' of the electrode patch 400 is shown.

The mode of assembly in one embodiment occurs as follows.

The connector device 900 is placed into a depression, i.e. compartment 1550 within the surface of the docking device 1500. The connector device 900 has a consistent geometry with this compartment 1550 so that a correct orientation is readily achieved. The clamping members 910, 920 formed on the connector device 900 are then moved to the opened position to expose the connectors 950. The electrode array 400' is then positioned on the flat surface 1510 of the docking device 1500. This flat surface 1510 preferably has enough friction so that the electrode patch 400', which may be made of a material that is slippery, remains easily in position. The electrode array 400' is then draped over the open surface of the connector device 900, and the alignment holes and pins of the electrode patch 400' and the connector device 400' respectively are matched. The clamping members 910, 920 on the connector device 900 are then moved to the closed position securely onto the electrode patch 400', forming a tight connection at the correct alignment.

A person skilled in the art may appreciate that the connectors 950 should not be cleaned with clinical disinfectant solution to prevent being clogged with residues and/or to prevent being damaged due to cleaning, however the connector device 900 may need to be cleaned between patients for hygiene reasons. The connector device 900 of the invention allows easy cleaning and avoid accidental cleaning of the connectors 950 because the connectors 950 of the connector device 900 are only exposed when the clamping members 910, 920 are in the open position. In order to clean the connector device 900, the clamping members 910, 920 can be moved to the closed position and wiped with clinical disinfectant and that may avoid cleaning of the connectors 950. Further, since the connectors 950 are only exposed when the clamping members 910, 920 are in the open position, there is a less prone to damage and less prone to clogging by dust or similar.

Another purpose of the docking device 1550 is to charge the connector device 900 when it is not in use. This can be achieved by having a contact charging points. Alternatively, a wireless charging coil (not shown) may be placed at a suitable location, preferably beneath the compartment 1550 in the docking device 1500. A consistent geometry between the connector device 900 and the compartment 1550 in the docking device 1500 ensure that the charging connection is made reliable. The compartment 1550 may shaped and sized to snugly receive the connector device 900 within the compartment 1550 and that can ensure that the charging connection between the docking device 1500 and the connector device 900 is reliable.

A significant force must be achieved at the connection between electrode patch 400 and first and second connection members 910, 920 for a connection device. In connection device 900, the first and second clamping members 910, 920 may be locked in a closed position by magnets. However, other suitable locking means such as latch arrangement, snap fit arrangement etc. are equally possible.

A preferred method of using the system 2000 comprising the coupling device 900, the docking device 1500 and an electrode patch 400' will now be further described with reference to FIGS. 25-30. As mentioned above, the electrode patch 400' (shown in FIGS. 28, 29, 30) may be substantially the same as electrode patch 400 as described above. The only major difference being in the number of electrodes. The electrode patch 400' may comprise 64 array electrodes 402', a ground electrode 402a' and a reference electrode 402b'. However, the electrode patch 400' may have more than or less than 64 electrodes.

FIG. 25 shows the docking device 1500 that is ready to receive the connector device 900 inside the depression, i.e. the compartment 1550.

Figure 26:
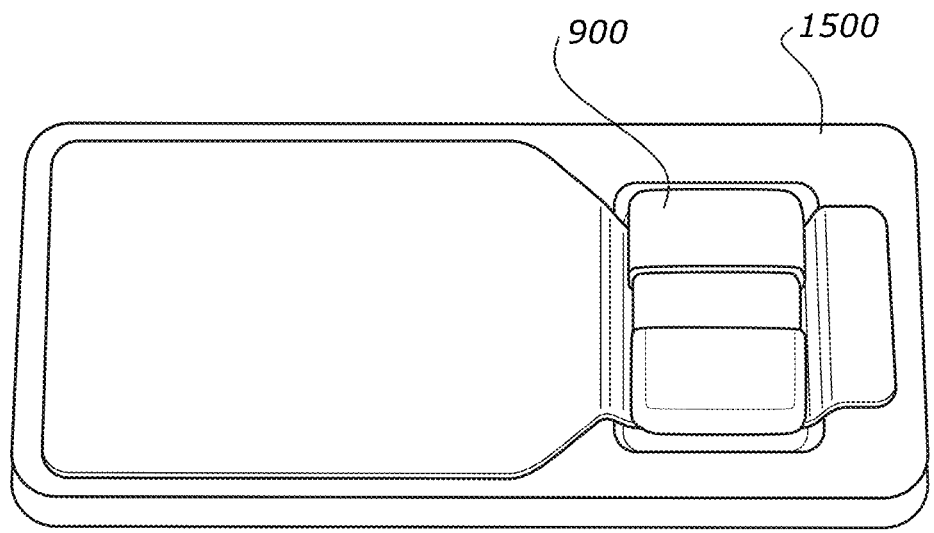
Figure 27:
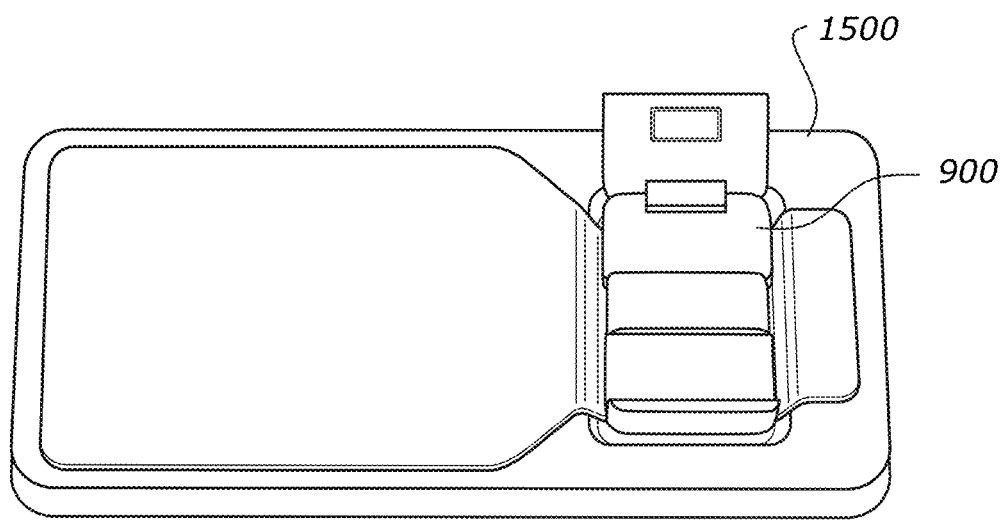

As shown in FIG. 26, the connector device 900 is placed in the docking device 1500, more specifically the connector device 1500 is placed within the compartment 1550 formed in the docking device 1500. Also, when not in used, the connector device 900 may be placed in the docking device as shown in FIG. 21 to allow the connection device to be charged wirelessly or by contact charging.

The electrode patch 400' is positioned on the flat surface 1510 of the docking device. This flat surface 1510 preferably has enough friction so that the electrode patch 400', which may be made of a material that is slippery, remains easily in position. The electrode patch 400' is then draped over the open surface of the connector device 900.

Figure 28:
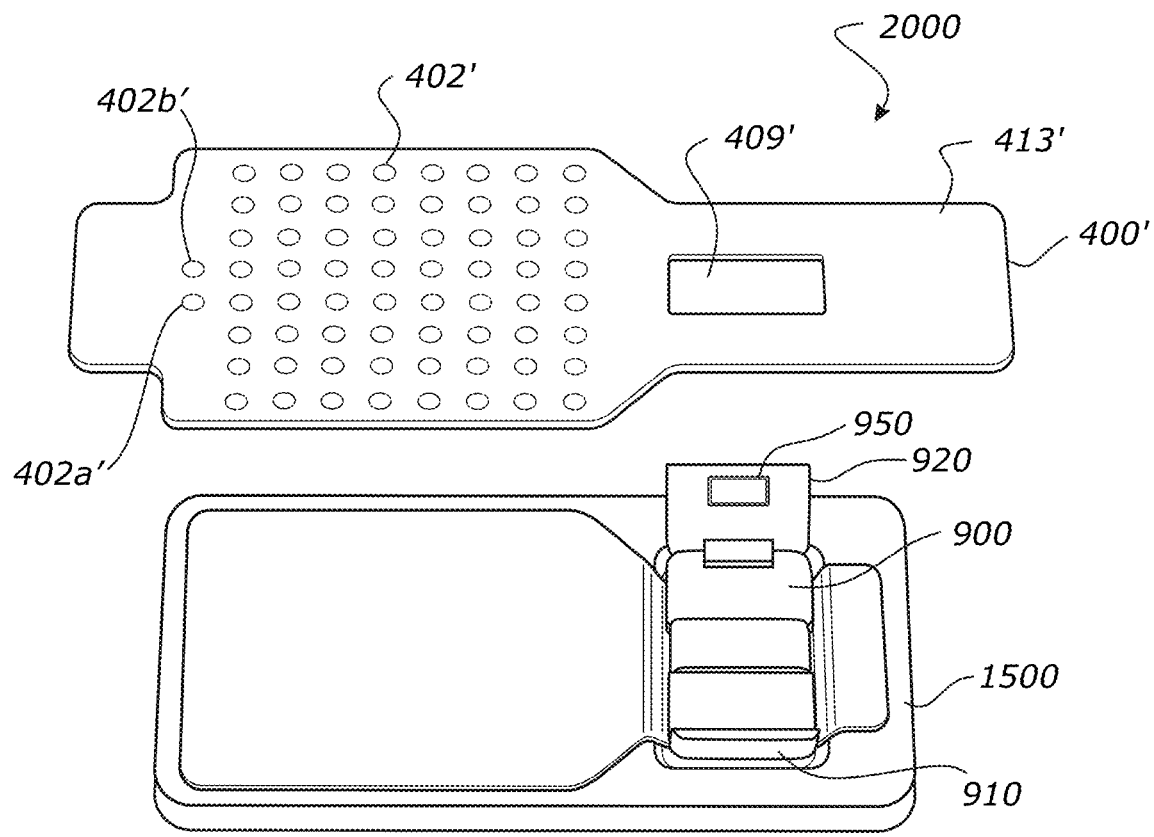

In order to couple the electrode patch 400' with the connector device 900, the first and second clamping members 910, 920 are moved to be in open position as shown in FIG. 28.

The electrode patch 400' is then guided down into the connector device 900.

Close or exact alignment of the connector portions of the electrode patch and the connectors 950 on the first and second clamping members 910, 920 are necessary for reliable coupling. This is achieved by the alignment features in the form of protrusion 930 that is received by the cut-out 409' and alignment pins 935 that are received by the alignment holes of the electrode patch 400'. As mentioned above, in FIGS. 25-29, the alignment pins 935 and complementary alignment holes to receive the alignment pins 935 are not shown for the sake of clarity. The protrusion and the alignment pins help to prevent skewing of the electrode patch and allows close or exact registration of the connector 950 to the connector portions of the electrode patch. This can help prevent failed connections and cross talks.

The first and second clamping members 910, 920 are then moved to the closed position where each clamping member 910, 920 clamps the portion of the electrode patch (connection portions of the electrode patch) between that clamping member and the top surface 905a of the connector device 900.

The connector device 900 and the connector device assembly in assembled configuration as shown in FIG. 30 is then ready for attachment to outer surface of the skin of the subject. By having a tongue 403' with adhesive on the one side (right side) of the connector device 900 and remaining portion on the other side (left side) with adhesive on the edges (see adhesive 413 shown in FIG. 22), the electrode patch 400' and connector device assembly can stick firmly to the outer surface of the skin of the subject on each side of the connector device 900. This also means that the electrode patch 900 may be well attached on each side of the connector device 900 and does not dislodge easily.

In some embodiments, the top surface of the protrusion may comprise a display screen for displaying useful information to the user. Such useful information may be information relating to the electrical activity that is being monitored using the connector device 900, or information on connectivity, test status or device errors.

Figure 31:
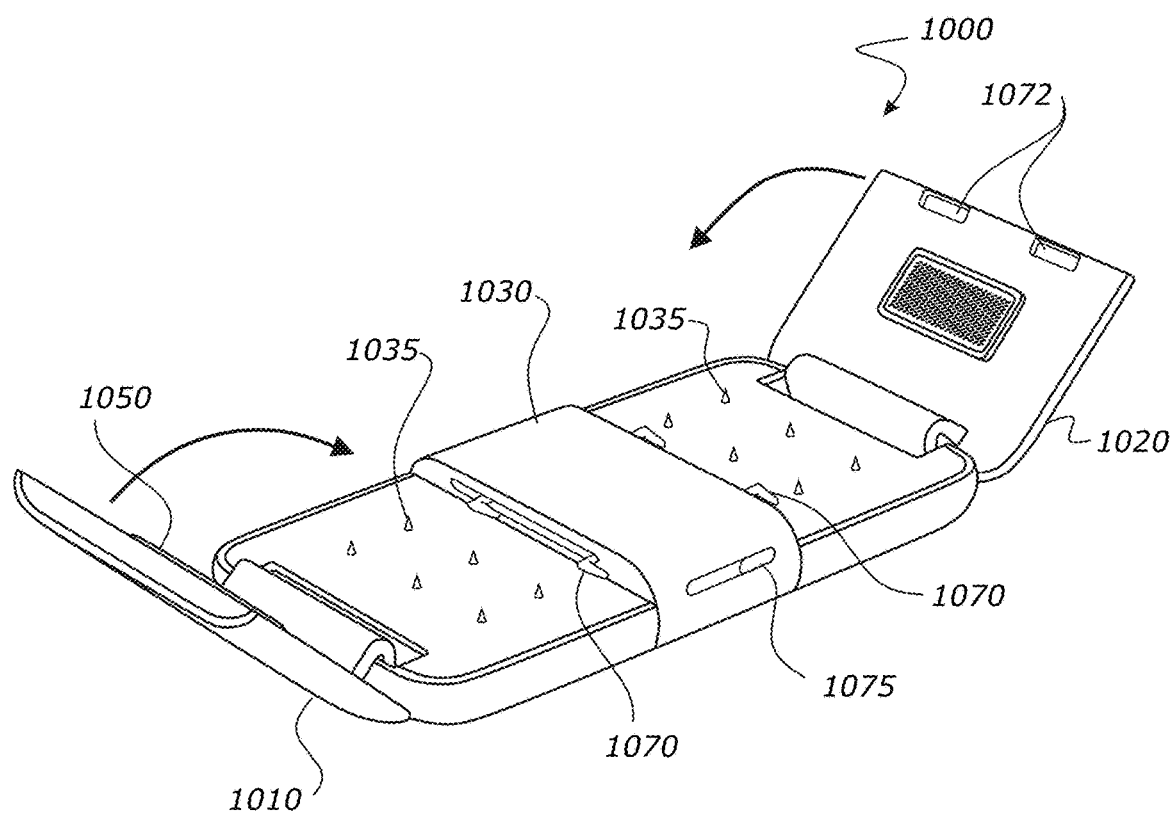
FIG. 31 shows an example/embodiment of a connector device according to a sixth preferred embodiment in an open/release position.

FIG. 31 shows a connector device 1000 according to another preferred embodiment of the invention. Connector device 1000 of this example is similar in most aspects to the connector device 900 described above and the differences can be identified by comparing FIG. 23 with FIG. 31. In FIG. 31, the features that are similar to those shown in FIG. 23 are identified with the same reference numeral, incremented by 100. Most of the description of the connector device 900 of a preferred embodiment above, equally applies to the connector device 1000 and therefore, only the differences will be discussed.

As shown, the connector device 1000 may comprise latching arrangement comprising latches 1070 that are configured to engage with catches 1072 formed on the first and second clamping members 1010, 1020 when in the closed position. In FIG. 31, only catches 1072 on the second clamping member 1020 can be seen. The engagement of the latches 1070 with the latches 1072 allow the first and second clamping members to remain in the closed position. As shown, the connector device may comprise a push button 1075, which when depressed may allow the latches to move their position thereby disengage with the catches to allow the first and second clamping members to be in the open position. Preferably, the first and second clamping members 1010, 1020 are spring biased to be in open position so that when the push button 1075 is depressed, the latches 1070 disengage with the catches 1072 and both the first and second members 1010, 1020 move from the closed position to the open position. As shown, the latches may be position on each side of the protrusion 1030. The latches 1072 and the protrusion 1030 may both be received by the cut-out 400' of the electrode patch 400' when the electrode patch 400' in position on the top surface 1005c of the connector device 1000. Instead of a push button 1075, a sliding button or many other suitable types of buttons may be used which when slide either on one side cause the latches 1070 to disengage with the catches 1072. The latches 1070 are preferably mechanical latches. Many other suitable latches and catches arrangement may be used.

Figure 32:
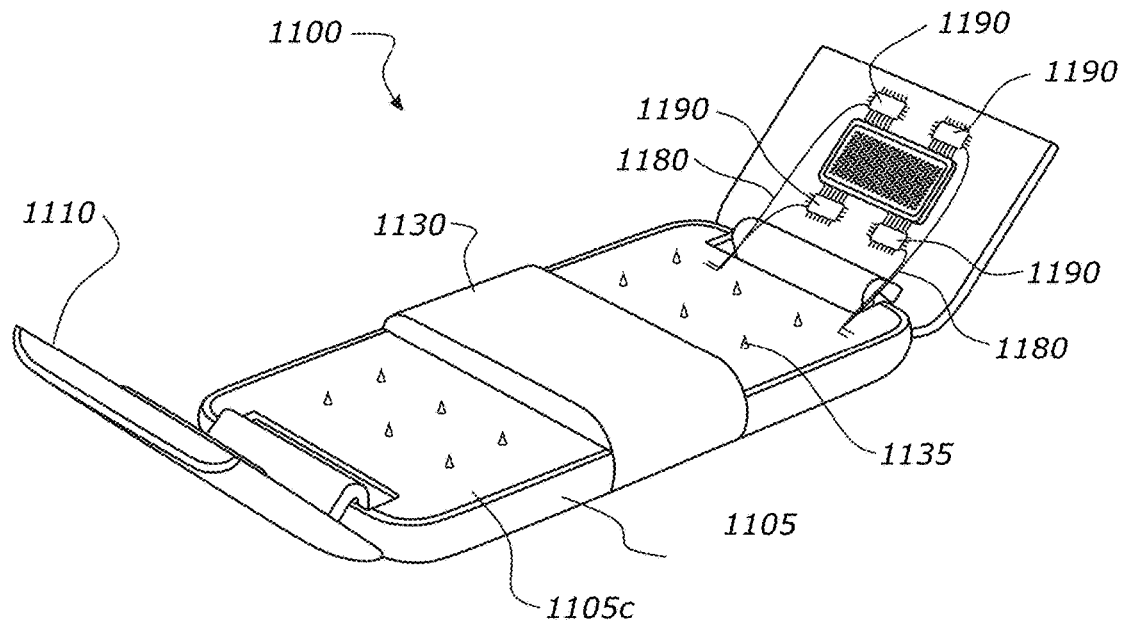
FIG. 32 shows an example/embodiment of a connector device according to a seventh preferred embodiment in an open/release position. An electrode patch according to a further preferred example/embodiment of the invention is also shown.

FIG. 32 shows a connector device 1100 according to another preferred embodiment of the invention. Connector device 1100 of this example is similar in most aspects to the connector device 900 described above and the differences can be identified by comparing FIG. 23 with FIG. 32. In FIG. 32, the features that are similar to those shown in FIG. 23 are identified with the same reference numeral, incremented by 200. Most of the description of the connector device 900 of a preferred embodiment above, equally applies to the connector device 1100 and therefore, only the main differences will be discussed.

The key feature of the connector device 900 is a plurality of amplifier chips 1190 (which may be analogue to digital convertor chips) next to the connector 1150. This is useful at least for the following reasons:

It allows conversion of the signals from the electrode patch 400' immediately to a digital signal. This means that only a small number of wires 1180 are required to be routed across the clamping members 1120, 1120 to the main body 1105. It can be appreciated that if the amplifier chips 1190 were on the main body 1105 of the connector device 1100 then that will require to route larger number of wires (e.g. 66 wires for 66 electrodes) across the hinged clamping members 1110, 1120, which could be problematic for the design or operation of the clamping members 1110, 1120, or lead to increased wear and failure rates.

Rapid digital conversion also means higher signal quality as there is less signal loss/noise with shorter distances, less wire and less connections.

The connector device 1000 may also have plurality of amplifier chips next to the connector 1150.

Figure 33:
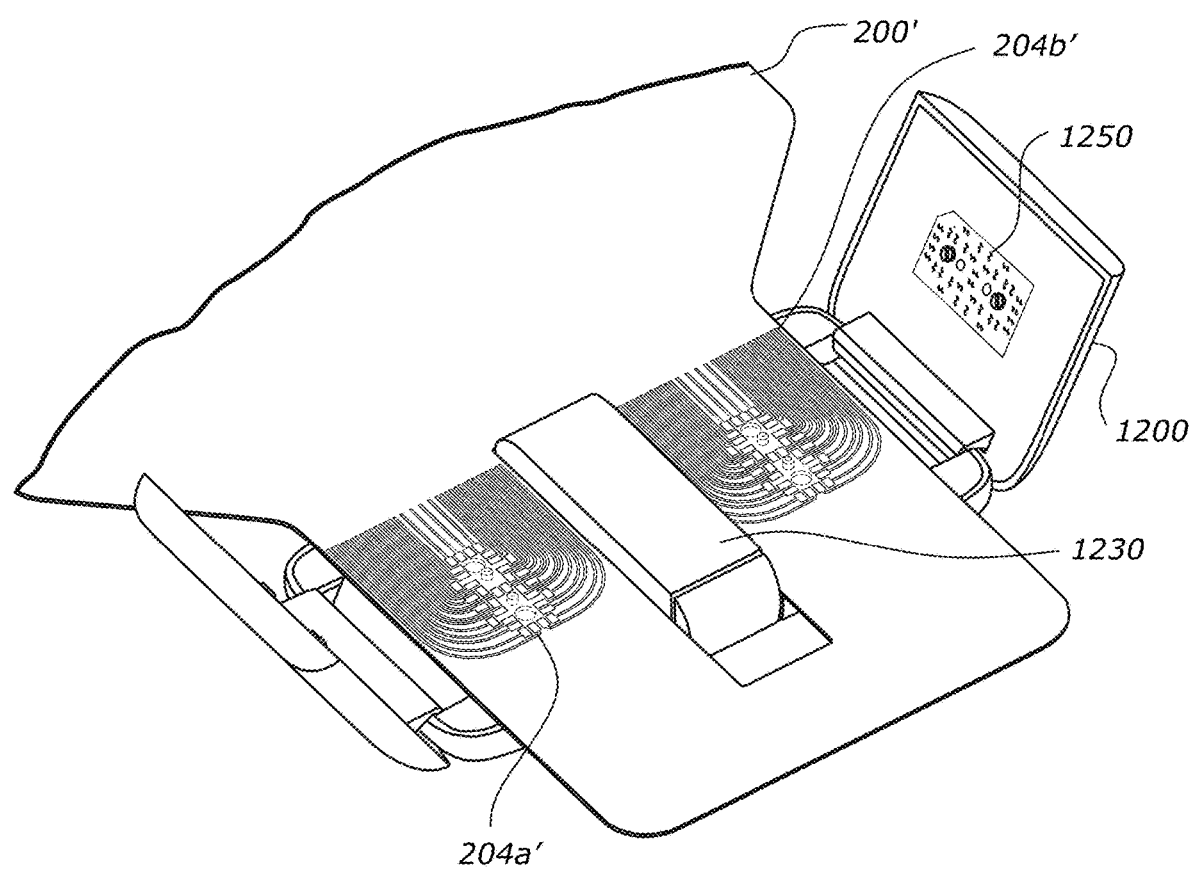
FIG. 33 shows an example/embodiment of a connector device according to an eighth preferred embodiment in an open/release position. An electrode patch according to a further preferred example/embodiment of the invention is also shown.

FIG. 33 shows an electrode patch 200' according to another preferred embodiment that is placed on a connector device 1200 according to another preferred embodiment.

The electrode patch 200' is substantially the same as electrode patch 200 described above. Hence, most of the description of electrode patch 200 of a preferred embodiment above, equally applies to the electrode patch 200' and therefore need not be described again.

The electrode patch 200' comprises connection portions 204a' and 204' that are similar to connection portion 204 described with reference to FIGS. 10 and 11. Most of the features of the electrode patch 200' such as electrodes and full electrical conductors are not shown in FIG. 33 for the sake of clarity. The electrode patch 200' may comprise 66 array electrodes and ground electrode and a reference electrode similar to electrode patch 200 as described above with reference to FIG. 9. Alternatively, the electrode patch 200' may comprise more than or less than 66 array electrodes and a ground electrode and a reference electrode.

The connector device 1200 is substantially same as connector device 900 as described above. Hence, most of the description of electrode patch 200 of a preferred embodiment above, equally applies to the electrode patch 200 and therefore need not be described again. The only difference lies in the connector 1250 of the electrode device 1200 which is same as connector 350 described above with reference to FIGS. 13 and 14. Alternatively, the connector 1250 may be same as the connector 450 as described above with reference to FIGS. 16-18.

Figure 34:
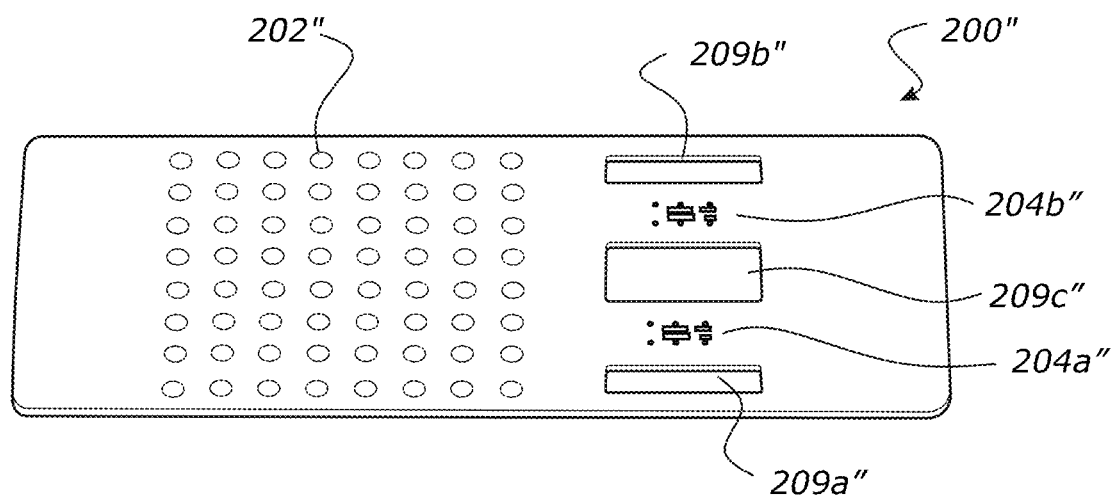
FIG. 34 shows an electrode patch according to a fifth preferred embodiment of the present invention.

FIG. 34 discloses an electrode patch 200" according to a further preferred embodiment of the present invention. The electrode patch 200" is substantially the same as electrode patch 200 described above. Hence, most of the description of electrode patch 200 of a preferred embodiment above, equally applies to the electrode patch 200' and therefore need not be described again.

The electrode patch 200" comprises connection portions 204a" and 204b" that may be similar to connection portion 204 described with reference to FIGS. 10 and 11. Most of the features of the electrode patch 200" such as full electrical conductors are not shown in FIG. 34 for the sake of clarity. The electrode patch 200" may comprise same number of electrodes as described above with reference to FIG. 9. It is possible that electrode patch 200" comprises more than or less than 64 electrodes are shown in FIG. 34.

As shown in FIG. 34, there are at least three cut-outs 209a", 209b" and 209c".

Figure 35:
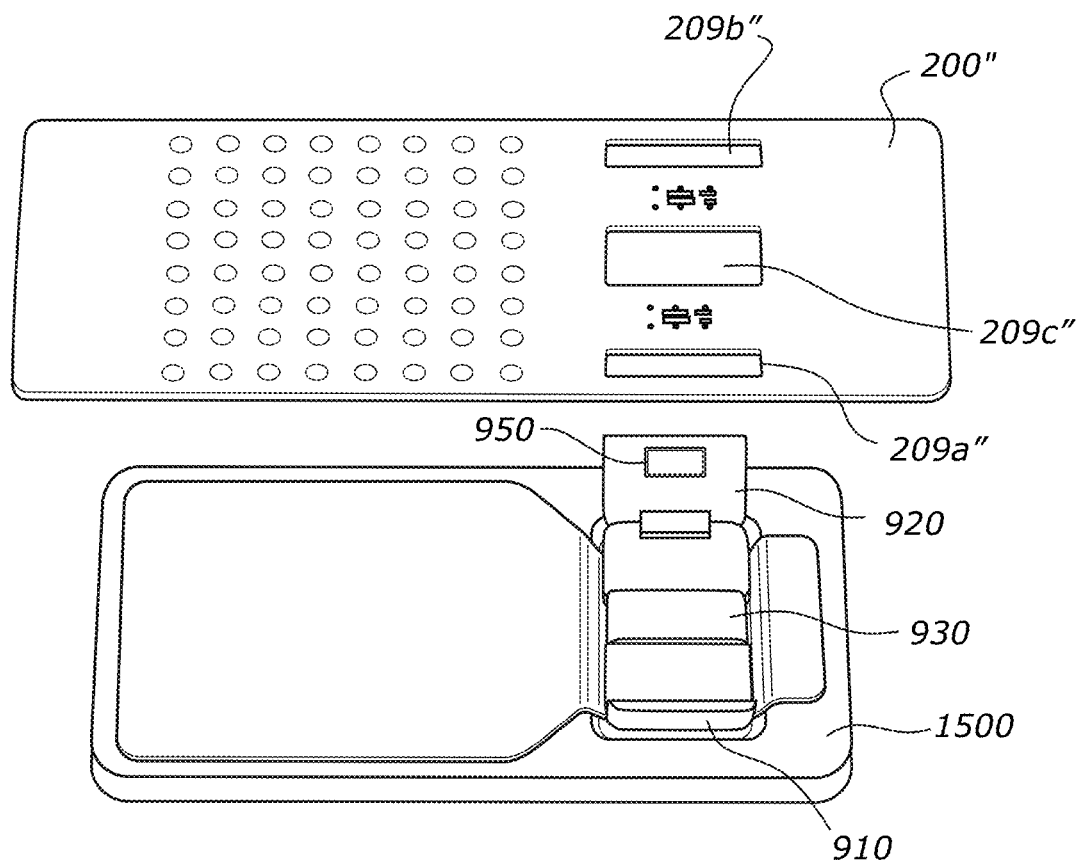
FIG. 35 shows the electrode patch of FIG. 34 about to be engaged with the connector device of FIG. 23 that is placed on a docking device.

In order to couple the electrode patch 200" with the connector device 900, the first and second clamping members 910, 920 are moved to be in open position as shown in FIG. 35. The electrode patch 200" is then guided down into the connector device 900.

Figure 36:
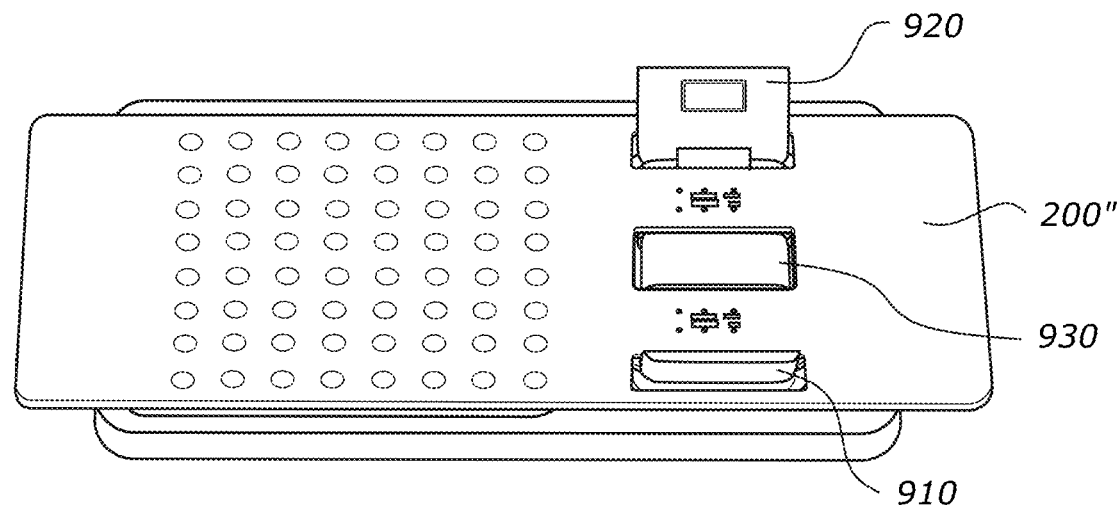
FIG. 36 shows the electrode patch of FIG. 35 engaged with the connector device of FIG. 23 that is placed on a docking device with the connector device of FIG. 23 being in an open/released position.

Close or exact alignment of the connector portions 204a" and 204b" and the connectors 950 on the first and second clamping members 910, 920 are necessary for reliable coupling. This is achieved by the alignment features in the form of protrusion 930 that is received by the cut-out 209c" and alignment pins 935 that are received by the alignment holes of the electrode patch 200". The alignment pins 935 are not shown in FIGS. 35-37 for the sake of clarity but can be seen for example in FIG. 23. The protrusion 930 and the alignment pins 935 help to prevent skewing of the electrode patch and allows close or exact registration of the connector 950 to the connector portions of the electrode patch. This can help prevent failed connections and cross talks.

Figure 37:
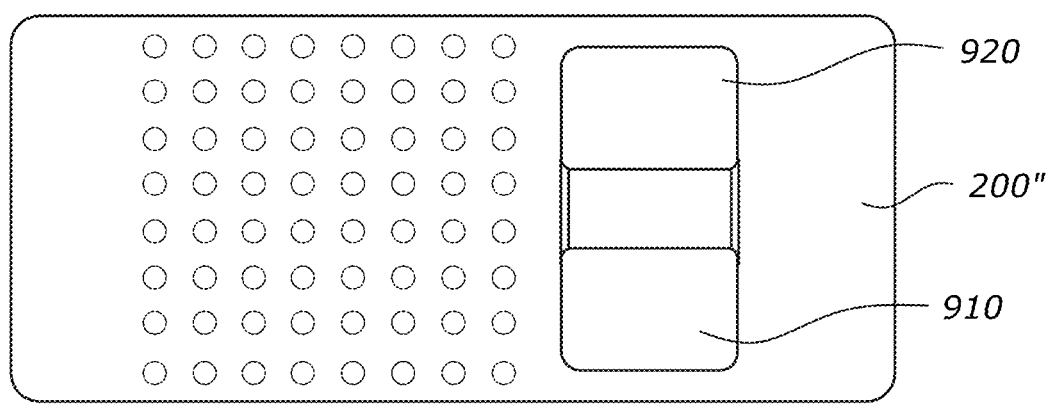
FIG. 37 shows an example/embodiment of a connector device the electrode patch of FIG. 35 engaged with the connector device of FIG. 23 with the connector device of FIG. 23 being in a closed/clamped position.

The connector device 900 and the connector device assembly in assembled configuration as shown in FIG. 37 is then ready for attachment to outer surface of the skin of the subject. As it can be appreciated from FIGS. 34-37, tongue in the electrode patch may be optional. The electrode patch may equally be used with devices 1000, 1100 and 1200 as described above.

The first and second clamping members 910, 920 are then moved to the closed position where each clamping member 910, 920 clamps the portion of the electrode patch (connection portions of the electrode patch) between that clamping member and the top surface 905a of the connector device 900.

Figure 29:
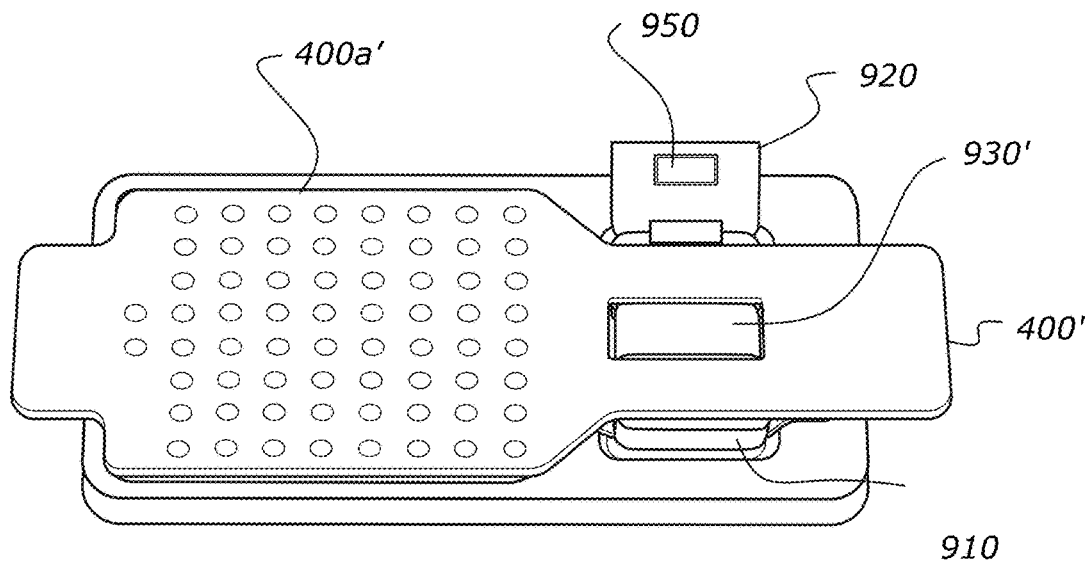
Figure 30:
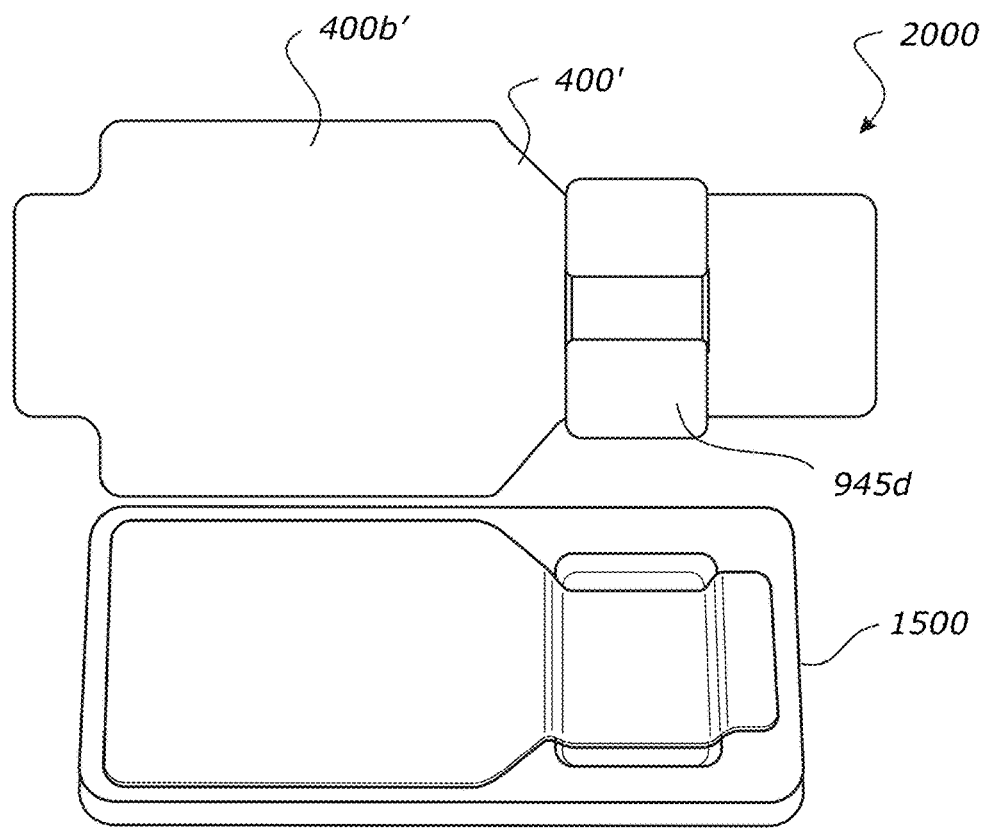

In certain embodiments, cut-outs 209a" and 209b" may not be present and the dimension of the electrode patch 200" may be such that it is able to fit between the first and second clamping members 910, 920 in a similar manner as shown in FIG. 29.

Figure 38:
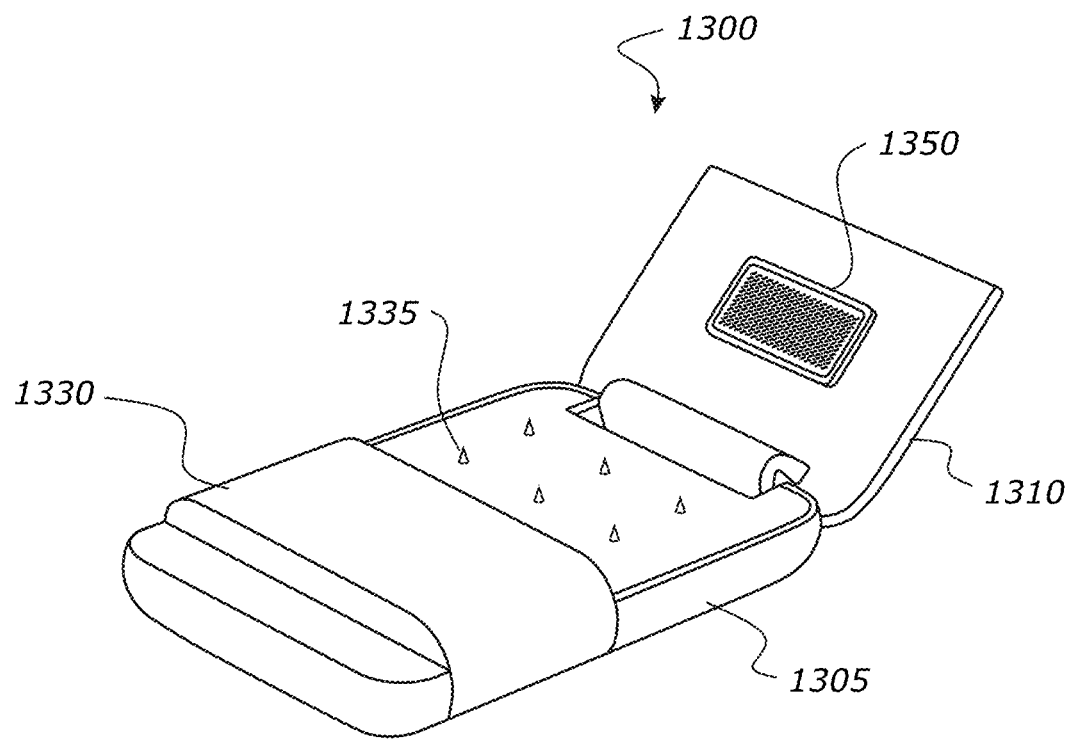
FIG. 38 shows an example/embodiment of a connector device according to a ninth preferred embodiment in an open/release position.
Figure 39:
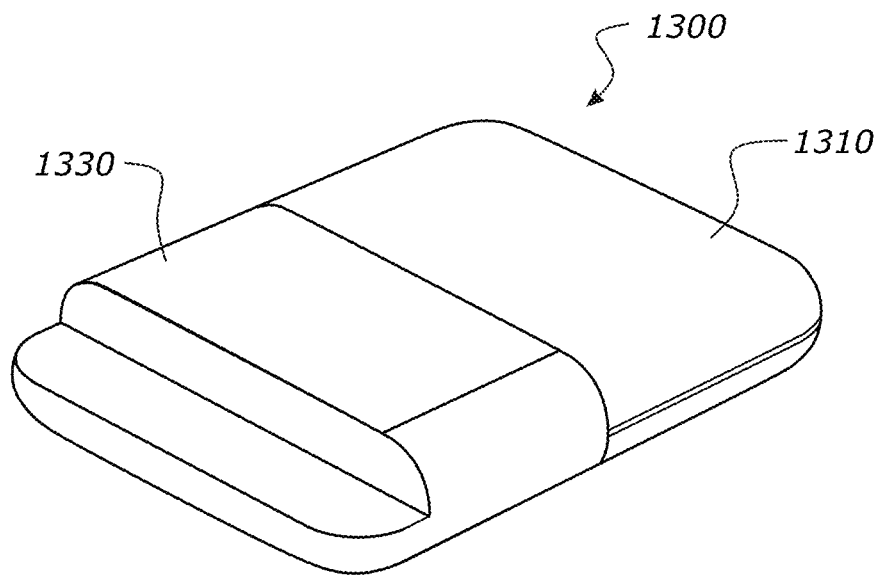
FIG. 39 shows an example/embodiment of a connector device according to a ninth preferred embodiment in a closed/clamped position.

FIGS. 38 and 39 show a connector device 1300 according to another preferred embodiment of the invention. Connector device 1300 of this example is similar in most aspects to the connector device 900 described above and the differences can be identified by comparing FIG. 23 with FIG. 38. In FIG. 31, the features that are similar to those shown in FIG. 23 are identified with the same reference numeral, incremented by 400. Most of the description of the connector device 900 of a preferred embodiment above, equally applies to the connector device 1000 and therefore, only the differences will be discussed.

As shown, the connector device 1300 may comprises only one clamping member 1310 that is hinged mounted to the main body 1305. Although, it may also be appreciated that the main body 1305 also facilitates clamping of an array positioned between the clamping member 1310 and the main body 1305 and in such a sense the main body 1305 can be interpreted as a second clamping member. The connector device 1300 can be considered as a truncated version of the connector device 900 and due to its smaller size, it is less heavy than connector device 900. Due to its size and weight, the connector device 1300 can be useful for monitoring electrical activity of pediatric subjects.

The connector device 1300 may also have one or more features of the connector devices 1000, 1100 and 1200 such as but not limited to push button, sliding button, latches, display screen etc.

Figure 40:
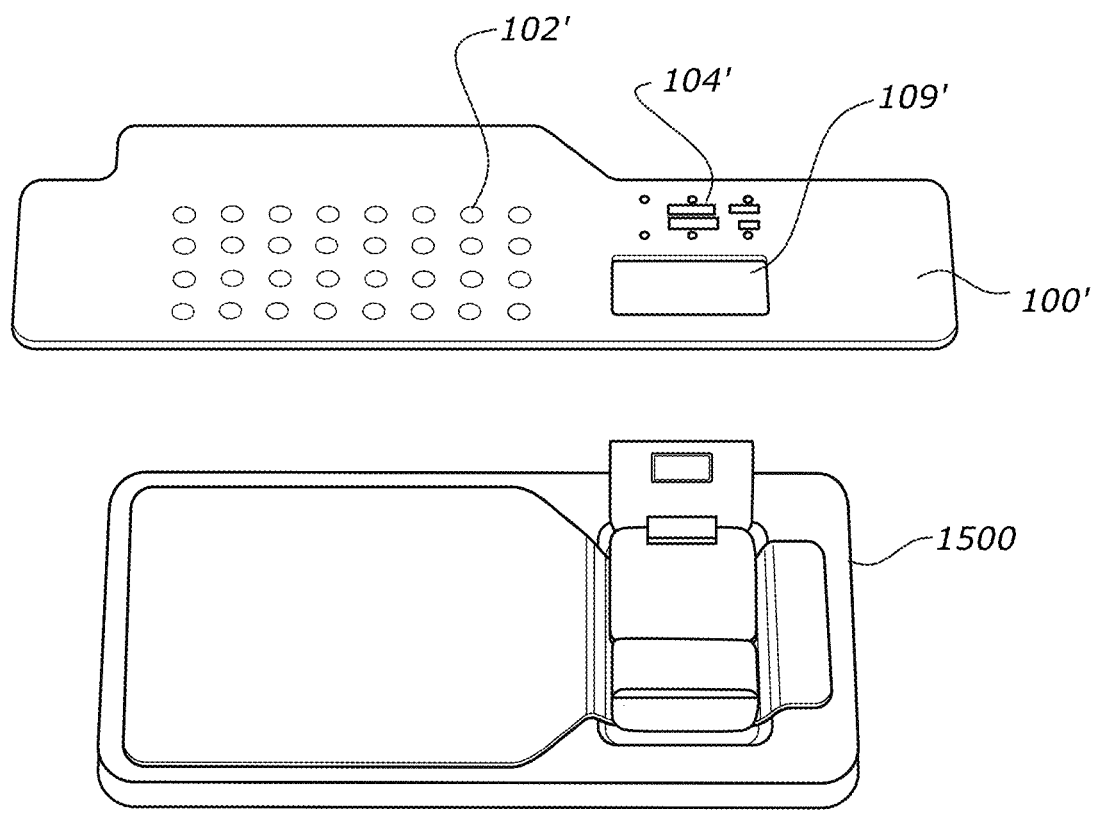
FIG. 40 shows an example/embodiment an electrode patch according to a further preferred example/embodiment that is about to be engaged with the connector device of FIG. 37 that is placed on a docking device.

FIG. 40 shows an electrode patch 100' according to a further preferred embodiment of the present invention. The electrode patch 100' is substantially the same as electrode patch 100 described above. Hence, most of the description of electrode patch 100 of a preferred embodiment above, equally applies to the electrode patch 100' and therefore need not be described again and the differences can be identified by comparing FIG. 40 with FIG. 1. In FIG. 40, most features such as full electrical conductors are not shown for the sake of clarity.

One main difference between electrode patch 100' and electrode patch 100 is the number of electrodes. The electrode patch 100' may comprise lesser number of electrodes than electrode patch 100. In the example shown in FIG. 40, there are only 32 electrodes in the electrode patch 100' as it is intended to be used on a pediatric subject.

In order to couple the electrode patch 100' with the connector device 900, the clamping member 1310 is moved to be in open position as shown in FIG. 40. The electrode patch 100' is then guided down into the connector device 1300.

Close or exact alignment of the connector portion 104' and the connector 1350 on the clamping member 1310 are necessary for reliable coupling. This is achieved by the alignment features in the form of protrusion 1530 that is received by the cut-out 109' and alignment pins 1335 that are received by the alignment holes of the electrode patch 109'. In FIG. 40, the alignment pins 1335 are not shown for the sake of clarity but such pins can be seen in FIG. 38. The protrusion 1350 and the alignment pins 1330 help to prevent skewing of the electrode patch and allows close or exact registration of the connector 950 to the connector portion 104' of the electrode patch 100'. This can help prevent failed connections and cross talks.

The clamping member 1310 is then moved to the closed position where the clamping member 1300 clamps the portion of the electrode patch (connection portions of the electrode patch) between that clamping member and the top surface 1305a of the connector device 1300.

The connector device 1300 and the electrode patch 100' in assembled configuration is then ready for attachment to outer surface of the skin of the subject, preferably pediatric subject.

It may be appreciated that the size, shape and number of electrodes in the electrode patches may differ from what is described above and depicted in the accompanying drawings which are described and shown in this specification by way of examples only.

Where in the foregoing description reference has been made to elements or integers having known equivalents, then such equivalents are included as if they were individually set forth.

It will of course be realized that while the foregoing description has been given by way of illustrative example(s) of the invention, all such modifications and variations thereto as would be apparent to a person skilled inf the art are deemed to fall within the broad scope and ambit of the various aspects of invention as is hereinbefore described and/or defined in the claims.

What is claimed is:

1. A system for monitoring gastro-intestinal or colonic electrical activity generated by a subject, the system comprising:
   an electrode patch comprising at least 32 electrodes spatially arranged in a plurality of rows and columns for contacting an outer surface of a skin of the subject to sense and measure electrical potentials at multiple electrodes, wherein the electrodes are routed to two connector portions that are spaced apart from the electrodes and are electrically connected with the electrodes through electrical conductors running as conductive tracks between the electrodes and said two connector portions with at least one cut-out entirely located between the two connector portions; and
   a wearable connector device having two connectors that are configured to be physically and operatively connected with the electrode patch or at least a portion of the electrode patch at each of said two connector portions for receiving the electrical signals from multiple electrodes to allow monitoring of gastro-intestinal or colonic electrical activity generated by the subject and wirelessly transmitting electrical activity data to a remote computing device, wherein the connector device is configured to be attached to the outer surface of the skin of the subject by having a tongue portion of the electrode patch on a first side of the connector device and a remaining portion of the electrode patch on a second side of the connector device that is opposite the first side of the connector device.

2. The system as claimed in claim 1, wherein the system further comprises a docking device having a compartment that is configured to receive the connector device.

3. The system as claimed in claim 1, wherein the electrode patch comprises a flexible substrate that is stretchable and comprises a thermoplastic polyurethane material.

4. The system as claimed in claim 1, wherein the at least one cut-out is substantially rectangular in shape.

5. The system as claimed in claim 1, wherein the electrode patch comprises an adhesive for allowing the electrode patch to attach to the outer surface of the skin of the subject.

6. The system as claimed in claim 1, wherein the connector device is portable and further comprising or in a form of a first clamping member and a second clamping member that are configured to move between a clamped position in which the first and second clamping members are configured to clamp an electrode patch for monitoring electrical activity generated by a subject or at least a portion of the electrode patch to allow physical and operative connection between the connector device and the electrode patch or the portion of the electrode patch, and a released position in which the first and second clamping members are configured to move away from the clamped position to allow the electrode patch or the portion of the electrode patch to be released from the connector device, wherein the connector device comprises a main body having a planar surface onto which the electrode patch or the portion of the electrode patch is configured to be placed, and wherein at least the main body and the first clamping member together form a housing inside which electronic components of the connector device are at least partially disposed.

7. The system as claimed in claim 6, wherein the connector device comprises a biasing member that is configured to bias at least one of the first and second clamping members to move towards a direction of the electrode patch.

8. The system as claimed in claim 6, wherein the connector device is configured to be attached to the outer surface of the skin of the subject using the electrode patch with an adhesive so that the electrode patch is attached on each side of the connector device.

9. The system as claimed in claim 1, wherein the at least 32 electrodes spatially arranged in a plurality of rows and columns comprises at least 64 electrodes spatially arranged in 8 rows and 8 columns.

10. The system as claimed in claim 9, further comprising a ground electrode and a reference electrode.

11. The system as claimed in claim 9, wherein the each of the electrodes are equally spaced apart from each other at 2 cm.

12. The system as claimed in claim 1, wherein the at least 32 electrodes are spatially arranged in a plurality of rows and columns of the remaining portion of the electrode patch.

13. The system as claimed in claim 12, wherein the tongue portion extends from the remaining portion and is narrower than the remaining portion and includes the two connector portions.

14. A system for monitoring gastro-intestinal or colonic electrical activity generated by a subject, the system comprising:
an electrode patch comprising at least 32 electrodes spatially arranged in a plurality of rows and columns for contacting an outer surface of a skin of the subject to sense and measure electrical potentials at multiple electrodes, wherein the electrodes are routed to two connector portions that are spaced apart from the electrodes and are electrically connected with the electrodes through electrical conductors running as conductive tracks between the electrodes and said two connector portions with at least one cut-out located between the two connector portions; and
a wearable connector device having two connectors that are configured to be physically and operatively connected with the electrode patch or at least a portion of the electrode patch at each of said two connector portions for receiving the electrical signals from multiple electrodes to allow monitoring of gastro-intestinal or colonic electrical activity generated by the subject and wirelessly transmitting electrical activity data to a remote computing device;
wherein the connector device is portable and further comprising or in a form of a first clamping member and a second clamping member that are configured to move between a clamped position in which the first and second clamping members are configured to clamp an electrode patch for monitoring electrical activity generated by a subject or at least a portion of the electrode patch to allow physical and operative connection between the connector device and the electrode patch or the portion of the electrode patch, and a released position in which the first and second clamping members are configured to move away from the clamped position to allow the electrode patch or the portion of the electrode patch to be released from the connector device, wherein the connector device comprises a main body having a planar surface onto which the electrode patch or the portion of the electrode patch is configured to be placed, and wherein at least the main body and the first clamping member together form a housing inside which electronic components of the connector device are at least partially disposed;
wherein the main body comprises a first end portion and a second end portion that are located opposite to each other, wherein the first clamping member is mounted to the main body at or near the first end portion, and the second clamping member is mounted to the main body at or near the second end portion, and wherein in the clamped position the first clamping member and second clamping member are configured to move towards the planar surface of the main body and in the release position the first clamping member and second clamping member are configured to move away from the planar surface of the main body.

15. The system as claimed in claim 14, wherein the connector device comprises at least one alignment feature that is configured to align and/or retain the electrode patch or the portion of the electrode patch via an alignment hole onto the connector device.

16. The system as claimed in claim 14, wherein the connector device comprises at least one protrusion feature that is configured to align and/or retain the electrode patch or the portion of the electrode patch via the at least one cut-out onto the connector device, and wherein the at least one protrusion feature is located on or substantially on the planar surface between the first end portion and the second end portion.

17. An electrode patch system for monitoring gastro-intestinal or colonic electrical activity generated by a subject, the electrode patch system comprising:
an electrode patch comprising:
a primary region including a plurality of spatially arranged surface electrophysiological sensors in the form of electrodes for contacting an outer surface of a skin of the subject to sense and measure gastro-intestinal or colonic electrical potentials at multiple electrodes, wherein the electrodes comprise at least 32 electrodes arranged in a plurality of rows and columns; and
at least one tongue region extending from the primary region and being narrower than the primary region and including at least one connector portion, the at least one connector portion comprising a plurality of electrically conductive contact pads and being spaced apart at a distance from the electrodes, said plurality of electrically conductive contact pads being electrically connected with the electrodes through electrical conductors running as conductive tracks between the electrodes and said at least one connector portion; and
a wearable connector device configured to be physically and operatively connected with the at least one connector portion of the electrode patch for receiving the electrical signals from multiple electrodes to allow monitoring of gastro-intestinal or colonic electrical activity generated by the subject and wirelessly transmitting electrical activity data to a remote computing device, wherein the connector device is further configured to be attached to the outer surface of the skin of the subject using the electrode patch with an adhesive so that the primary region with adhesive is attached on a first side of the connector device and the tongue region with adhesive is attached on a second side of the connector device opposite the first side.

18. The electrode patch as claimed in claim 17, wherein the at least 32 electrodes spatially arranged in a plurality of rows and columns comprises at least 64 electrodes spatially arranged in 8 rows and 8 columns.

19. The electrode patch as claimed in claim 18, wherein the each of the electrodes are equally spaced apart from each other at 2 cm.

* * * * *